United States Patent
Fujii et al.

(10) Patent No.: US 7,229,801 B2
(45) Date of Patent: Jun. 12, 2007

(54) PRODUCTION METHOD AND PREPARATION METHOD OF GLUCANS

(75) Inventors: Kazutoshi Fujii, Osaka (JP); Yoshinobu Terada, Hyogo (JP); Michiyo Yanase, Hyogo (JP); Koji Odan, Osaka (JP); Hiroki Takata, Hyogo (JP); Takeshi Takaha, Hyogo (JP); Takashi Kuriki, Osaka (JP); Shigetaka Okada, Nara (JP)

(73) Assignee: Ezaki Glico, Co., Ltd., Osaka (JP)

( * ) Notice: Subject to any disclaimer, the term of this patent is extended or adjusted under 35 U.S.C. 154(b) by 452 days.

(21) Appl. No.: 10/475,943

(22) PCT Filed: May 27, 2002

(86) PCT No.: PCT/JP02/05125

§ 371 (c)(1),
(2), (4) Date: Oct. 24, 2003

(87) PCT Pub. No.: WO02/097107

PCT Pub. Date: Dec. 5, 2002

(65) Prior Publication Data

US 2004/0115778 A1 Jun. 17, 2004

(30) Foreign Application Priority Data

May 28, 2001 (JP) ............................. 2001-159744

(51) Int. Cl.
*C12P 19/60* (2006.01)
*C12N 9/10* (2006.01)

(52) U.S. Cl. ................... 435/101; 435/194; 435/195; 536/123.12

(58) Field of Classification Search ............... 435/101, 435/194, 195; 536/123.12
See application file for complete search history.

(56) References Cited

U.S. PATENT DOCUMENTS 5,565,341 A * 10/1996 Takahashi et al. .......... 435/100
5,795,979 A * 8/1998 Kusatsu et al. ......... 536/123.12
5,849,720 A * 12/1998 Jamas et al. .................. 514/54

FOREIGN PATENT DOCUMENTS

| EP | 0 423 768 A1 | 4/1991 |
| EP | 0 639 645 A1 | 2/1995 |
| EP | 0 677 587 A1 | 10/1995 |
| JP | 58-216695 | 12/1983 |

OTHER PUBLICATIONS

Russell et al.; "Streptococcus Mutans gtfA Gene Specifies Sucrose Phosphorylase"; Infection and Immunity; vol. 56, No. 10; Oct. 1988; p. 2763-2765.
Takata et al.; "Purification and Characterization of α-Glucan Phosphorylase from *Bacillus Stearothermophilus*"; Journal of Fermentation and Bioengineering; vol. 85, No. 2; pp. 156-161; 1998.
Takaha; "Structure and Properties of *Thermus Aquaticus* α-Glucan Phosphorylase Expressed in *Escherichia Coli*"; J. Appl. Clycosci; vol. 48, No. 1; pp. 71-78; 2001.
Waldman, et al.; "The Enzymic Utilization of Sucrose in the Synthesis of Amylose and Derivatives of Amylose, Using Phosphorylases"; Carbohydrate Research, 157 (1986).

* cited by examiner

*Primary Examiner*—Elli Peselev
(74) *Attorney, Agent, or Firm*—Renner, Otto, Boisselle & Sklar, LLP

(57) ABSTRACT

A first method for producing glucan comprises the step of allowing a reaction solution containing sucrose, a primer, inorganic phosphate or glucose-1-phosphate, sucrose phosphorylase, and glucan phosphorylase to react to produce glucans. The maximum value of the sucrose-phosphate ratio of the reaction solution from the start of the reaction to the end of the reaction is no more than about 17. A second method for producing glucan comprises the step of allowing a reaction solution containing sucrose, a primer, inorganic phosphate or glucose-1-phosphate, sucrose phosphorylase, and glucan phosphorylase to react to produce glucans. The reaction is conducted at a temperature of about 40 C to about 70 C.

50 Claims, 12 Drawing Sheets

PRODUCTION METHOD AND PREPARATION METHOD OF GLUCANS

The present application is filed as a U.S. National Stage application under 35 U.S.C. §371, based on International Application No. PCT/JP02/05125, filed 27 May 2002, priority to which is claimed and which is hereby incorporated by reference in its entirety.

TECHNICAL FIELD

The present invention relates to a method for producing glucans and derivatives thereof. More particularly, the present invention relates to a method for extending an $\alpha$-1,4-glucan chain.

BACKGROUND ART

Glucan is a generic term for polysaccharides in which the saccharide components consist only of D-glucose. Examples of representative glucans include starch, cellulose, and the like. Starch is an $\alpha$-glucan in which saccharide components are linked by $\alpha$-glucoside bonds. In starch, amylose, which is a straight-chain $\alpha$-1,4-glucan, and amylopectin, having a branched structure, are present. The abundance ratio of amylose to amylopectin varies depending on the plant storing the starch. Therefore, it is very difficult to obtain starch containing amylose and amylopectin at an arbitrary composition ratio. If amylose can be stably produced, such amylose can be mixed with commercially available starch to produce starch having an arbitrary amylose content.

Conventionally, amylose and amylopectin having an arbitrary structure are produced by utilizing the action of hydrolyzing enzymes, transferases, and the like. However, reports on structural alteration of starch by extending its $\alpha$-1,4-glucan chain are limited. It is useful to develop a method for extending an $\alpha$-1,4-glucan chain efficiently since not only can amylose be produced but also the structure of starch can be arbitrarily modified.

It is known that in starch-containing foods, the content and structure of amylose in the starch has a great influence on the physical properties of the food. However, the content and structure of amylose in the starch is determined by the starch utilized as a raw material. If the content and structure of amylose can be arbitrarily changed, development of foods having novel mouthfeel can be expected.

Insoluble amylose is expected to have the same function as that of dietary fiber, and can also be expected to be utilized in health foods. Further, amylose has a feature that the amylose can include, for example, iodine, fatty acid, or the like in the molecule. Therefore, amylose is expected to be used in the fields of medicaments, cosmetics, and sanitary products. Amylose can also be utilized as a raw material for the production of cyclodextrin and cycloamylose having the same inclusion capacity as that of amylose. Further, films containing amylose have tensile strength not less than that of general-purpose plastics, and amylose is a very promising material for biodegradable plastics. Thus, amylose is expected to have a number of applications. However, it is difficult to obtain substantially pure amylose and such amylose is very expensive. Therefore, such amylose is only distributed as reagent grade, and is hardly utilized as industrial material. Accordingly, there is a demand for a method for producing amylose in a stable and inexpensive manner.

There are some known methods for producing amylose. Amylose is present in starch in a proportion of about 0 to 70%. Amylose can be extracted from natural material starch using precipitating agents, such as butanol, by a method described in T. J. Schoch et al., J. American Chemical Society, 64, 2957 (1942). However, this extraction operation is complicated and has a low yield. Further, it is difficult to obtain straight-chain glucan containing no $\alpha$-1,6-glucoside bonds by the extraction operation. Furthermore, it is difficult to extract straight-chain glucan having a narrow molecular weight distribution.

As a method for extending an $\alpha$-1,4-glucan chain enzymatically, there is a synthetic method in which a sugar nucleotide is used as a substrate, and the sugar moiety is transferred to maltotetraose or the like as a primer by means of glycogen synthase, starch synthase, or the like. However, this method has a disadvantage that sugar nucleotides, which are used as a substrate, are very expensive and therefore cannot be industrially utilized.

There is a method for synthesizing an $\alpha$-1,4-glucan chain by transferring the glycosyl group of $\alpha$-glucose-1-phosphate to a primer, such as maltoheptaose or the like by means of glucan phosphorylase (GP) derived from potato.

Further, a method in which glucose-1-fluoride is used as a substrate and sucrose phosphorylase (SP) and glucan phosphorylase are simultaneously allowed to act on a primer, is disclosed (U.S. Pat. No. 5,405,449 and EP 0590736).

These synthesis methods have an advantage that the ratio of a substrate to a primer in a reaction solution at the start of reaction is arbitrarily set so that the molecular weight of the resultant straight-chain glucan can be controlled. However, the substrates, $\alpha$-glucose-1-phosphate and glucose-1-fluoride, are expensive, and therefore are not suitable for inexpensive production of a straight-chain $\alpha$-1,4-glucan which may be utilized in a wide range of industries.

As a method for producing straight-chain glucan in a more inexpensive manner, a method in which sucrose phosphorylase and glucan phosphorylase are simultaneously allowed to act on a primer and sucrose (hereinafter referred to as the SP-GP method) has been disclosed (Waldmann, H. et al., Carbohydrate Research, 157 (1986) c4-c7). Waldmann et al. synthesized straight-chain glucan from sucrose at a high yield using sucrose phosphorylase derived from the genus *Leuconostoc* (*Leuconostoc mesenteroides*) and glucan phosphorylase derived from potato tuber. The SP-GP method of Waldmann et al. is promising in that an inexpensive substrate can be used to produce a straight-chain glucan, but has some problems which require improvement as shown below.

First of all, since a large amount of enzyme is used, the production cost is high and inexpensive production is not possible. To solve this problem, the amount of an enzyme used needs to be reduced or the amylose productivity per unit enzyme needs to be improved by studying the reaction conditions.

One of factors which determine the amount of enzyme used or the amylose productivity per enzyme in the SP-GP method is, for example, the concentration ratio of inorganic phosphate to sucrose, which is a substrate for SP, in a solution at the start of reaction. In the prior art of Waldmann et al., inorganic phosphate having a considerably low concentration compared to the sucrose concentration in a solution at the start of reaction is used, so that glucan is produced at a high yield. In the SP-GP method in which sucrose is first converted to glucose-1-phosphate and then the glucose-1-phosphate is converted to glucan, if high-concentration inorganic phosphate is used, an intermediate, glucose-1-phosphate, accumulates at a high concentration. Therefore, it is considered that the yield of the final product, glucan, is reduced. Therefore, it is considered that a low inorganic phosphate concentration should be adopted in the conventional SP-GP method. Before the present invention, there was no disclosure of what influence a change in the concentration ratio of sucrose to inorganic phosphate in a solution at the start of reaction has on the amount of an enzyme used or the amylose productivity per enzyme, much less prediction of the effect of such an change.

A method in which two types of phosphorylase are combined similarly to the SP-GP method and carbohydrate is synthesized via inorganic phosphate has been reported. For example, Chaen et al. (Journal of Bioscience and Bioengineering, 92 (2001) 177-182) discloses a method for synthesizing kojioligosaccharide from maltose using a combination of maltose phosphorylase and kojibiose phosphorylase. Chaen et al. describes that the lower the inorganic phosphate concentration in a solution at the start of reaction, the higher the yield of the reaction product, i.e., kojioligosaccharide. Thus, it is conventionally considered that in a reaction system in which two phosphorylases are combined, the inorganic phosphate concentration in a solution at the start of reaction is preferably low in order to increase the yield of the final product.

A second factor which determines the amount of enzyme used or the amylose productivity per enzyme in the SP-GP method is reaction temperature. Generally, in enzyme reactions, the higher the reaction temperature, the greater the reaction rate. Therefore, it is desirable that reactions are conducted under high temperature conditions. However, since enzyme proteins are unstable to heating, an actual enzyme reaction is conducted in a temperature range in which the enzyme proteins are not thermally inactivated. In the prior art of Waldmann et al., sucrose phosphorylase derived from the genus *Leuconostoc* was used, and a glucan synthesis reaction was conducted at 37° C. by taking into account the thermal stability of this enzyme. Before the present invention, it had not been disclosed what influence a change in the sucrose concentration of the reaction solution has on the stability of sucrose phosphorylase, and the effect thereof could not be predicted. Further, there had been no disclosure on the thermal stability of sucrose phosphorylase derived from the genus *Streptococcus*. Therefore, it was not possible to predict any effect of utilizing this sucrose phosphorylase in glucan synthesis.

As a second problem, there is an operability problem. Glucan, particularly amylose, ages to become insoluble, resulting in precipitation or formation of a gel. It is well known that the aging rate is dependent on temperature. When reaction temperature is low, an operability problem arises in subsequent stages after the production, such as gelation of amylose solution. Therefore, the reaction temperature is preferably as high as possible. However, in the prior art of Waldmann et al., the reaction temperature at which amylose is produced is problematically as low as 37° C.

Out of glucans, when a straight-chain amylose without a branched structure is to be specifically produced, straight-chain malto-oligosaccharide has to be used as a primer. In the prior art of Waldmann et al., purified maltoheptaose is utilized as straight-chain malto-oligosaccharide. However, purified maltoheptaoseis only distributed as reagent grade and is very expensive. Inexpensive primer candidates include a mixture of malto-oligosaccharide obtained by hydrolyzing starch appropriately. However, it is known that for a number of glucan phosphorylases, only malto-oligosaccharides having a degree of polymerization greater than or equal to that of maltotetraose can be utilized as a primer, but malto-oligosaccharides having a degree of polymerization smaller than or equal to that of maltotriose cannot be utilized as a primer. The malto-oligosaccharide mixture contains maltotriose, maltose and glucose which do not function as a primer in addition to malto-oligosaccharide having a degree of polymerization greater than or equal to that of maltohexaose which can function as a primer. Further, it is known that glucose contained in the malto-oligosaccharide mixture is an inhibitor of sucrose phosphorylase. Thus, whether or not the malto-oligosaccharide mixture containing maltotriose, maltose and glucose incapable of functioning as a primer and glucose which is an inhibitor of sucrose phosphorylase, can function effectively in the SP-GP method had not been disclosed before the present invention, and the effectiveness thereof could not be easily speculated.

In the case of a method of the present invention, a large amount of fructose is secondarily produced along with glucan in the reaction solution after ending an enzyme reaction. Therefore, in the case of industrial glucan production using the method of the present invention, a process for efficiently purifying glucan after a glucan synthesis reaction step is essential. In the prior art of Waldmann et al., when purifying amylose, a method for selectively precipitating amylose using butanol is utilized. However, when amylose is industrially mass produced, a method utilizing an organic solvent is not an excellent method in terms of costs, safety to a human body, and environmental issues. No method using no organic solvent has been disclosed.

DISCLOSURE OF THE INVENTION

The present invention is intended to solve the above-described problems. An objective of the present invention is to provide a method for producing glucan, particularly amylose, in a stable and inexpensive manner under conditions more practical than conventional methods. More specifically, the objective of the present invention is to provide a method for reducing the amount of enzyme required as much as possible and achieving a reaction at higher temperature when producing amylose from sucrose.

Another objective of the present invention is to purify amylose efficiently from a produced amylose solution without using an organic solvent.

The inventors of the present invention have rigorously researched to solve the above-described problems, and eventually found that by setting the maximum value of the ratio of the mole concentration of sucrose to the sum of the mole concentrations of inorganic phosphate and glucose-1-phosphate during a time from the start of a reaction to the end of the reaction, within a certain range, a higher level of productivity than conventional methods can be obtained. Based on this finding, the inventors completed the present invention.

The inventors also found that the heat-resistance of sucrose phosphorylase is increased in the presence of sucrose having at least a certain concentration, so that reaction temperature can be increased; as a result, the amount of enzymes required can be reduced, or the glucan productivity per unit enzyme can be increased; and further the reaction is conducted at high temperature, so that amylose can be produced without aging. Based on this finding, the inventors completed the present invention.

The inventors also found that reaction temperature can be increased by utilizing sucrose phosphorylase derived from the genus *Streptococcus*; as a result, the amount of enzymes required can be reduced, or the glucan productivity per unit enzyme can be increased; and further the reaction is conducted at high temperature, so that amylose can be produced without aging. Based on this finding, the inventors completed the present invention.

The inventors also found that even though a malto-oligosaccharide mixture (particularly one that contains maltotriose, maltose and glucose which cannot function as a primer for a number of glucan phosphorylases and glucose which is an inhibitor of sucrose phosphorylase), rather than purified malto-oligosaccharide is used as a primer for use in the SP-GP method, synthesis of a glucan of interest, particularly amylose, can be conducted without a particular problem. Based on this finding, the inventors completed the present invention.

The present inventors found that fructose can be efficiently removed from a reaction solution by any of the following processes so as to produce glucans, and based on this finding, completed the present invention:

(1) purifying produced glucans without utilizing an organic solvent;

(2) cooling the reaction solution after the reaction to precipitate glucans, and purifying the precipitated glucans by a solid-liquid separation method;

(3) cooling the reaction solution during or after the glucan producing reaction to gel glucans, recovering the gelled glucans, and removing fructose from the gelled glucans by an operation selected from the group consisting of washing with water, freeze-thawing, filtration, squeezing, suction and centrifugation; and (4) removing fructose by membrane fractionation using an ultrafiltration membrane or chromatography after the glucan producing reaction, without precipitating glucans dissolved in water.

A first method of the present invention for producing glucans comprises the step of allowing a reaction solution containing sucrose, a primer, inorganic phosphate or glucose-1-phosphate, sucrose phosphorylase, and glucan phosphorylase to react to produce glucans. The maximum value of the sucrose-phosphate ratio of the reaction solution from the start of the reaction to the end of the reaction is no more than about 17.

In one embodiment, the maximum value may be at least about 0.5 and no more than about 15, preferably at least about 1 and no more than about 10, and more preferably at least about 2 and no more than about 7.

In one embodiment, the glucan may be amylose.

In one embodiment, the sucrose phosphorylase may be derived from a bacterium belonging to the genus *Streptococcus*.

Preferably, the sucrose phosphorylase may be derived from a bacterium belonging to the genus *Streptococcus* selected from the group consisting of *Streptococcus mutans, Streptococcus thermophilus, Streptococcus pneumoniae,* and *Streptococcus mitis*.

In one embodiment, the glucan phosphorylase may be derived from a plant. More preferably, the glucan phosphorylase may be derived from an alga or potato.

In one embodiment, the glucan phosphorylase may be derived from *Thermus aquaticus* or *Bacillus stearothermophilus*.

In one embodiment, both or at least one of the sucrose phosphorylase and the glucan phosphorylase may be produced by a recombinant microorganism.

In one embodiment, both or at least one of the sucrose phosphorylase and the glucan phosphorylase may be immobilized on a carrier.

In one embodiment, the sucrose may be unpurified saccharide.

In one embodiment, the primer may be selected from the group consisting of malto-oligosaccharide, amylose, amylopectin, glycogen, dextrin, pullulan, coupling sugar, starch, and derivatives thereof.

In one embodiment, the malto-oligosaccharide may be a malto-oligosaccharide mixture.

In one embodiment, the malto-oligosaccharide mixture may contain at least one of maltotriose, maltose, and glucose in addition to malto-oligosaccharides having a degree of polymerization greater than or equal to that of maltotetraose.

In one embodiment, the starch may be selected from the group consisting of soluble starch, waxy starch, high amylose starch, starch degraded by a debranching enzyme, starch degraded by phosphorylase, starch partially degraded by hydrolysis, processed starch, and derivatives thereof.

In one embodiment, the method may further comprise the step of purifying the produced glucans without using an organic solvent.

In one embodiment, the method may further comprise the steps of cooling the reaction solution after the reaction to precipitate the glucans, and purifying the precipitated glucan by a solid-liquid separation method.

In one embodiment, the method may further comprise the steps of cooling the reaction solution during or after the glucan producing reaction to gel the glucans, recovering the gelled glucans, and removing fructose from the gelled glucans by an operation selected from the group consisting of washing with water, freeze-thawing, filtration, squeezing, suction and centrifugation.

In one embodiment, the method may further comprise the step of subjecting glucans dissolved in water after the glucan producing reaction to membrane fractionation using an ultrafiltration membrane or chromatography without precipitation to remove fructose. The ultrafiltration membrane may have a molecular weight cutoff of about 30,000. The ultrafiltration membrane may be of a hollow fiber type. The carrier which may be used in the chromatography may be a carrier for gel filtration chromatography, a carrier for ligand exchange chromatography, a carrier for ion exchange chromatography, or a carrier for hydrophobic chromatography.

In one embodiment, the reaction solution may further contain an enzyme selected from the group consisting of debranching enzymes, branching enzymes, 4-α-glucanotransferase, and glycogen debranching enzymes.

A second method of the present invention for producing glucans comprises the step of allowing a reaction solution containing sucrose, a primer, inorganic phosphate or glucose-1-phosphate, sucrose phosphorylase, and glucan phosphorylase to react to produce glucans. The reaction is conducted at a temperature of about 40° C. to about 70° C.

In one embodiment, the reaction temperature may be about 45° C. to about 65° C.

In one embodiment, the sucrose concentration of the reaction solution may be about 5% to about 100% at the start of the reaction, preferably about 8% to about 80%, and more preferably about 15% to about 50%.

In one embodiment, the glucan may be amylose.

In one embodiment, the sucrose phosphorylase may be derived from a bacterium belonging to the genus *Streptococcus* Preferably, the sucrose phosphorylase may be derived from a bacterium belonging to the genus *Streptococcus* selected from the group consisting of *Streptococcus mutans, Streptococcus thermophilus, Streptococcus pneumoniae,* and *Streptococcus mitis*.

In one embodiment, the glucan phosphorylase may be derived from a plant. More preferably, the glucan phosphorylase may be derived from an alga or potato.

In one embodiment, the glucan phosphorylase may be derived from *Thermus aquaticus* or *Bacillus stearothermophilus*.

In one embodiment, both or at least one of the sucrose phosphorylase and the glucan phosphorylase may be produced by a recombinant microorganism.

In one embodiment, both or at least one of the sucrose phosphorylase and the glucan phosphorylase maybe immobilized on a carrier.

In one embodiment, the sucrose may be unpurified saccharide.

In one embodiment, the primer may be selected from the group consisting of malto-oligosaccharide, amylose, amylopectin, glycogen, dextrin, pullulan, coupling sugar, starch, and derivatives thereof.

In one embodiment, the malto-oligosaccharide may be a malto-oligosaccharide mixture.

In one embodiment, the malto-oligosaccharide mixture may contain at least one of maltotriose, maltose, and glucose in addition to malto-oligosaccharides having a degree of polymerization greater than or equal to that of maltotetraose.

In one embodiment, the starch may be selected from the group consisting of soluble starch, waxy starch, high amylose starch, starch degraded by a debranching enzyme, starch degraded by phosphorylase, starch partially degraded by hydrolysis, processed starch, and derivatives thereof.

In one embodiment, the method may further comprise the step of purifying the produced glucans without using an organic solvent.

In one embodiment, the method may further comprise the steps of cooling the reaction solution after the reaction to precipitate the glucans, and purifying the precipitated glucan by a solid-liquid separation method.

In one embodiment, the method may further comprise the steps of cooling the reaction solution during or after the glucan producing reaction to gel the glucans, recovering the gelled glucans, and removing fructose from the gelled glucans by an operation selected from the group consisting of washing with water, freeze-thawing, filtration, squeezing, suction and centrifugation.

In one embodiment, the method may further comprise the step of subjecting glucans dissolved in water after the glucan producing reaction to membrane fractionation using an ultrafiltration membrane or chromatography without precipitation to remove fructose. The ultrafiltration membrane may have a molecular weight cutoff of about 30,000. The ultrafiltration membrane may be of a hollow fiber type. The carrier which may be used in the chromatography may be a carrier for gel filtration chromatography, a carrier for ligand exchange chromatography, a carrier for ion exchange chromatography, or a carrier for hydrophobic chromatography.

In one embodiment, the reaction solution may further contain an enzyme selected from the group consisting of debranching enzymes, branching enzymes, 4-α-glucanotransferase, and glycogen debranching enzymes.

A third method of the present invention for producing glucans comprises the step of allowing a reaction solution containing sucrose, a primer, inorganic phosphate or glucose-1-phosphate, sucrose phosphorylase, and glucan phosphorylase to react to produce glucans. The maximum value of the sucrose-phosphate ratio of the reaction solution from the start of the reaction to the end of the reaction is no more than about 17, and the reaction is conducted at a temperature of about 40° C. to about 70° C.

In one embodiment, the maximum value may be at least about 0.5 and no more than about 15, preferably at least about 1 and no more than about 10, and more preferably at least about 2 and no more than about 7.

In one embodiment, the reaction temperature may be about 45° C. to about 65° C.

In one embodiment, the sucrose concentration of the reaction solution may be about 5% to about 100% at the start of the reaction, preferably about 8% to about 80%, and more preferably about 15% to about 50%.

In one embodiment, the glucan may be amylose.

In one embodiment, the sucrose phosphorylase may be derived from a bacterium belonging to the genus *Streptococcus*. Preferably, the sucrose phosphorylase may be derived from a bacterium belonging to the genus *Streptococcus* selected from the group consisting of *Streptococcus mutans, Streptococcus thermophilus, Streptococcus pneumoniae*, and *Streptococcus mitis*.

In one embodiment, the glucan phosphorylase may be derived from a plant. More preferably, the glucan phosphorylase may be derived from an alga or potato.

In one embodiment, the glucan phosphorylase may be derived from *Thermus aquaticus* or *Bacillus stearothermophilus*.

In one embodiment, both or at least one of the sucrose phosphorylase and the glucan phosphorylase may be produced by a recombinant microorganism.

In one embodiment, both or at least one of the sucrose phosphorylase and the glucan phosphorylase may be immobilized on a carrier.

In one embodiment, the sucrose may be unpurified saccharide.

In one embodiment, the primer may be selected from the group consisting of malto-oligosaccharide, amylose, amylopectin, glycogen, dextrin, pullulan, coupling sugar, starch, and derivatives thereof.

In one embodiment, the malto-oligosaccharide may be a malto-oligosaccharide mixture.

In one embodiment, the malto-oligosaccharide mixture may contain at least one of maltotriose, maltose, and glucose in addition to malto-oligosaccharides having a degree of polymerization greater than or equal to that of maltotetraose.

In one embodiment, the starch may be selected from the group consisting of soluble starch, waxy starch, high amylose starch, starch degraded by a debranching enzyme, starch degraded by phosphorylase, starch partially degraded by hydrolysis, processed starch, and derivatives thereof.

In one embodiment, the method may further comprise the step of purifying the produced glucans without using an organic solvent.

In one embodiment, the method may further comprise the steps of cooling the reaction solution after the reaction to precipitate the glucans, and purifying the precipitated glucan by a solid-liquid separation method.

In one embodiment, the method may further comprise the steps of cooling the reaction solution during or after the glucan producing reaction to gel the glucans, recovering the gelled glucans, and removing fructose from the gelled glucans by an operation selected from the group consisting of washing with water, freeze-thawing, filtration, squeezing, suction and centrifugation.

In one embodiment, the method may further comprise the step of subjecting glucans dissolved in water after the glucan producing reaction to membrane fractionation using an ultrafiltration membrane or chromatography without precipitation to remove fructose. The ultrafiltration membrane may have a molecular weight cutoff of about 30,000. The ultrafiltration membrane may be of a hollow fiber type. The carrier which may be used in the chromatography may be a carrier for gel filtration chromatography, a carrier for ligand exchange chromatography, a carrier for ion exchange chromatography, or a carrier for hydrophobic chromatography.

In one embodiment, the reaction solution may further contain an enzyme selected from the group consisting of debranching enzymes, branching enzymes, 4-α-glucanotransferase, and glycogen debranching enzymes.

A fourth method of the present invention for producing glucans comprises the step of allowing a reaction solution containing sucrose, a primer, inorganic phosphate or glucose-1-phosphate, sucrose phosphorylase, and glucan phosphorylase to react to produce glucans, wherein the sucrose-phosphate ratio of the reaction solution at the start of the reaction is no more than about 17.

In one embodiment, neither inorganic phosphate nor glucose-1-phosphate is further added after starting the reaction.

In one embodiment, the reaction may be conducted at a temperature of about 40° C. to about 70° C.

A fifth method of the present invention for producing glucans comprises the steps of allowing a reaction solution containing sucrose, a primer, inorganic phosphate or glucose-1-phosphate, sucrose phosphorylase, and glucan phosphorylase to start a reaction; further adding sucrose, inorganic phosphate or glucose-1-phosphate to the reaction solution; and further continuing the reaction to produce glucans, wherein the sucrose-phosphate ratio of the reaction solution at the time of finishing the addition step is no more than about 17.

In one embodiment, the reaction may be conducted at a temperature of about 40° C. to about 70° C.

Glucans of the present invention is produced by any of the above-described methods.

BEST MODE FOR CARRYING OUT THE INVENTION

Figure 1:
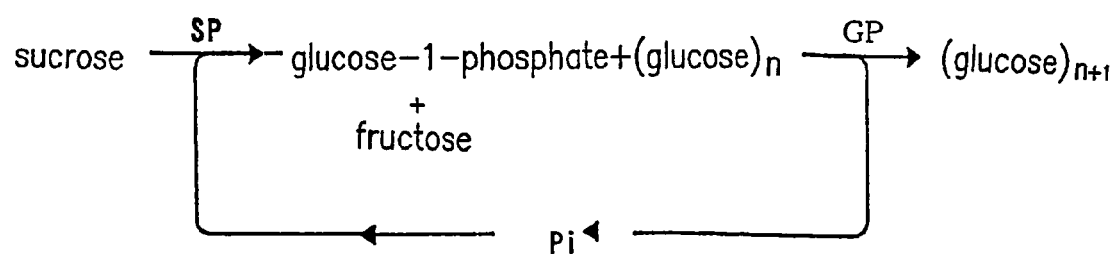
FIG. 1 is a schematic diagram showing a production flow of glucan synthesis from sucrose.

Hereinafter, the present invention will be described in detail.

In the method of the present invention, glucans are produced. In the present specification, "glucan" refers to a saccharide in which the component unit is D-glucose and having at least two saccharide units linked by an α-1,4-glucoside bond. Glucans may be straight-chain, branched or cyclic molecules. Straight-chain glucan and α-1,4-glucan are synonymous. In a straight-chain glucan, saccharide units are linked only by α-1,4-glucoside bonds. Glucans including at least one α-1,6-glucoside bond are branched glucans. Preferably, glucans include a portion of a straight-chain to some extent. Straight-chain glucans without branching are more preferable.

In some cases, glucans having a small number of branches (i.e., α-1,6-glucoside bonds) are preferable. In such cases, the number of branches is representatively 0 to 10,000, preferably 0 to 1000, more preferably 0 to 500, even more preferably 0 to 100, even more preferably 0 to 50, even more preferably 0 to 25, and even more preferably 0.

In the glucans of the present invention, the ratio of the number of α-1,4-glucoside bonds to the number of α-1,6-glucoside bonds where the number of α-1,6-glucoside bonds is 1, is preferably 1 to 10000, more preferably 10 to 5000, even more preferably 50 to 1000, and even more preferably 100 to 500.

α-1,6-glucoside bonds may be distributed in glucans at random or uniformly. It is preferable that in the glucans, straight-chain portions which are at least 5 saccharide units long are present.

The glucans may consist only of D-glucose, or may be a derivative which is modified to an extent that the properties of the glucans are not impaired. Unmodified glucans are preferable.

The glucans have a molecular weight of representatively at least about $8 \times 10^3$, preferably at least about $1 \times 10^4$, more preferably at least about 5×, even more preferably at least about $1 \times 10^5$, and even more preferably at least about $6 \times 10^5$. The glucans have a molecular weight of representatively no more than about $1 \times 10^8$, preferably no more than about $1 \times 10^7$, even more preferably no more than about $5 \times 10^6$, and even more preferably no more than about $1 \times 10^6$.

It is easily understood by those skilled in the art that glucans having a desired molecular weight can be obtained by appropriately setting the amount of a substrate, the amount of an enzyme, a reaction time, and the like used in the production method of the present invention.

<Materials for Producing Glucans>

In the production method of the present invention, for example, sucrose, a primer, inorganic phosphate or glucose-1-phosphate, a buffering agent, sucrose phosphorylase, glucan phosphorylase and a solvent capable of dissolving them are used as major materials. Although all of these materials are usually added at the start of a reaction, any of these materials may be further added in the course of the reaction. In the production method of the present invention, if necessary, an enzyme selected from the group consisting of debranching enzymes, branching enzymes, 4-α-glucanotransferase, and glycogen debranching enzymes can be used. The enzyme selected from the group consisting of debranching enzymes, branching enzymes, 4-α-glucanotransferase, and glycogen debranching enzymes may be added to a reaction solution at the start of the production method of the present invention or in the course of the method, depending on the intended structure of the glucan.

(1) Sucrose:

Sucrose is represented by $C_{12}H_{22}O_{11}$, and is a disaccharide having a molecular weight of about 342. Sucrose is present in any plants capable of photosynthesis. Sucrose may be isolated from plants or chemically synthesized. In terms of cost, sucrose is preferably isolated from plants. Examples of plants containing a large amount of sucrose include sugarcane, sugarbeet, and the like. Sugarcane contains about 20% sucrose in its juice. Sugar beet contains about 10 to 15% sucrose in its juice. Sucrose may be provided as any materials obtained from any stage of the purification process from a juice of a plant containing sucrose to purified saccharide.

Sucrose for use in the method of the present invention is preferably pure. However, sucrose may contain any other contaminants as long as they do not inhibit the effect of sucrose in the present invention.

The concentration of sucrose contained in solution is representatively about 5% to about 100%, preferably about 8% to about 80%, and more preferably about 8% to about 50%. It should be noted that in the present specification, the sucrose concentration is calculated by Weight/Volume, i.e., (the weight of sucrose)×100/(the volume of solution).

If the weight of sucrose is excessively great, unreacted sucrose may be precipitated during the reaction. If the amount of sucrose used is excessively small, the yield may be reduced in a high-temperature reaction.

It should be noted that in the case of the above-described first method, i.e., the maximum value of the sucrose-phosphate ratio in the reaction solution from the start to end of the reaction is no more than about 17, the sucrose concentration is not necessarily limited to the above-described range. Also, in the case of the above-described fourth method, i.e., the sucrose-phosphate ratio in the reaction solution at the start of the reaction is no more than about 17, and in the case of the above-described fifth method, i.e., including a step of further adding sucrose, inorganic phosphate or glucose-1-phosphate to the reaction solution, the sucrose concentration is not necessarily limited to the above-described range. In the present specification, the ratio obtained by dividing the molar concentration of sucrose in reaction solution by the sum of the molar concentrations of inorganic phosphate and glucose-1-phosphate in the reaction solution is referred to as the sucrose-phosphate ratio. In other words:

The sucrose-phosphate ratio=(the molar concentration of sucrose)/(the sum of the molar concentrations of inorganic phosphate and glucose-1-phosphate)

If all of the materials to be reacted are mixed at the start of a reaction and no material is added during the reaction, the sucrose-phosphate ratio is maximal at the start of the reaction.

(2) Primer:

A primer for use in the present invention refers to a molecule which functions as a starting material for glucan synthesis. If a primer has at least one free portion to which a saccharide unit can bind with an α-1,4-glucoside bond, the other portion may be formed by a moiety other than a saccharide. In the method of the present invention, saccharide units are successively linked to the primer with α-1,4-glucoside bonds, resulting in glucan synthesis. Primers include any saccharide to which a saccharide unit can be added by glucan phosphorylase.

Primers can be any starting material for the reaction in the present invention. For example, glucans synthesized by the method of the present invention can be used as a primer to extend an α-1,4-glucoside chain again by the method of the present invention.

A primer may be an α-1,4-glucan including only α-1,4-glucoside bonds, or may be an α-1,4-glucan partially including α-1,6-glucoside bonds. Those skilled in the art may easily select an appropriate primer depending on a desired glucan. In the case of synthesis of straight-chain amylose, it is preferable to use an α-1,4-glucan including only α-1,4-glucoside bonds as a primer, since the straight-chain amylose can be synthesized without using a debranching enzyme or the like.

Examples of primers include malto-oligosaccharides, amylose, amylopectin, glycogen, dextrin, pullulan, coupling sugar, starch and derivatives thereof.

In the present specification, malto-oligosaccharide refers to a substance generated by dehydration-condensation of 2 to 10 glucoses and linked with α-1,4 bonds. Malto-oligosaccharides contain preferably 4 to 10 saccharide units, more preferably 5 to 10 saccharide units, and even more preferably 7 to 10 saccharide units. Examples of malto-oligosaccharides include maltose, maltotriose, maltotetraose, maltopentaose, maltohexaose, maltoheptaose, maltooctaose, maltononaose, maltodecaose, and the like. Preferably, the malto-oligosaccharide is maltotetraose, maltopentaose, maltohexaose, or maltoheptaose. The malto-oligosaccharide may be either a single-ingredient product or a mixture of multiple malto-oligosaccharides. A mixture of malto-oligosaccharides is preferable due to its low cost. In one embodiment, a mixture of malto-oligosaccharides contains at least one of maltotriose, maltose and glucose in addition to a malto-oligosaccharide having a degree of polymerization greater than or equal to that of maltotetraose. Here, "a malto-oligosaccharide having a degree of polymerization greater than or equal to that of maltotetraose" refers to a malto-oligosaccharide having a degree of polymerization of at least four. An oligosaccharide may be either a straight-chain oligosaccharide or a branched oligosaccharide. An oligosaccharide may have a cyclic portion in a molecule thereof. In the present invention, a straight-chain oligosaccharide is preferable.

Amylose is a straight-chain molecule composed of glucose units linked with α-1,4 bonds. Amylose is contained in naturally occurring starch.

Amylopectin is a branched molecule composed of glucose units linked with α-1,4 bonds to which glucose units are linked with α-1,6 bonds. Amylopectin is contained in naturally occurring starch. As amylopectin, for example, waxy corn starch consisting of 100% amylopectin may be used. For example, amylopectin having a degree of polymerization of at least about $1 \times 10^5$ may be used as a raw material.

Glycogen is a type of glucan composed of glucose and having highly-frequent branches. Glycogen is widely distributed as a storage polysaccharide in substantially any cells of animals and plants in the form of granules. Glycogen is present in corn seeds or the like in plants, for example. In glycogen, representatively, an α-1,4-bond sugar chain having an average degree of polymerization of 12 to 18 is linked to an α-1,4-bond sugar chain of glucose at a rate of about one chain per three glucose units with α-1,6 bonds. Branches linked with α-1,6 bonds are similarly linked to the α-1,4-bond sugar chain of glucose with α-1,6 bonds. Therefore, glycogen has a network structure.

The molecular weight of glycogen is representatively about $1 \times 10^5$ to about $1 \times 10^8$, and preferably about $1 \times 10^6$ to about $1 \times 10^7$.

Pullulan is a glucan having a molecular weight of about 100,000 to about 300,000 (e.g., about 200,000), in which maltotrioses are regularly linked in a stepwise manner with α-1,6 bonds. For example, pullulan is produced by culturing *Aureobasidium pullulans* using starch as a raw material. Pullulan may be obtained from Hayashibara Shoji, Inc., for example.

Coupling sugar is a mixture in which sucrose, glucosyl sucrose and maltosyl sucrose are major components. Coupling sugar is produced by allowing a cyclodextrin glucanotransferase, which is produced by *Bacillus megaterium* or the like, to act on a mixed solution of sucrose and starch, for example. Coupling sugar may be obtained from Hayashibara Shoji, Inc., for example.

Starch is a mixture of amylose and amylopectin. As starch, any starch which is usually commercially available may be used. The ratio of amylose to amylopectin contained in starch varies depending on the type of plant which produces the starch. The majority of starch contained in waxy rice, waxy corn, and the like is amylopectin. On the other hand, starch consisting only of amylose, with no amylopectin cannot be obtained from normal plants.

Starch is divided into naturally occurring starch, starch degradation products, and processed starch.

Naturally occurring starch is divided, by the raw material from which it is derived, into tuber starch and cereal starch. Examples of tuber starch include potato starch, tapioca starch, sweet potato starch, kudzu starch, bracken starch, and the like. Examples of cereal starch include corn starch, wheat starch, rice starch, and the like. An example of naturally occurring starch is high-amylose starch (e.g., high-amylose corn starch) which has an increased amylose content as high as 50% to 70% as a result of breeding of plants producing starch. Another example of naturally occurring starch is waxy starch which does not contain amylose as a result of breeding of plants producing starch.

Soluble starch refers to water soluble starch obtained by subjecting naturally occurring starch to various treatments.

Processed starch is starch obtained by subjecting naturally occurring starch to a treatment, such as hydrolysis, esterification, gelatinization, or the like, to confer a property for better ease of utilization. A wide variety of processed starch can be available which have various combinations of properties, such as, for example, temperature at which gelatinization starts, the viscosity of starch paste, the transparency of starch paste, aging stability, and the like. There are various types of processed starch. An example of such starch is starch which is obtained by immersing starch granules in an acid at a temperature of no more than the gelatinization temperature of the starch so that starch molecules are cleaved but starch granules are not broken.

Starch degradation products are oligosaccharides or polysaccharides obtained by subjecting starch to treatment, such as enzyme treatment, hydrolysis, or the like, which have a lower molecular weight than before the treatment. Examples of starch degradation products include starch degraded by a debranching enzyme, starch degraded by phosphorylase and starch partially degraded by hydrolysis.

Starch degraded by a debranching enzyme is obtained by allowing a debranching enzyme to act on starch. By changing the action time of the debranching enzyme to various extents, starch degraded by a debranching enzyme in which branching portions (i.e., α-1,6-glucoside bond) are cleaved to an arbitrary extent can be obtained. Examples of the starch degraded by a debranching enzyme include degradation products of 4 to 10,000 saccharide units having 1 to 20 α-1,6-glucoside bonds, degradation products of 3 to 500 saccharide units without a α-1,6-glucoside bond, maltooligosaccharide, and amylose. In the case of the starch degraded by a debranching enzyme, the distribution of the molecular weight of the resultant degradation products may vary depending on the type of degraded starch. The starch degraded by a debranching enzyme may be a mixture of sugar chains having various lengths.

Starch degraded by phosphorylase is obtained by allowing glucan phosphorylase (also referred to as phosphorylase) to act on starch. Glucan phosphorylase transfers a glucose residue from a non-reducing terminal of starch to other substrates on a saccharide-unit-by-saccharide-unit basis. Glucan phosphorylase cannot cleave a α-1,6-glucoside bond. Therefore, if glucan phosphorylase is allowed to act on starch for a sufficiently long time, a degradation product in which cleavage is ended at an α-1,6-glucoside bond is obtained. In the present invention, the number of saccharide units contained in starch degraded by phosphorylase is preferably about 10 to about 100,000, more preferably about 50 to about 50,000, and even more preferably about 100 to about 10,000. In the case of the starch degraded by phosphorylase, the distribution of the molecular weight of the degradation products may vary depending on the type of starch to be degraded. The starch degraded by phosphorylase may be a mixture of sugar chains having various lengths.

Dextrin and starch partially degraded by hydrolysis refer to degradation products obtained by degrading starch partially by the action of an acid, an alkali, an enzyme, or the like. In the present invention, the number of saccharide units contained in dextrin and starch partially degraded by hydrolysis is preferably about 10 to about 10,000, more preferably about 50 to about 50,000, and even more preferably about 100 to about 10,000. In the case of dextrin and starch partially degraded by hydrolysis, the distribution of the molecular weight of the resultant degradation products may vary depending on the type of starch to be degraded. Dextrin and the starch partially degraded by hydrolysis may be a mixture of sugar chains having various lengths.

The starch is preferably selected from the group consisting of soluble starch, waxy starch, high-amylose starch, starch degraded by a debranching enzyme, starch degraded by phosphorylase, starch partially degraded by hydrolysis, processed starch, and derivatives thereof.

In the method of the present invention, derivatives of the above-described various saccharides may be used as a primer. For example, derivatives in which at least one alcoholic hydroxyl group of the above-described saccharides have been hydroxyalkylated, alkylated, acetylated, carboxymethylated, sulfated, phosphorylated, or like may be used. Further, a mixture including at least two of the above-described derivatives may be used as a raw material.

(3) Inorganic Phosphate or Glucose-1-phosphate:

In the present specification, inorganic phosphate refers to a substance capable of providing a phosphate substrate in a SP reaction. Here, a phosphate substrate refers to a substance which is a raw material for a phosphate moiety of glucose-1-phosphate. In sucrose phosphorolysis catalyzed by sucrose phosphorylase, inorganic phosphate is believed to act as a substrate in the form of a phosphate ion. In the art, such a substrate is conventionally called inorganic phosphate, so that in the present specification, this substrate is referred to as inorganic phosphate. Inorganic phosphate includes phosphoric acid and inorganic salts of phosphoric acid. Typically, inorganic phosphate is used in water containing cations, such as alkali metal ions. In this case, phosphoric acid, phosphate salts, and phosphate ions are brought into equilibrium, so that it is difficult to distinguish phosphoric acid from phosphate salts. Therefore, for convenience, phosphoric acid and phosphate salts are referred to as inorganic phosphate. In the present invention, inorganic phosphate is preferably any metal salt of phosphoric acid, and more preferably any alkali metal salts of phosphoric acid. Preferable specific examples of inorganic phosphate include sodium dihydrogen phosphate, disodium hydrogen phosphate, trisodium phosphate, potassium dihydrogen phosphate, dipotassium hydrogen phosphate, tripotassium phosphate, phosphoric acid ($H_3PO_4$), ammonium dihydrogen phosphate, diammonium hydrogen phosphate, and the like.

Only one type or a plurality of types of inorganic phosphate may be contained in a SP-GP reaction system at the start of a reaction.

Inorganic phosphate may be provided, for example, by adding a degradation product of a condensed phosphoric acid, such as polyphosphate (e.g., pyrophosphoric acid, triphosphoric acid and tetraphosphoric acid) or a salt thereof, which was degraded by a physical, chemical, or enzymatic reaction, to a reaction solution.

In the present specification, glucose-1-phosphate refers to glucose-1-phosphate ($C_6H_{13}O_9P$) and salts thereof. Glucose-1-phosphate is preferably any metal salt of glucose-1-phosphate ($C_6H_{13}O_9P$) in a narrow sense, and more preferably any alkali metal salt of glucose-1-phosphate ($C_6H_{13}O_9P$). Preferable specific examples of glucose-1-phosphate include disodium glucose-1-phosphate, dipotassium glucose-1-phosphate, glucose-1-phosphate ($C_6H_{13}O_9P$), and the like. In the present specification, glucose-1-phosphate without a parenthesized chemical formula represents glucose-1-phosphate in a broad sense, i.e., glucose-1-phosphate ($C_6H_{13}O_9P$) in a narrow sense and salts thereof.

Only one type or a plurality of types of glucose-1-phosphate may be contained in a SP-GP reaction system at the start of a reaction.

In the method of the present invention, the ratio of phosphate and glucose-1-phosphate in a reaction solution at the start of the reaction may be any arbitrary ratio.

The sum of the molar concentrations of inorganic phosphate and glucose-1-phosphate contained in a reaction solution is representatively about 1 mM to about 1000 mM, preferably about 10 mM to about 500 mM, and more preferably about 20 mM to about 250 mM. Each of the molar concentrations of inorganic phosphate and glucose-1-phosphate is adjusted so that the maximum value of the sucrose-phosphate ratio in a reaction solution from the start of a reaction to the end of the reaction is representatively no more than about 17, preferably at least about 0.5 and no more than about 15, more preferably at least about 1 and no more than about 10, and even more preferably at least about 2 and no more than about 7. In the case of the above-described fourth method of the invention, each of the molar concentrations of inorganic phosphate and glucose-1-phosphate is adjusted so that sucrose-phosphate ratio of the reaction solution at the start of the reaction is in the above-described range. In the case of the above-described fifth method of the invention, each of the molar concentrations of inorganic phosphate and glucose-1-phosphate is adjusted so that sucrose-phosphate ratio of the reaction solution at the time of finishing the step of further adding sucrose, inorganic phosphate or glucose-1-phosphate to the reaction solution is in the above-described range. If the amount of inorganic phosphate and glucose-1-phosphate is excessively great, the glucan yield may be reduced. If such an amount to be used is excessively small, it may takes a long time to synthesize glucans.

The inorganic phosphate content of a SP-GP reaction system may be quantitated by a method described below in Section 1.4. The glucose-1-phosphate content of a SP-GP reaction system may be quantitated by a method described below in Section 1.3. In cases where a phosphor-containing substance which is not involved in the reaction is not used, the total content of inorganic phosphate and glucose-1-phosphate may be determined by atomic absorption spectroscopy.

It should be noted that in the case of the above-described second method, i.e., when a reaction is conducted at a reaction temperature of about 40° C. to about 70° C., the above-described maximum value is not necessarily no more than about 17.

(4) Sucrose Phosphorylase (EC. 2. 4. 1. 7):

In the present specification, "sucrose phosphorylase" refers to any enzyme which performs phosphorolysis by transferring an α-glycosyl group of sucrose to a phosphate group. A reaction catalyzed by sucrose phosphorylase is represented by the following formula:

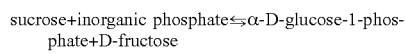

sucrose+inorganic phosphate⇌α-D-glucose-1-phosphate+D-fructose

Sucrose phosphorylase is contained in various organisms in nature. Examples of organisms producing sucrose phosphorylase include, but are not limited to, bacteria of the genus *Streptococcus* (e.g., *Streptococcus thermophilus*, *Streptococcus mutans*, *Streptococcus pneumoniae*, and *Streptococcus mitis*), *Leuconostoc mesenteroides*, *Pseudomonas* sp., *Clostridium* sp., *Pullularia pullulans*, *Acetobacter xylinum*, *Agrobacterium* sp., *Synecococcus* sp., *E. coli*, *Listeria monocytogenes*, *Bifidobacterium adolescentis*, *Bifidobacterium adolescentis*, *Aspergillus niger*, *Monilia sitophila*, *Sclerotinea escerotiorum*, and *Chlamydomonas* sp.

Sucrose phosphorylase may be derived from any organisms producing sucrose phosphorylase. Sucrose phosphorylase preferably has heat-resistance to some extent. The higher the heat-resistance of sucrose phosphorylase which is present alone, the more preferable the sucrose phosphorylase. For example, a sucrose phosphorylase is preferable in which when the sucrose phosphorylase is heated in the presence of 4% sucrose at 55° C. for 30 minutes, retains at least 50% of the activity of the sucrose phosphorylase as compared to the activity of the sucrose phosphorylase before the heating. Sucrose phosphorylase is preferably derived from bacteria of the genus *Streptococcus*, even more preferably derived from *Streptococcus mutans*, *Streptococcus thermophilus*, *Streptococcus pneumoniae*, or *Streptococcus mitis*.

In the present specification, an enzyme being "derived from" a certain organism not only means direct isolation from the organism, but also refers to that the enzyme is obtained by utilization of the organism in some manner. For example, when a gene encoding the enzyme obtained from the organism is introduced into *E. coli* and the enzyme is isolated from the *E. coli*, the enzyme is said to be "derived" from the organism.

Sucrose phosphorylase for use in the present invention may be isolated directly from an organism as described above which exists in nature and produces sucrose phosphorylase. Sucrose phosphorylase for use in the present invention may be isolated from a microorganism (e.g., bacteria, fungi, and the like) which has been obtained by gene recombination using a gene encoding sucrose phosphorylase isolated from the above-described organisms.

Sucrose phosphorylase for use in the method of the present invention may be prepared as described below, for example. Initially, a microorganism (e.g., bacteria, fungi, and the like) producing sucrose phosphorylase is cultured. This microorganism may be a microorganism which directly produces sucrose phosphorylase. Alternatively, a gene encoding sucrose phosphorylase is cloned, and using the resultant gene, a microorganism (e.g., bacteria, fungi, and the like) useful for expression of sucrose phosphorylase is subjected to gene recombination to obtain a recombinant microorganism. Sucrose phosphorylase may be obtained from the resultant microorganism.

A microorganism for use in gene recombination using the sucrose phosphorylase gene may be easily selected by considering various conditions, such as the ease of expression of sucrose phosphorylase, the ease of cultivation, the growth rate, the safety, and the like. It is preferable that sucrose phosphorylase does not contain amylase as contaminant. Therefore, it is preferable that a microorganism (e.g., bacteria, fungi, and the like) which produces or expresses no or a low level of amylase is used in gene recombination. For gene recombination of sucrose phosphorylase, mesophiles, such as *E. coli* or *Bacillus subtilis*, are preferably used. Sucrose phosphorylase produced by a microorganism (e.g., bacteria, fungi, and the like), which produces or expresses no or a low level of amylase, contains substantially no amylase, and therefore is preferable for use in the method of the present invention.

Gene recombination of a microorganism (e.g., bacteria, fungi, and the like) using cloned genes may be conducted by a method well known to those skilled in the art. When a cloned gene is used, the gene is preferably operably-linked to a constitutive promoter or an inducible promoter. "Operably-linked" indicates that a promoter and a gene are linked together so that expression of the gene is controlled by the promoter. When an inducible promoter is used, culture is preferably conducted under induction conditions. Various inducible promoters are known to those skilled in the art.

For cloned genes, base sequences encoding a signal peptide may be linked to the genes in order to secrete the produced sucrose phosphorylase outside the bacterial cell. Base sequences encoding a signal peptide are known to those skilled in the art.

Those skilled in the art can appropriately determine the conditions for culturing a microorganism (e.g., bacteria, fungi, and the like) in order to produce sucrose phosphorylase. Appropriate media for culturing a microorganism, the appropriate conditions for inducing each inducible promoter and the like are known to those skilled in the art.

After an appropriate time of culturing, sucrose phosphorylase is recovered from the culture. When the produced sucrose phosphorylase is secreted outside the bacterial cell, the bacterial cell can be removed by centrifugation to obtain sucrose phosphorylase in the supernatant. When sucrose phosphorylase produced inside the bacterial cell is not secreted outside the bacterial cell, the microorganisms are destroyed by sonication, mechanical destruction, chemical destruction, or the like to obtain destroyed bacterial cell solution.

In the method of the present invention, the destroyed bacterial cell solution may be used without purification. Thereafter, the destroyed bacterial cell solution may be centrifuged to remove the debris of the bacterial cell, thereby obtaining the supernatant. The resultant supernatant can be subjected to a well-known method including ammonium sulfate or ethanol precipitation, acid extraction, anion- or cation-exchange chromatography, phosphocellulose chromatography, hydrophobic interaction chromatography, affinity chromatography, hydroxylapatite chromatography, and lectin chromatography to recover the enzyme of the present invention. The recovered product may be purified if necessary.

In a preferred embodiment, sucrose phosphorylase may be heated in an arbitrary stage of a purification process in the presence of sucrose (representatively about 4% to about 30%, preferably about 8% to about 30%, and more preferably about 8% to about 25%). The temperature of a solution in this heating process is preferably such that when this solution is heated for 30 minutes, at least 50% and more preferably at least 80% of the activity of sucrose phosphorylase is retained as compared to the activity of sucrose phosphorylase contained in the solution before the heating. Such a temperature is preferably about 50° C. to about 80° C., and more preferably about 55° C. to about 70° C. For example, in the case of sucrose phosphorylase derived from *S. mutans*, the reaction temperature is preferably about 50° C. to about 60° C. When heating is conducted, the time for heating may be arbitrarily determined by considering the reaction temperature as long as the activity of sucrose phosphorylase is not significantly impaired. The heating time is representatively about 10 minutes to about 90 minutes, and more preferably about 30 minutes to about 60 minutes.

The amount of sucrose phosphorylase contained in a solution at the start of a reaction is representatively about 0.05 to 1,000 U/g sucrose, preferably about 0.1 to 500 U/g sucrose, and more preferably about 0.5 to 100 U/g sucrose relative to sucrose in the solution at the start of the reaction. When the weight of sucrose phosphorylase is excessively great, enzymes denatured in a reaction may be likely to aggregate. When the amount to be used is excessively small, the glucan yield may be reduced.

Sucrose phosphorylase may either be purified or not be purified. Sucrose phosphorylase may either be immobilized or not be immobilized. Sucrose phosphorylase is preferably immobilized. As a method for immobilization, a carrier binding method (e.g., a covalent binding method, an ionic binding method, or a physical adsorption method), a cross-linking method, an entrapment method (lattice type or microcapsule type) or the like, which are well known to those skilled in the art, may be used. Sucrose phosphorylase is preferably immobilized on a carrier.

(5) Glucan Phosphorylase (EC. 2. 4. 1. 1):

Glucan phosphorylase is a generic term for enzymes which catalyze phosphorolysis of α-1,4-glucans, and are also called phosphorylase, starch phosphorylase, glycogen phosphorylase, maltodextrin phosphorylase, or the like. Glucan phosphorylase can also catalyze an α-1,4-glucan synthesis reaction which is the reverse reaction relative to phosphorolysis. In which direction a reaction proceeds depends on the amount of substrate. In an organism, where the amount of inorganic phosphate is abundant, glucan phosphorylase causes a reaction to proceed in the phosphorolysis direction. In the method of the present invention, since inorganic phosphate is used in phosphorolysis of sucrose and thus the amount of inorganic phosphate in a reaction solution is small, the reaction proceeds in the α-1,4 glucan synthesis direction.

Glucan phosphorylase is believed to be universally present in various plants, animals, and microorganisms which can store starch or glycogen.

Examples of plants producing glucan phosphorylase include algae, tuber vegetables (e.g., potatoes, sweet potatoes, yam, aroid, cassaya, and the like), vegetables (e.g., cabbage, spinach, and the like), cereals (e.g., maize, rice, wheat, barley, rye, foxtail millet, and the like), beans (e.g., pea, soybean, adzuki bean, uzura bean, and the like), and the like.

Examples of animals which produce glucan phosphorylase include mammals (e.g., humans, rabbits, rats, pigs, and the like), and the like.

Examples of microorganisms which produce glucan phosphorylase include *Thermus aquaticus, Bacillus stearothermophilus, Deinococcus radiodurans, Thermococcus litoralis, Streptomyces coelicolor, Pyrococcus horikoshi, Mycobacterium tuberculosis, Thermotoga maritima, Aquifex aeolicus, Methanococcus jannaschii, Pseudomonas aeruginosa, Chlamydia pneumoniae, Chlorella vulgaris, Agrobacterium tumefaciens, Clostridium pasteurianum, Klebsiella pneumoniae, Synecococcus* sp., *Synechocystis* sp., *E. coli, Neurospora crassa, Saccharomyces cerevisiae, Chlamydomonas* sp., and the like. Organisms which produce glucan phosphorylase are not limited to these.

Glucan phosphorylase for use in the present invention is preferably derived from potato, *Thermus aquaticus*, or *Bacillus stearothermophilus*, and more preferably potato. Preferably, glucan phosphorylase used in the present invention has a high optimal reaction temperature. For example, glucan phosphorylase having a high optimal reaction temperature may be derived from extremely thermophilic bacteria.

Glucan phosphorylase for use in the present invention may be isolated directly from animals, plants, and microorganisms as described above, which are present in nature and produce glucan phosphorylase.

Glucan phosphorylase for use in the present invention may be isolated from microorganisms (e.g., bacteria, fungi, and the like) which has been obtained by gene recombination using a gene encoding glucan phosphorylase isolated from the animals, plants, or microorganisms.

Glucan phosphorylase may be obtained from recombinant microorganisms in a manner similar to that of sucrose phosphorylase as described above.

Similar to the above-described sucrose phosphorylase, a microorganism (e.g., bacteria, fungi, and the like) for use in gene recombination may be easily selected by considering various conditions, such as the ease of expression of glucan phosphorylase, the ease of cultivation, the growth rate, the safety, and the like. It is preferable that glucan phosphorylase does not contain amylase as contaminant. Therefore, it is preferable that a microorganism (e.g., bacteria, fungi, and the like) which produces or expresses no or a low level of amylase is used in gene recombination. For gene recombination of glucan phosphorylase, mesophiles, such as *E. coli* or *Bacillus subtilis*, is preferably used. Glucan phosphorylase produced by a microorganism (e.g., bacteria, fungi, and the like), which produces or expresses no or a low level of amylase, contains substantially no amylase, and therefore is preferable for use in the method of the present invention.

Production and purification of glucan phosphorylase obtained by gene recombination can be conducted in a manner similar to that for the above-described sucrose phosphorylase.

The amount of glucan phosphorylase contained in a solution at the start of reaction is representatively about 0.05 to 1,000 U/g sucrose, preferably about 0.1 to 500 U/g sucrose, and more preferably about 0.5 to 100 U/g sucrose relative to sucrose in a solution at the start of reaction. If the weight of glucan phosphorylase is excessively great, the enzyme denatured in a reaction may be likely to aggregate. When the amount to be used is excessively small, the glucan yield may be reduced.

Glucan phosphorylase may either be purified or not be purified. Glucan phosphorylase may either be immobilized or not be immobilized. Glucan phosphorylase is preferably immobilized. As a method for immobilization, a carrier binding method (e.g., a covalent binding method, an ionic binding method, or a physical adsorption method), a cross-linking method, an entrapment method (lattice type or microcapsule type) or the like, which are well known to those skilled in the art, may be used. Glucan phosphorylase is preferably immobilized on a carrier. Glucan phosphorylase may also be immobilized on the same carrier as that for sucrose phosphorylase, or on another carrier, and preferably on the same carrier.

(6) Debranching Enzyme:

In the method of the present invention, when branches are generated in products, such as when a starting material containing α-1,6-glucoside bonds is used, a debranching enzyme can be used if necessary.

Debranching enzymes which can be used in the present invention are enzymes capable of cleaving a α-1,6-glucoside bond. The debranching enzymes are divided into two categories, i.e., isoamylase (EC 3.2.1.68) which acts well on both amylopectin and glycogen, and α-dextrin endo-1,6-α-glucosidase (also referred to as pullulanase) (EC 3.2.1.41) which acts on amylopectin, glycogen and pullulan.

Debranching enzymes are present in microorganisms, bacteria, and plants. Examples of microorganisms producing a debranching enzyme include *Saccharomyces cerevisiae* and *Chlamydomonas* sp. Examples of bacteria producing a debranching enzyme include *Bacillus brevis, Bacillus acidopullulyticus, Bacillus macerans, Bacillus stearothermophilus, Bacillus circulans, Thermus aquaticus, Klebsiella pneumoniae, Thermoactinomyces thalpophilus, Thermoanaerobacter ethanolicus, Pseudomonas amyloderamosa*, and the like. Examples of plants producing a debranching enzyme include potato, sweet potato, maize, rice, wheat, barley, oat, sugarbeet, and the like. Organisms producing a debranching enzyme are not limited to these.

A debranching enzyme which can be used in the present invention is preferable derived from *Klebsiella pneumoniae, Bacillus brevis, Bacillus acidopullulyticus*, or *Pseudomonas amyloderamosa*, and more preferably *Klebsiella pneumoniae*, or *Pseudomonas amyloderamosa*. Preferably, the debranching enzyme used in the present invention has a high optimal reaction temperature. For example, the debranching enzyme having a high optimal reaction temperature may be derived from extremely thermophilic bacteria.

A debranching enzyme which can be used in the present invention may be isolated directly from microorganisms, bacteria, and plants as described above, which are present in nature and produce a debranching enzyme.

A debranching enzyme which can be used in the present invention may be isolated from a microorganism (e.g., bacteria, fungi, and the like) which has been obtained by gene recombination using a gene encoding the debranching enzyme isolated from the microorganisms, bacteria, and plants.

A debranching enzyme maybe obtained from recombinant microorganisms in a manner similar to that of sucrose phosphorylase as described above.

Similar to the above-described sucrose phosphorylase, a microorganism (e.g., bacteria, fungi, and the like) used in gene recombination may be easily selected by considering various conditions, such as the ease of expression of a debranching enzyme, the ease of cultivation, the growth rate, the safety, and the like. It is preferable that a debranching enzyme does not contain amylase as contaminant. Therefore, it is preferable that a microorganism (e.g., bacteria, fungi, and the like) which produces or expresses no or a low level of amylase is used in gene recombination. For gene recombination of a debranching enzyme, mesophiles, such as *E. coli* or *Bacillus subtilis*, are preferably used. A debranching enzyme produced by a microorganism (e.g., bacteria, fungi, and the like), which produces or expresses no or a low level of amylase, contains substantially no amylase, and therefore is preferable for use in the method of the present invention.

Production and purification of a debranching enzyme obtained by gene recombination can be conducted in a manner similar to that for the above-described sucrose phosphorylase.

The amount of a debranching enzyme contained in a solution at the start of reaction is representatively about 0.05 to 1,000 U/g sucrose, preferably about 0.1 to 500 U/g sucrose, and more preferably about 0.5 to 100 U/g sucrose relative to sucrose in a solution at the start of the reaction. If the weight of a debranching enzyme is excessively great, the enzyme denatured in a reaction may be likely to aggregate. When the amount to be used is excessively small, the glucan yield may be reduced.

A debranching enzyme may either be purified or not be purified. A debranching enzyme may either be immobilized or not be immobilized. A debranching enzyme is preferably immobilized. As a method for immobilization, a carrier binding method (e.g., a covalent binding method, an ionic binding method, or a physical adsorption method), a cross-linking method, an entrapment method (lattice type or microcapsule type) or the like, which are well known to those skilled in the art, may be used. A debranching enzyme is preferably immobilized on a carrier. A debranching enzyme may also be immobilized on the same carrier as that for at least one of sucrose phosphorylase and glucan phosphorylase, or on another carrier, and preferably on the same carrier as that both for sucrose phosphorylase and glucan phosphorylase.

(7) Branching Enzyme (EC.2.4.1.18):

In the method of the present invention, when it is desired that branches are generated in a product, a branching enzyme can be used if necessary.

A branching enzyme which can be used in the present invention is an enzyme which can transfer a portion of an α-1,4-glucan chain to position 6 of a glucose residue in the α-1,4-glucan chain to produce a branch. A branching enzyme is also called a 1,4-α-glucan branching enzyme, a branch-producing enzyme, or a Q enzyme.

A branching enzyme is present in microorganisms, animals, and plants. Examples of microorganisms producing a branching enzyme include *Bacillus stearothermophilus, Bacillus subtilis, Bacillus caldolyticus, Bacillus licheniformis, Bacillus amyloliquefaciens, Bacillus coagulans, Bacillus caldovelox, Bacillus thermocatenulatus, Bacillus smithii, Bacillus megaterium, Bacillus brevis,* Alkalophillic *Bacillus* sp., *Streptomyces coelicolor, Aquifex aeolicus, Synechosystis* sp., *E. coli, Agrobacterium tumefaciens, Thermus aquaticus, Rhodothermus obamensis, Neurospora crassa,* yeast, and the like. Examples of animals producing a branching enzyme include mammals, such as humans, rabbits, rats, pigs, and the like. Examples of plants producing a branching enzyme include algae, tuber vegetables (e.g., potatoes, sweet potatoes, yam, aroid, cassaya, and the like), vegetables (e.g., spinach, and the like), cereals (e.g., maize, rice, wheat, barley, rye, foxtail millet, and the like), beans (e.g., pea, soybean, adzuki bean, uzura bean, and the like), and the like. Organisms producing a branching enzyme are not limited to these.

A branching enzyme which can be used in the present invention is preferably derived from potato, *Bacillus stearothermophilus,* or *Aquifex aeolicus,* and more preferably *Bacillus stearothermophilus* or *Aquifex aeolicus.* Preferably, a branching enzyme used in the present invention has a high optimal reaction temperature. For example, a branching enzyme having a high optimal reaction temperature may be derived from extremely thermophilic bacteria.

A branching enzyme which can be used in the present invention may be isolated directly from microorganisms, animals, and plants as described above, which are present in nature and produce a branching enzyme.

A branching enzyme which can be used in the present invention may be isolated from a microorganism (e.g., bacteria, fungi, and the like) which has been obtained by gene recombination using a gene encoding the branching enzyme isolated from the microorganisms, animals, and plants.

A branching enzyme may be obtained from recombinant microorganisms in a manner similar to that of sucrose phosphorylase as described above.

Similar to the above-described sucrose phosphorylase, a microorganism (e.g., bacteria, fungi, and the like) used in gene recombination may be easily selected by considering various conditions, such as the ease of expression of a branching enzyme, the ease of cultivation, the growth rate, the safety, and the like. It is preferable that a branching enzyme does not contain amylase as contaminant. Therefore, it is preferable that a microorganism (e.g., bacteria, fungi, and the like) which produces or expresses no or a low level of amylase is used in gene recombination. For gene recombination of a branching enzyme, mesophiles, such as *E. coli* or *Bacillus subtilis,* are preferably used. A branching enzyme produced by a microorganism (e.g., bacteria, fungi, and the like), which produces or expresses no or a low level of amylase, contains substantially no amylase, and therefore is preferable for use in the method of the present invention.

Production and purification of a branching enzyme obtained by gene recombination can be conducted in a manner similar to that for the above-described sucrose phosphorylase.

The amount of a branching enzyme contained in a solution at the start of the reaction is representatively about 10 to about 100,000 U/g sucrose, preferably about 100 to about 50,000 U/g sucrose, and more preferably about 1,000 to about 10,000 U/g sucrose relative to sucrose in a solution at the start of the reaction. If the weight of a branching enzyme is excessively great, the enzyme denatured in a reaction may be likely to aggregate. When the amount to be used is excessively small, the glucan yield may be reduced.

A branching enzyme may either be purified or not be purified. A branching enzyme may either be immobilized or not be immobilized. A branching enzyme is preferably immobilized. As a method for immobilization, a carrier binding method (e.g., a covalent binding method, an ionic binding method, or a physical adsorption method), a cross-linking method, an entrapment method (lattice type or microcapsule type) or the like, which are well known to those skilled in the art, may be used. A branching enzyme is preferably immobilized on a carrier. A branching enzyme may also be immobilized on the same carrier as that for at least one of sucrose phosphorylase and glucan phosphorylase, or on another carrier, and preferably on the same carrier as that for both sucrose phosphorylase and glucan phosphorylase.

(8) 4-α-glucanotransferase (EC.2.4.1.25)

In the method of the present invention, when a cyclic structure is to be generated in a product, 4-α-glucanotransferase can be used if necessary.

A 4-α-glucanotransferase which may be used in the present invention is an enzyme which is also called disproportionating enzyme, D-enzyme, amylomaltase, disproportionation enzyme, and the like, and can catalyze saccharide transfer reaction (disproportionation reaction) of malto-oligosaccharides. A 4-α-glucanotransferase is an enzyme which transfers a glycosyl group, or a maltosyl or maltooligosyl unit from a non-reducing terminal of a donor molecule to a non-reducing terminal of an acceptor molecule. Therefore, the enzyme reaction leads to disproportionation of the degree of polymerization of the initially provided malto-oligosaccharides. When the donor molecule is the same as the acceptor molecule, intramolecular transfer occurs, resulting in a product having a cyclic structure.

4-α-glucanotransferases are present in microorganisms and plants. Examples of microorganisms producing 4-α-glucanotransferase include *Aquifex aeolicus, Streptococcus pneumoniae, Clostridium butylicum, Deinococcus radiodurans, Haemophilus influenzae, Mycobacterium tuberculosis, Thermococcus litralis, Thermotoga maritima, Thermotoga neapolitana, Chlamydia psittaci, Pyrococcus* sp., *Dictyoglomus thermophilum, Borrelia burgdorferi, Synechosystis* sp., *E. coli, Thermus aquaticus,* and the like. Examples of plants producing 4-α-glucanotransferase include tuber vegetables (e.g., potato, sweet potato, yam, cassaya, and the like), cereals (e.g., maize, rice, wheat, and the like), beans (e.g., pea, soy bean, and the like), and the like. Organisms producing 4-α-glucanotransferase are not limited to these.

4-α-glucanotransferase which can be used in the present invention is preferably derived from potato, *Thermus aquaticus,* or *Thermococcus litralis,* and more preferably potato or *Thermus aquaticus.* Preferably, 4-α-glucanotransferase used in the present invention has a high optimal reaction temperature. For example, 4-α-glucanotransferase having a high optimal reaction temperature may be derived from extremely thermophilic bacteria.

4-α-glucanotransferase which can be used in the present invention may be isolated directly from microorganisms and plants as described above, which are present in nature and produce 4-α-glucanotransferase.

4-α-glucanotransferase which can be used in the present invention may be isolated from a microorganism (e.g., bacteria, fungi, and the like) which has been obtained by gene recombination using a gene encoding 4-α-glucanotransferase isolated from the microorganisms and plants.

4-α-glucanotransferase may be obtained from recombinant microorganisms in a manner similar to that of sucrose phosphorylase as described above.

Similar to the above-described sucrose phosphorylase, a microorganism (e.g., bacteria, fungi, and the like) used in gene recombination may be easily selected by considering various conditions, such as the ease of expression of 4-α-glucanotransferase, the ease of cultivation, the growth rate, the safety, and the like. It is preferable that 4-α-glucanotransferase does not contain amylase as contaminant. Therefore, it is preferable that a microorganism (e.g., bacteria, fungi, and the like) which produces or expresses no or a low level of amylase is used in gene recombination. For gene recombination of 4-α-glucanotransferase, mesophiles, such as *E. coli* or *Bacillus subtilis*, are preferably used. 4-α-glucanotransferase produced by a microorganism (e.g., bacteria, fungi, and the like), which produces or expresses no or a low level of amylase, contains substantially no amylase, and therefore is preferable for use in the method of the present invention.

Production and purification of 4-α-glucanotransferase obtained by gene recombination can be conducted in a manner similar to that for the above-described sucrose phosphorylase.

The amount of 4-α-glucanotransferase contained in a solution at the start of reaction is representatively about 0.05 to 1,000 U/g sucrose, preferably about 0.1 to 500 U/g sucrose, and more preferably about 0.5 to 100 U/g sucrose relative to sucrose in a solution at the start of reaction. If the weight of 4-α-glucanotransferase is excessively great, the enzyme denatured in a reaction may be likely to aggregate. When the amount to be used is excessively small, the glucan yield may be reduced.

4-α-glucanotransferase may either be purified or not be purified. 4-α-glucanotransferase may either be immobilized or not be immobilized. 4-α-glucanotransferase is preferably immobilized. As a method for immobilization, a carrier binding method (e.g., a covalent binding method, an ionic binding method, or a physical adsorption method), a cross-linking method, an entrapment method (lattice type or microcapsule type) or the like, which are well known to those skilled in the art, may be used. 4-α-glucanotransferase is preferably immobilized on a carrier. 4-α-glucanotransferase may also be immobilized on the same carrier as that for at least one of sucrose phosphorylase and glucan phosphorylase, or on another carrier, and preferably on the same carrier as that for both sucrose phosphorylase and glucan phosphorylase.

(9) Glycogen Debranching Enzyme (EC.2.4.1.25/EC.3.2.1.33)

In the method of the present invention, when a cyclic structure is to be generated in a product, a glycogen debranching enzyme can be used if necessary.

A glycogen debranching enzyme which can be used in the present invention is an enzyme which has two types of activity, i.e., α-1,6-glucosidase activity and 4-α-glucanotransferase activity. Due to the 4-α-glucanotransferase activity possessed by a glycogen debranching enzyme, a product having a cyclic structure is obtained.

A glycogen debranching enzyme is present in microorganisms and animals. Examples of microorganisms producing a glycogen debranching enzyme include yeasts and the like. Examples of animals producing a glycogen debranching enzyme include mammals, such as humans, rabbits, rats, pigs, and the like. Organisms producing a glycogen debranching enzyme are not limited to these.

A glycogen debranching enzyme which can be used in the present invention is preferably derived from yeasts. Preferably, a glycogen debranching enzyme used in the present invention has a high optimal reaction temperature. For example, a glycogen debranching enzyme having a high optimal reaction temperature may be obtained by modifying an enzyme which can act at moderate temperature using a protein engineering technique.

A glycogen debranching enzyme which can be used in the present invention may be isolated directly from microorganisms and animals as described above, which are present in nature and produce the glycogen debranching enzyme.

A glycogen debranching enzyme which can be used in the present invention may be isolated from microorganisms (e.g., bacteria, fungi, and the like) which have been obtained by gene recombination using a gene encoding the glycogen debranching enzyme isolated from the microorganisms and animals.

A glycogen debranching enzyme may be obtained from recombinant microorganisms in a manner similar to that of sucrose phosphorylase as described above.

Similar to the above-described sucrose phosphorylase, a microorganism (e.g., bacteria, fungi, and the like) used in gene recombination may be easily selected by considering various conditions, such as the ease of expression of a glycogen debranching enzyme, the ease of cultivation, the growth rate, the safety, and the like. It is preferable that a glycogen debranching enzyme does not contain amylase as contaminant. Therefore, it is preferable that a microorganism (e.g., bacteria, fungi, and the like) which produces or expresses no or a low level of amylase is used in gene recombination. For gene recombination of a glycogen debranching enzyme, mesophiles, such as *E. coli* or *Bacillus subtilis*, are preferably used. A glycogen debranching enzyme produced by a microorganism (e.g., bacteria, fungi, and the like), which produces or expresses no or a low level of amylase, contains substantially no amylase, and therefore is preferable for use in the method of the present invention.

Production and purification of a glycogen debranching enzyme obtained by gene recombination can be conducted in a manner similar to that for the above-described sucrose phosphorylase.

The amount of a glycogen debranching enzyme contained in a solution at the start of reaction is representatively about 0.01 to 5,000 U/g sucrose, preferably about 0.1 to 1,000 U/g sucrose, and more preferably about 1 to 500 U/g sucrose relative to sucrose in a solution at the start of reaction. If the weight of a glycogen debranching enzyme is excessively great, the enzyme denatured in a reaction may be likely to aggregate. When the amount to be used is excessively small, the glucan yield may be reduced.

A glycogen debranching enzyme may either be purified or not be purified. A glycogen debranching enzyme may either be immobilized or not be immobilized. A glycogen debranching enzyme is preferably immobilized. As a method for immobilization, a carrier binding method (e.g., a covalent binding method, an ionic binding method, or a physical adsorption method), a cross-linking method, an entrapment method (lattice type or microcapsule type) or the like, which are well known to those skilled in the art, may be used. A glycogen debranching enzyme is preferably immobilized on a carrier. A glycogen debranching enzyme may also be immobilized on the same carrier as that for at least one of sucrose phosphorylase and glucan phosphorylase, or on another carrier, and preferably on the same carrier as that for both sucrose phosphorylase and glucan phosphorylase.

(10) Solvent:

A solvent used in the method of the present invention may be any solvent which does not impair the enzyme activities of sucrose phosphorylase and glucan phosphorylase.

It is not necessary that the solvent completely dissolves a material used in the method of the present invention, as long as a reaction which produces glucans can proceed. For example, when an enzyme is carried on a solid carrier, it is not necessary for the enzyme to be dissolved in a solvent. Further, it is not necessary that all materials to be reacted are dissolved, and a portion of the materials may be dissolved to an extent that a reaction can proceed.

A representative solvent is water. A solvent may be the water of a destroyed cell solution obtained along with sucrose phosphorylase or glucan phosphorylase when preparing the above-described sucrose phosphorylase or glucan phosphorylase.

The water may be any of soft water, intermediate water, and hard water. Soft water refers to water having a hardness of at least 20°. Intermediate water refers to water having a hardness of at least 10° and less than 20°. Hard water refers to water having a hardness of less than 10°. The water is preferably soft water or intermediate water, and more preferably soft water.

(11) Other Components:

A solution containing sucrose, a primer, inorganic phosphate or glucose-1-phosphate, sucrose phosphorylase, and glucan phosphorylase may contain any other substances as long as the substances do not interrupt the interaction between sucrose phosphorylase and sucrose and the interaction between glucan phosphorylase and the primer. Examples of such substances include a buffering agent, the components of a microorganism (e.g., bacteria, fungi, and the like) producing sucrose phosphorylase, the components of a microorganism (e.g., bacteria, fungi, and the like) producing glucan phosphorylase, salts, culture medium components, and the like.

<Production of Glucans>

The glucans of the present invention are produced by a step of conducting a reaction in a reaction solution containing sucrose, a primer, inorganic phosphate or glucose-1-phosphate, sucrose phosphorylase, and glucan phosphorylase.

FIG. 1 schematically shows glucan synthesis from sucrose, which is used in the present invention. Glucose-1-phosphate is produced from sucrose and inorganic phosphate using sucrose phosphorylase. The produced glucose-1-phosphate, and glucose-1-phosphate added to the reaction solution are immediately transferred to an appropriate primer by glucan phosphorylase, thereby extending an α-1, 4-glucan chain. Further, inorganic phosphate produced in this case is recycled again in the sucrose-phosphorylase reaction.

Initially, a reaction solution is prepared. For example, the reaction solution may be prepared by adding, to an appropriate solvent, solid sucrose, a primer, inorganic phosphate or glucose-1-phosphate, sucrose phosphorylase, and glucan phosphorylase. Alternatively, the reaction solution may be prepared by mixing solutions containing sucrose, a primer, inorganic phosphate or glucose-1-phosphate, sucrose phosphorylase, and glucan phosphorylase, respectively. Alternatively, the reaction solution may be prepared by mixing a solution containing some of sucrose, a primer, inorganic phosphate or glucose-1-phosphate, sucrose phosphorylase, and glucan phosphorylase with the other solid components. Any buffering agent may be optionally added to the reaction solution as long as it does not inhibit enzyme reactions for the purpose of adjusting pH. An enzyme selected from the group consisting of debranching enzymes, branching enzymes, 4-α-glucanotransferase, and glycogen debranching enzymes may be optionally added to the reaction solution.

Thereafter, the reaction solution is allowed to react by optionally heating by a known method in the art. The reaction temperature may be any value as long as the effect of the present invention can be obtained. When the sucrose concentration of the reaction solution is about 5% to about 100% at the start of a reaction, the reaction temperature may be representatively about 40° C. to about 70° C. The temperature of the solution in this reaction step is preferably such that after a predetermined reaction times at least one, more preferably both, of sucrose phosphorylase and glucan phosphorylase contained in the solution preferably retains at least about 50% of the activity before the reaction, and more preferably at least about 80%. The temperature is preferably about 40° C. to about 70° C., more preferably about 45° C. to about 70° C., more preferably about 45° C. to about 65° C.

It should be note that in the case of the above-described first method, i.e., when the maximum value of sucrose-phosphate ratio in the reaction solution from the start to end of the reaction is no more than about 17, the reaction temperature may be lower than the above-described range. In the case of the above-described fourth method, i.e., when the sucrose-phosphate ratio in the reaction solution at the start of the reaction is no more than about 17, and in the case of the above-described fifth method, i.e., when including a step of further adding sucrose, inorganic phosphate or glucose-1-phosphate to the reaction solution, the reaction temperature may be lower than the above-described range. For example, the reaction can be conducted at room temperature without heating.

The reaction time may be arbitrarily determined by taking into consideration the reaction temperature, the molecular weight of the glucan to be produced by the reaction, and the residual activity of the enzymes. The reaction time is representatively about 1 hour to about 100 hours, more preferably about 1 hour to about 72 hours, even more preferably about 2 hours to about 36 hours, most preferably about 2 to about 24 hours.

Heating may be conducted by any means. Preferably, heating is conducted while agitating in order that heat transfers uniformly in the entire solution. The solution is placed, for example, in a stainless reaction tank comprising a hot-water jacket and an agitation apparatus, and then agitated.

In the method of the present invention, when the reaction has proceeded to some extent, at least one of sucrose, sucrose phosphorylase and glucan phosphorylase may be added to the reaction solution.

In this manner, a solution containing glucan is produced.

After the reaction ended, the reaction solution may be optionally heated at 100° C. for 10 minutes, for example, thereby inactivating the enzymes in the reaction solution.

Alternatively, subsequent steps may be conducted without a treatment for inactivation of the enzymes. The reaction solution may be stored without alteration, or may be subjected to treatment so as to isolate the produced glucan.

<Purification Method>

The produced glucan may be purified if necessary. An example of an impurity removed by the purification is fructose. As examples of a method for purifying glucan, there are a method using an organic solvent (T. J. Schoch et al., J. American Chemical Society, 64, 2957 (1942)) and a method using no organic solvent.

Examples of the organic solvent which can be used in the purification using an organic solvent include acetone, n-amyl alcohol, pentazole, n-propyl alcohol, n-hexyl alcohol, 2-ethyl-1-butanol, 2-ethyl-1-hexanol, lauryl alcohol, cyclohexanol, n-butyl alcohol, 3-pentanol, 4-methyl-2-pentanol, d,1-borneol, α-terpineol, isobutyl alcohol, sec-butyl alcohol, 2-methyl-1-butanol, isoamyl alcohol, tert-amyl alcohol, menthol, methanol, ethanol and ether.

Examples of purification methods using no organic solvent will be described below.

(1) A method of precipitating glucan after a glucan producing reaction by cooling a reaction solution and subjecting the precipitated glucan to a general solid-liquid separation method, such as membrane fractionation, filtration, centrifugation, and the like to purify glucan;

(2) A method of cooling a reaction solution during or after a glucan producing reaction to gel glucan, recovering the gelled glucan, and removing fructose from the gelled glucan by washing with water, freeze-thawing, filtration, or the like; and (3) A method of removing fructose by membrane fractionation using an ultrafiltration membrane or chromatography after a glucan producing reaction, without precipitating glucan dissolved in water.

Examples of the ultrafiltration membrane which can be used in the purification include ultrafiltration membranes (UF membrane unit manufactured by Daicel Chemical Industries, Ltd.) having a molecular weight cutoff of about 1,000 to about 100,000, preferably about 5,000 to about 50,000, and more preferably about 10,000 to about 30,000.

Examples of a carrier which can be used in chromatography include a carrier for gel filtration chromatography, a carrier for ligand exchange chromatography, a carrier for ion exchange chromatography, and a carrier for hydrophobic chromatography.

EXAMPLES

The present invention will be described in more detail by way of the following examples. The present invention is not limited only to the following examples.

(1. Method for Measurement and Calculation)

Each substance in the present invention was determined by the following measurement methods.

(1.1 Quantification of Glucose)

Glucose was quantitated using a commercially available measurement kit. In the measurement, glucose AR-II coloring reagent (manufactured by Wako Pure Chemical Industries, Ltd.) was used.

(1.2 Quantification of Fructose)

Fructose was quantitated using a commercially available measurement kit. In the measurement, F-kit D-glucose/D-fructose (manufactured by Roche) was used.

(1.3 Quantification of Glucose-1-phosphate)

Glucose-1-phosphate was quantitated using the following method. 600 µl of a solution containing glucose-1-phosphate appropriately diluted was added to 300 µl of a measurement reagent (200 mM Tris-HCl (pH 7.0), 3 mM NADP, 15 mM magnesium chloride, 3 mM EDTA, 15 µM glucose-1,6-diphosphate, 6 µg/ml phosphoglucomutase, 6 µg/ml glucose-6-phosphate dehydrogenase), followed by agitation to obtain a reaction system. This reaction system was kept at 30° C. for 30 minutes. Thereafter, the absorbance was measured at 340 nm using a spectrophotometer. The absorbance of sodium glucose-1-phosphate having a known concentration was measured to prepare a standard curve in a similar manner. The absorbance obtained from a sample is applied to the standard curve to determine the glucose-1-phosphate concentration of the sample. Typically, the activity of producing 1 µmol of glucose-1-phosphate per minute is defined as one unit. In this quantification method, only glucose-1-phosphate is quantitated but not inorganic phosphate.

(1.4 Quantification of Inorganic Phosphate)

Inorganic phosphate was quantitated by the following method where inorganic phosphate is regarded as phosphate ion. A solution (200 µl) containing inorganic phosphate was mixed with 800 µl of molybdenum reagent (15 mM ammonium molybdate, 100 mM zinc acetate) and 200 µl of 568 mM ascorbic acid (pH 5.0) was added, followed by agitation, resulting in a reaction system. This reaction system was kept at 30° C. for 20 minutes. Thereafter, the absorbance was measured at 850 nm using a spectrophotometer. The absorbance of inorganic phosphate having a known concentration was measured in a similar manner to prepare a standard curve. The absorbance obtained from a sample was applied to this standard curve to determine the inorganic phosphate in the sample. In this quantification method, inorganic phosphate was quantitated, but not glucose-1-phosphate.

(1.5 Method for Calculating the Glucan Yield)

The glucan yield produced using inorganic phosphate as a starting material is calculated from the amounts of glucose, fructose, and glucose-1-phosphate in a solution after the end of a reaction, using the following formula.

(glucan (mM glucose equivalent))=(fructose (mM))−(glucose-1-phosphate (mM))−(glucose (mM))

This formula is based on the following principle.

In the method of the present invention, initially, reaction (A) represented by the following formula can occur.

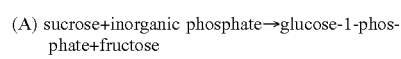
(A) sucrose+inorganic phosphate→glucose-1-phosphate+fructose

This reaction is catalyzed by sucrose phosphorylase. In this reaction, sucrose is reacted within organic phosphate to generate equal molar amounts of glucose-1-phosphate and fructose. The generated fructose no longer reacts with other materials. Therefore, by determining the molar amount of fructose, the molar amount of the generated glucose-1-phosphate can be determined.

Sucrose phosphorylase can catalyze hydrolysis of sucrose in the following reaction (B) as a side reaction in addition to the above-described reaction (A).

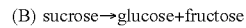
(B) sucrose→glucose+fructose

The amount of glucose taken into glucan is calculated by:

(the amount of glucose taken into glucan)=(the amount of glucose-1-phosphate produced by reaction A)−(the amount of unreacted glucose-1-phosphate)=(the amount of fructose produced by reaction A)−(the amount of unreacted glucose-1-phosphate).

Considering fructose produced in reaction (B), the amount of fructose produced by reaction A is calculated by:

(the amount of fructose produced by reaction A)=
(the amount of fructose after the end of a reaction)−(the amount of glucose after the end of the reaction).

Therefore, the glucan yield is obtained by the following formula.

(glucan (mM glucose equivalent))=(fructose (mM))−
(glucose-1-phosphate (mM))−(glucose (mM))

The glucan yield produced using glucose-1-phosphate as a starting material is calculated from the initial amount of glucose-1-phosphate, and the amounts of glucose, fructose and glucose-1-phosphate in a solution after the end of a reaction by the following formula.

(glucan (mM glucose equivalent))=(initial glucose-1-phosphate (mM))+(fructose (mM))−(glucose (mM))−(glucose-1-phosphate (mM) after reaction)

This formula is based on the following principle.

In a reaction solution, in addition to initial glucose-1-phosphate, reaction A produces glucose-1-phosphate. Therefore, the initial glucose-1-phosphate and the produced glucose-1-phosphate may be used in glucan synthesis. By subtracting the amount of glucose-1-phosphate remaining in the reaction solution after the end of the reaction from the amount of glucose-1-phosphate which can be used in glucan synthesis, the amount of glucose-1-phosphate used in the reaction, i.e., the amount of glucose taken into glucan can be calculated. Therefore, the amount of glucose taken into glucan can be obtained by the above-described formula. It should be note that this formula can be applied to the case when in a SP-GP reaction system, both inorganic phosphate and glucose-1-phosphate are used as starting materials.

(1.6 Glucan Yield)

The glucan yield produced using inorganic phosphate as a starting material is obtained by the following formula.

(glucan yield (%))=(glucan (mM glucose equivalent))/(initial sucrose (mM))×100

The glucan yield produced using glucose-1-phosphate as a starting material is obtained by the following formula.

(glucan yield (%))={(initial glucose-1-phosphate (mM))+(fructose (mM))−(glucose (mM))−(glucose-1-phosphate (mM) after reaction)}/{(initial sucrose (mM))+(initial glucose-1-phosphate (mM))}×100

It should be note that this formula can be applied to the case when in a SP-GP reaction system, both inorganic phosphate and glucose-1-phosphate are used as starting materials.

(1.7 Measurement of Activity of Glucan Phosphorylase)

The activity unit of glucan phosphorylase was determined by the following method.

50 µl of 4% aqueous cluster dextrin solution and 50 µl of 50 mM aqueous sodium glucose-1-phosphate solution were mixed and further 100 µl of an appropriately diluted enzyme liquid was added to initiate a reaction. The mixture was allowed to react at 37° C. for 15 minutes. Thereafter, 10 µl of 20% SDS was added to arrest the reaction. Thereafter, the amount of inorganic phosphate in the reaction solution was qualified by the method described in the above 1.4. The activity to produce 1 µmol of inorganic phosphate per minute in this method is defined as one unit. In the case of the glucan phosphorylase derived from *Thermus aquaticus*, the activity of glucan phosphorylase was measured by reacting at 50° C. instead of 37° C.

(1.8 Measurement of the Activity of Sucrose Phosphorylase)

The activity of sucrose phosphorylase was obtained by the following method.

25 µl of 10% sucrose and 20 µl of 500 mM phosphate buffered solution (pH 7.0) were mixed. 5 µl of appropriately diluted enzyme liquid from which insoluble proteins had been removed was added to the mixture, followed by agitation to obtain a reaction system. This reaction system was allowed to react at 37° C. for 20 minutes. Thereafter, the reaction system was heated at 100° C. for 5 minutes to arrest the reaction. Thereafter, glucose-1-phosphate in the solution after the reaction was quantitated. Typically, the activity to produce 1 µmol of glucose-1-phosphate per minute is defined as one unit.

(2. Preparation of Enzyme)

Various enzymes used in the examples of the present invention were prepared by the following respective methods.

(2.1 Method for Preparing Glucan Phosphorylase Derived from Potato Tuber)

1.4 kg of commercially available potato tubers were peeled. The peeled tubers were ground by a juicer to obtain a juice. Thereafter, the juice was filtered with gauze to obtain a filtrate. Tris buffered solution (pH 7.0) was added to the filtrate to a final concentration of 100 mM to obtain an enzyme liquid. This enzyme liquid was heated in a water bath at 55° C. for 10 minutes after the temperature of the liquid reached 50° C. After the heating, this enzyme liquid was centrifuged using a centrifuge (AVANTI J-25I; manufactured by Beckman) at 8,500 rpm for 20 minutes to remove insoluble proteins and the like, thereby obtaining the supernatant.

Ammonium sulfate was added to the resultant supernatant to 100 g/L. The mixture was left at 4° C. for 2 hours, precipitating proteins. Thereafter, the mixture was centrifuged with a centrifuge (AVANTIJ-25I; manufactured by Beckman) at 8,500 rpm for 20 minutes to remove insoluble proteins and the like, thereby obtaining the supernatant. Further, ammonium sulfate was added to the resultant supernatant to a final concentration of 250 g/L. The mixture was left at 4° C. for 2 hours, precipitating proteins. Thereafter, the mixture was centrifuged with a centrifuge (AVANTI J-25I; manufactured by Beckman) at 8,500 rpm for 20 minutes to recover insoluble proteins.

The recovered insoluble protein was suspended in 150 ml of 25 mM Tris buffered solution (pH 7.0). The suspended enzyme liquid was dialyzed in the same buffered solution overnight. After the dialysis the sample was allowed to be adsorbed to pre-equilibrated Q-Sepharose anion exchange resin (manufactured by Pharmacia), followed by washing with a buffered solution containing 200 mM sodium chloride. Thereafter, the proteins were eluted with a buffered solution containing 400 mM sodium chloride, and the eluate was recovered. The eluate was called a solution containing partially purified, potato tuber-derived glucan phosphorylase.

In some purchased potatoes, a glucan phosphorylase-containing solution which can be used in the present invention can be obtained in this stage, but in most cases further purification is required. If necessary, fractionation by gel filtration chromatography using Sephacryl S-200HR (manufactured by Pharmacia) or the like and fractionation by hydrophobic chromatography using Phenyl-TOYOPEARL 650M (manufactured by Tosoh Corporation) or the like are combined, thereby making it possible to obtain a purified, potato glucan phosphorylase-containing solution.

(2.2 Method for Preparing Recombinant Potato Glucan Phosphorylase)

A potato glucan phosphorylase gene (Nakano et al., Journal of Biochemistry (Tokyo) 106 (1989) 691) and a selectable marker gene $Amp^r$ were incorporated into an expression vector pET34 (manufactured by STRATAGENE) to obtain plasmid pET-PGP113. In this plasmid, the glucan phosphorylase gene was operably-linked under the control of an isopropyl-β-D-thiogalactopyranoside (IPTG) inducible promoter. This plasmid was introduced into *E. coli* TG-1 (manufactured by STRATAGENE) by a competent cell method. This *E. coli* was plated on a plate containing LB medium (1% tryptone, 0.5% yeast extract (both manufactured by Difco), 1% sodium chloride, 1.5% agar)) containing the antibiotic ampicillin, followed by incubation at 37° C. overnight. By selecting *E. coli* which grew on this plate, *E. coli* having the introduced potato-derived glucan phosphorylase gene were obtained. Analysis of the sequence of the introduced gene confirmed that the resultant *E. coli* had the glucan phosphorylase gene. Further, the activity of glucan phosphorylase was measured to confirm that the resultant *E. coli* expressed glucan phosphorylase.

The *E. coli* was inoculated into one liter of LB medium (1% tryptone, 0.5% yeast extract (both manufactured by Difco), 1% sodium chloride) containing the antibiotic ampicillin, followed by shaking culture at 37° C. for 3 hours while shaking at 120 rpm. Thereafter, IPTG and pyridoxine were added to the medium to 0.1 mM and 1 mM, respectively, followed by further shaking culture at 22° C. for 20 hours. Thereafter, the culture was centrifuged at 5,000 rpm for 5 minutes to collect *E. coli* cells. The resultant cells were suspended in 50 ml of 20 mM Tris-HCl buffered solution (pH 7.0) containing 0.05% Triton X-100, followed by destruction by sonication to obtain 50 ml of the destroyed bacterial cell solution. This destroyed bacterial cell solution contained 4.7 U/mg glucan phosphorylase.

This destroyed bacterial cell solution was heated at 55° C. for 30 minutes. After the heating, the liquid was centrifuged at 8,500 rpm for 20 minutes to remove insoluble proteins and the like, thereby obtaining the supernatant. The resultant supernatant was passed through pre-equilibrated Q-Sepharose anion exchange resin so that glucan phosphorylase was allowed to be adsorbed to the resin. The resin was washed with a buffered solution containing 200 mM sodium chloride to remove impurities. Thereafter, the proteins were eluted with a buffered solution containing 300 mM sodium chloride. The resultant eluate was called a recombinant glucan phosphorylase solution.

(2.3 Method for Preparing *Thermus aquaticus* Glucan Phosphorylase)

An enzyme prepared by a method of Takaha et al. (J. Appl. Glycosci., 48(1) (2001) 71) is referred to as *Thermus aquaticus* glucan phosphorylase.

(2.4 Method for Preparing Recombinant *Thermus aquaticus* Glucan Phosphorylase)

A *Thermus aquaticus* glucan phosphorylase gene (J. Appl. Glycosci., 48(1) (2001) 71) and selectable marker genes $Amp^r$ and $Tet^r$ were incorporated into pKK388-1 (manufactured by CLONTECH) to obtain plasmid pKK388-GP. In this plasmid, the glucan phosphorylase gene was operably-linked under the control of an isopropyl-β-D-thiogalactopyranoside (IPTG) inducible promoter. This plasmid was introduced into *E. coli* MC1061 (manufactured by Pharmacia) by a competent cell method. This *E. coli* was plated on a plate containing LB medium containing the antibiotic ampicillin and IPTG, followed by incubation at 37° C. overnight. By selecting *E. coli* which grew on this plate, *E. coli* having an introduced glucan phosphorylase gene was obtained. Analysis of the sequence of the introduced gene confirmed that the resultant *E. coli* had the glucan phosphorylase gene. Further, the activity of glucan phosphorylase was measured to confirm that the resultant *E. coli* expressed glucan phosphorylase.

The *E. coli* was inoculated into one liter of LB medium containing the antibiotic ampicillin, followed by shaking culture at 37° C. for 4-5 hours while shaking at 120 rpm. Thereafter, IPTG was added to the medium to 0.01 mM, followed by further shaking culture at 37° C. for 20 hours. Thereafter, the culture was centrifuged at 5,000 rpm for 5 minutes to collect *E. coli* cells.

The resultant cells were suspended in 50 ml of 20 mM Tris-HCl buffered solution (pH 7.0), followed by destruction by sonication to obtain 50 ml of destroyed bacterial cell solution. This destroyed bacterial cell solution contained 4.2 U/mg glucan phosphorylase.

Thereafter, this destroyed bacterial cell liquid was heated at 70° C. for 30 minutes. After the heating, the liquid was centrifuged with a centrifuge (AVANTI J-25I; manufactured by Beckman) at 8,500 rpm for 20 minutes to remove insoluble proteins and the like, thereby obtaining the supernatant. The resultant supernatant was called a recombinant *Thermus aquaticus*, glucan phosphorylase solution.

(2.5 Method for Preparing Recombinant *Streptococcus mutans* Sucrose Phosphorylase)

A *Streptococcus mutans* sucrose phosphorylase gene (Ferretti, J. J. et al., Ingbritt. Infect. Immun. 56:1585-88) and selectable marker genes $Amp^r$ and $Tet^r$ were incorporated into pKK388-1 to obtain plasmid pKK388-SMSP. In this plasmid, the sucrose phosphorylase gene was operably-linked under the control of an isopropyl-β-D-thiogalactopyranoside (IPTG) inducible promoter. This plasmid was introduced into *E. coli* TG-1 (manufactured by STRATAGENE) by a competent cell method. This *E. coli* was plated on a plate containing LB medium containing an antibiotic ampicillin and IPTG, followed by incubation at 37° C. overnight. By selecting *E. coli* which grew on this plate, *E. coli* having an introduced sucrose phosphorylase gene was obtained. Analysis of the sequence of the introduced gene confirmed that the resultant *E. coli* had the sucrose phosphorylase gene. Further, the activity of sucrose phosphorylase was measured to confirm that the resultant *E. coli* expressed sucrose phosphorylase.

The *E. coli* was inoculated into one liter of LB medium containing the antibiotics ampicillin and tetracycline, followed by shaking culture at 37° C. for 6-7 hours while shaking at 120 rpm. Thereafter, IPTG was added to the medium to 0.04 mM, followed by further shaking culture at 30° C. for 18 hours. Thereafter, the culture was centrifuged at 5,000 rpm for 5 minutes to collect *E. coli* cells. The resultant cells were suspended in 50 ml of 20 mM Tris-HCl buffered solution (pH 7.0), followed by destruction by sonication to obtain 50 ml of destroyed bacterial cell liquid. This destroyed liquid contained 10 U/mg sucrose phosphorylase.

Thereafter, sucrose was added to the destroyed bacterial cell liquid to obtain 10% sucrose-containing destroyed bacterial cell liquid. This destroyed bacterial cell liquid was heated in a water bath at 55° C. for 30 minutes. After the heating, the destroyed bacterial cell liquid was centrifuged with a centrifuge (AVANTI J-25I; manufactured by Beckman) at 8,500 rpm for 20 minutes to remove insoluble proteins and the like, thereby obtaining the supernatant. The resultant supernatant was passed through pre-equilibrated Q-Sepharose anion exchange resin so that sucrose phosphorylase was allowed to be adsorbed to the resin. The resin was washed with a buffered solution containing 100 mM sodium chloride to remove impurities. Thereafter, the sucrose phosphorylase was eluted with a buffered solution containing 300 mM sodium chloride. The resultant eluate was called a recombinant *Streptococcus mutans* sucrose phosphorylase solution.

(2.6 Preparation of Recombinant *Bacillus stearothermophilus* Glucan Phosphorylase)

An enzyme prepared by a method of Takata et al. (J. Ferment. Bioeng., 85(2), 156 (1998)) was called recombinant *Bacillus stearothermophilus* glucan phosphorylase.

(3. Measurement of the Molecular Weight of Glucans)

The molecular weight of the glucans synthesized in the present invention was measured by the following method.

Glucans synthesized in the present invention were completely dissolved in 1N sodium hydroxide, followed by neutralization with an appropriate amount of hydrochloric acid. Thereafter, about 300 µg of glucan was subjected to gel filtration chromatography in combination with a differential refractometer and a multi-angle light scattering detector to obtain the average molecular weight.

Specifically, Shodex SB806M-HQ (manufactured by Showa Denko K.K.) was used as a column. As detectors, a multi-angle light scattering detector (DAWN-DSP, manufactured by Wyatt Technology) and a differential refractometer (Shodex RI-71, manufactured by Showa Denko K.K.) were used, being linked in that order. The column was held at 40° C., and a 0.1 M sodium nitrate solution was used as an eluant where the flow rate was 1 mL/min. The resultant signals were collected and analyzed by data analysis software (brand-name ASTRA, manufactured by Wyatt Technology) to calculate the weight average molecular weight.

Comparative Example 0-1 and 0-2

Comparison in Yield between Reaction Temperatures 37° C. and 45° C.

The compositions of reaction solution at the start of the reaction, which were used in comparative examples 0-1 and 0-2, are shown in Table 1 below.

TABLE 1

|  | Sucrose (%) | G7 (mM) | Pi (mM) | SP (U/g sucrose) | GP (U/g sucrose) | Reaction temperature |
|---|---|---|---|---|---|---|
| Comparative example 0-1 | 4 | 2 | 20 | 10 | 10 | 37° C. |
| Comparative example 0-2 | 4 | 2 | 20 | 10 | 10 | 45° C. |

G7: Maltoheptaose
Pi: Potassium dihydrogen phosphate-disodium hydrogen phosphate buffered solution
SP: Leuconostoc mesenteroides-derived sucrose phosphorylase
GP: Potato-derived glucan phosphorylase Specifically, sucrose, inorganic phosphate, *Leuconostoc mesenteroides* sucrose phosphorylase (manufactured by Oriental Yeast Co., Ltd.), potato tuber-derived glucan phosphorylase prepared in the above 2.1, and maltoheptaose were dissolved in 100 mM citrate buffered solution (pH 7.0), resulting in a solution containing 4% sucrose, 20 mM inorganic phosphate, 10 U/g sucrose of *Leuconostoc mesenteroides* sucrose phosphorylase, 10 U/g sucrose of potato tuber-derived glucan phosphorylase, and 2 mM maltoheptaose. This solution was allowed to react at 37° C. (comparative example 0-1) or 45° C. (comparative example 0-2) for 18 hours, thereby synthesizing amylose. The volume of the reaction was 1 ml.

After the reaction, the yield of the synthesized amylase was determined in a manner as described in the above 1.6. The results are shown in FIG. 2.

In the present specification, a method for producing amylose at 37° C. using *Leuconostoc mesenteroides* sucrose phosphorylase (purchased from Oriental Yeast Co., Ltd.), potato tuber-derived glucan phosphorylase, and 4% sucrose is called a conventional method.

Figure 2:
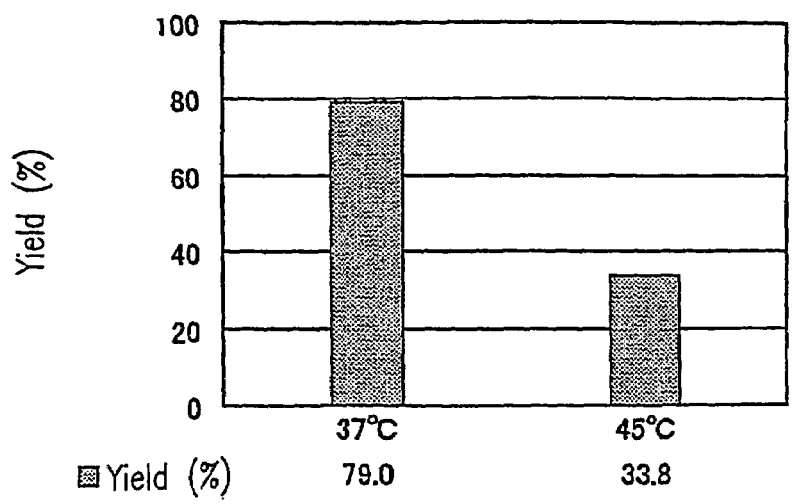
FIG. 2 is a graph showing the yields of amylose when reactions were conducted using 4% initial sucrose, *Leuconostoc mesenteroides*-derived sucrose phosphorylase, and potato-derived glucan phosphorylase where the reaction temperatures were 37° C. and 45° C.

As described in FIG. 2, whereas the yield of amylose when the reaction was conducted at 37° C. was 79%, the yield of amylose when the reaction was conducted at 45° C. was as low as 33.8%.

Thus, the substrate concentration of conventional methods is industrially disadvantageous for production of amylose at high temperature. The optimal temperature of *Leuconostoc mesenteroides*-derived sucrose phosphorylase used is about 37° C. Therefore, this enzyme is considered to have a low level of heat-resistance. It is considered that the low yield of amylose at high temperature was attributed to the low heat-resistance of the enzyme.

Examples 1-1 to 1-5 and Comparative Example 1-1

Amylose Synthesis Using Various Sucrose Concentrations and High Reaction Temperature)

Amylose synthesis was conducted using reaction mixtures whose compositions (at the start of the reaction) are shown in Table 2 below.

TABLE 2

| No. | Sucrose (%) | G7 (mM) | Pi (mM) | SP (U/g sucrose) | GP (U/g sucrose) | Reaction temperature |
|---|---|---|---|---|---|---|
| Comparative example 1-1 | 4 | 2 | 20 | 10 | 10 | 45° C. |
| Example 1-1 | 8 | 4 | 40 | 10 | 10 | 45° C. |
| Example 1-2 | 10 | 5 | 50 | 10 | 10 | 45° C. |
| Example 1-3 | 15 | 7.5 | 75 | 10 | 10 | 45° C. |
| Example 1-4 | 20 | 10 | 100 | 10 | 10 | 45° C. |
| Example 1-5 | 25 | 12.5 | 125 | 10 | 10 | 45° C. |

Figure 3:
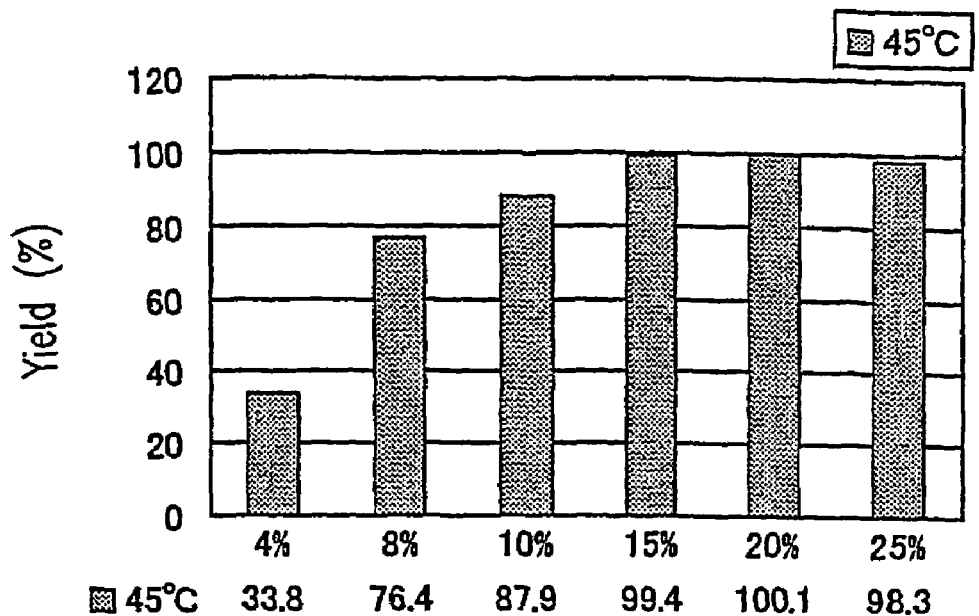
FIG. 3 is a graph showing the yields of amylose when reactions were conducted at various initial sucrose concentrations where the reaction temperature was 45° C.

G7: Maltoheptaose
Pi: Potassium dihydrogen phosphate-disodium hydrogen phosphate buffered solution
SP: Leuconostoc mesenteroides-derived sucrose phosphorylase
GP: Potato-derived glucan phosphorylase After the reaction, the yield of synthesized amylose was determined according to Section 1.6 above. The results are shown in FIG. 3.

The sucrose concentration was increased from 4% (comparative example 1-1) used in conventional methods to at least 8% (Example 1-1 to 1-5), making it possible to achieve a reaction at 45° C. Therefore, the yield of amylose was increased.

Specifically, under the above-described conditions, the proportions among the substrates (i.e., sucrose, maltoheptaose, and inorganic phosphate) and the amount of the enzymes were not changed but the sucrose concentration was varied between 8% and 25%, so that the yield of amylose was increased. As shown in FIG. 3, the yield was 76.4% at 45° C. where the sucrose concentration was 8%.

This is at least twice the yield where the sucrose concentration was 4% and the reaction temperature was 45° C., so that substantially the same yield as that obtained by conventional methods was obtained. When the sucrose concentration was at least 15%, the yield of amylose was substantially 100%. Thus, in the case of amylose synthesis from sucrose at 45° C., a low sucrose concentration leads to a low yield and poor efficiency, but a higher sucrose concentration allows industrial production at 45° C.

Examples 2-1 to 2-5 and Comparative Examples 2-1 to 2-7

Amylose Synthesis with Small Amounts of Enzymes

Amylose synthesis was conducted using reaction mixtures whose compositions (at the start of the reaction) are shown in Table 3 below.

TABLE 3

| No. | Sucrose (%) | G7 (mM) | Pi (mM) | SP (U/g sucrose) | GP (U/g sucrose) | Reaction temperature |
|---|---|---|---|---|---|---|
| Comparative example 2-1 | 4 | 2 | 20 | 5 | 5 | 37° C. |
| Comparative example 2-2 | 8 | 4 | 40 | 5 | 5 | 37° C. |
| Comparative example 2-3 | 10 | 5 | 50 | 5 | 5 | 37° C. |
| Comparative example 2-4 | 15 | 7.5 | 75 | 5 | 5 | 37° C. |
| Comparative example 2-5 | 20 | 10 | 100 | 5 | 5 | 37° C. |
| Comparative example 2-6 | 25 | 12.5 | 125 | 5 | 5 | 37° C. |
| Comparative example 2-7 | 4 | 2 | 20 | 5 | 5 | 45° C. |
| Example 2-1 | 8 | 4 | 40 | 5 | 5 | 45° C. |
| Example 2-2 | 10 | 5 | 50 | 5 | 5 | 45° C. |
| Example 2-3 | 15 | 7.5 | 75 | 5 | 5 | 45° C. |
| Example 2-4 | 20 | 10 | 100 | 5 | 5 | 45° C. |
| Example 2-5 | 25 | 12.5 | 125 | 5 | 5 | 45° C. |

G7: Maltoheptaose
Pi: Potassium dihydrogen phosphate-disodium hydrogen phosphate buffered solution
SP: Leuconostoc mesenteroides-derived sucrose phosphorylase
GP: Potato-derived glucan phosphorylase Specifically, in Examples 2-1 to 2-5 and comparative examples 2-1 to 2-7, the amount of the enzymes was half that of comparative examples 1-1 and Examples 1-1 to 1-5, and reactions were conducted at 37° C. and 45° C. Except for that, each amylose synthesis was conducted in the same manner as that of comparative example 1-1 and Examples 1-1 to 1-5.

After the reaction, the yield of synthesized amylose was determined according to Section 1.6 above. The results are shown in FIG. 4.

When the sucrose concentration was at least 15%, the yields of amylose for reactions at 45° C. were no less than those for reactions at 37° C.

Figure 4:
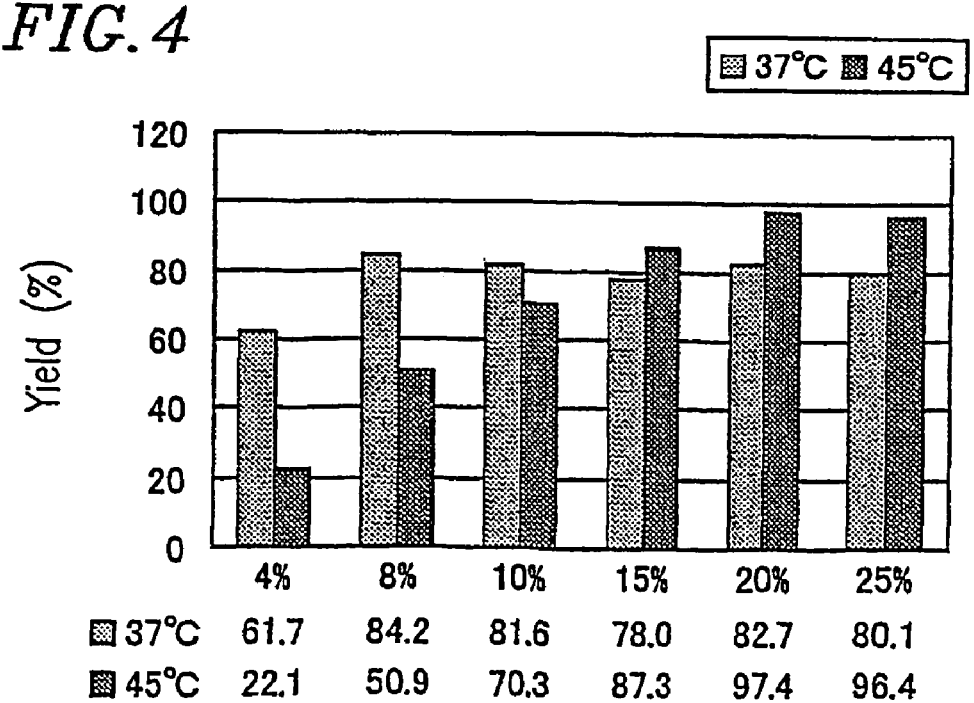
FIG. 4 is a graph showing the yields of amylose when reactions were conducted at various initial sucrose concentrations where the reaction temperatures were 37° C. and 45° C.

As shown in FIG. 4, under these conditions, whereas the yield of amylose was about 60% by conventional methods, the yield was as low as 22.1% where the sucrose concentration was 4% and the reaction temperature was 45° C. However, when the proportions among the substrates (i.e., sucrose, maltoheptaose, and inorganic phosphate) and the amount of the enzymes were not changed and the sucrose concentration was varied between 8% and 25%, the yields of amylose of the reactions at 45° C. were increased. In the case of reactions where the sucrose concentration was at least 15% and the reaction temperature was 45° C., the yield of amylose was higher than that obtained at 37° C. Thus, when the reactions were conducted where the sucrose concentration was at least 15%, not only could the reactions be conducted at 45° C., but also higher productivity than that of the reactions at 37° C. could be realized.

Examples 3-1-1 to 3-2-5 and Comparative Examples 3-1-1 and 3-2-1

Amylose Synthesis where Heat-Resistant Sucrose Phosphorylase is Used

Amylose synthesis was conducted using reaction mixtures whose compositions (at the start of the reaction) are shown in Table 4 below.

TABLE 4

| No. | Sucrose (%) | G7 (mM) | Pi (mM) | SP (U/g sucrose) | GP (U/g sucrose) | Reaction temperature |
|---|---|---|---|---|---|---|
| Comparative example 3-1-1 | 4 | 2 | 20 | 10 | 10 | 45° C. |
| Example 3-1-1 | 8 | 4 | 40 | 10 | 10 | 45° C. |
| Example 3-1-2 | 10 | 5 | 50 | 10 | 10 | 45° C. |
| Example 3-1-3 | 15 | 7.5 | 75 | 10 | 10 | 45° C. |
| Example 3-1-4 | 20 | 10 | 100 | 10 | 10 | 45° C. |
| Example 3-1-5 | 25 | 12.5 | 125 | 10 | 10 | 45° C. |
| Comparative example 3-2-1 | 4 | 2 | 20 | 10 | 10 | 50° C. |
| Example 3-2-1 | 8 | 4 | 40 | 10 | 10 | 50° C. |
| Example 3-2-2 | 10 | 5 | 50 | 10 | 10 | 50° C. |
| Example 3-2-3 | 15 | 7.5 | 75 | 10 | 10 | 50° C. |
| Example 3-2-4 | 20 | 10 | 100 | 10 | 10 | 50° C. |
| Example 3-2-5 | 25 | 12.5 | 125 | 10 | 10 | 50° C. |

G7: Maltoheptaose
Pi: Potassium dihydrogen phosphate-disodium hydrogen phosphate buffered solution
SP: Streptococcus mutans-derived sucrose phosphorylas
GP: Potato-derived glucan phosphorylase Specifically, 10 U/g sucrose (activity unit) of *Streptococcus mutans*-derived sucrose phosphorylase obtained according to Section 2.5 above was used instead of *Leuconostoc mesenteroides*-derived sucrose phosphorylase, 10 U/g sucrose (activity unit) of glucan phosphorylase was used, and the enzyme reactions were conducted at 45° C. or 50° C. Except for that, amylose synthesis was conducted in comparative examples 3-1-1 and 3-2-1 and Examples 3-1-1 to 3-2-5 in the same manner as that in comparative example 2-1 and Examples 2-1 to 2-5.

After the reaction, the yield of synthesized amylose was determined according to Section 1.6 above. The results are shown in FIG. 5.

Even when sucrose phosphorylase was changed from *Leuconostoc mesenteroides*-derived sucrose phosphorylase used in conventional methods to *Streptococcus mutans*-derived sucrose phosphorylase, amylose could be produced when the reaction temperature was 45° C.

Further, when sucrose phosphorylase was changed from *Leuconostoc mesenteroides*-derived sucrose phosphorylase used in conventional methods to *Streptococcus mutans*-derived sucrose phosphorylase, and the sucrose concentration was increased from 4% to at least 8%, highly-efficient reactions at 50° C. were made possible, so that the yield of amylose was increased.

Figure 5:
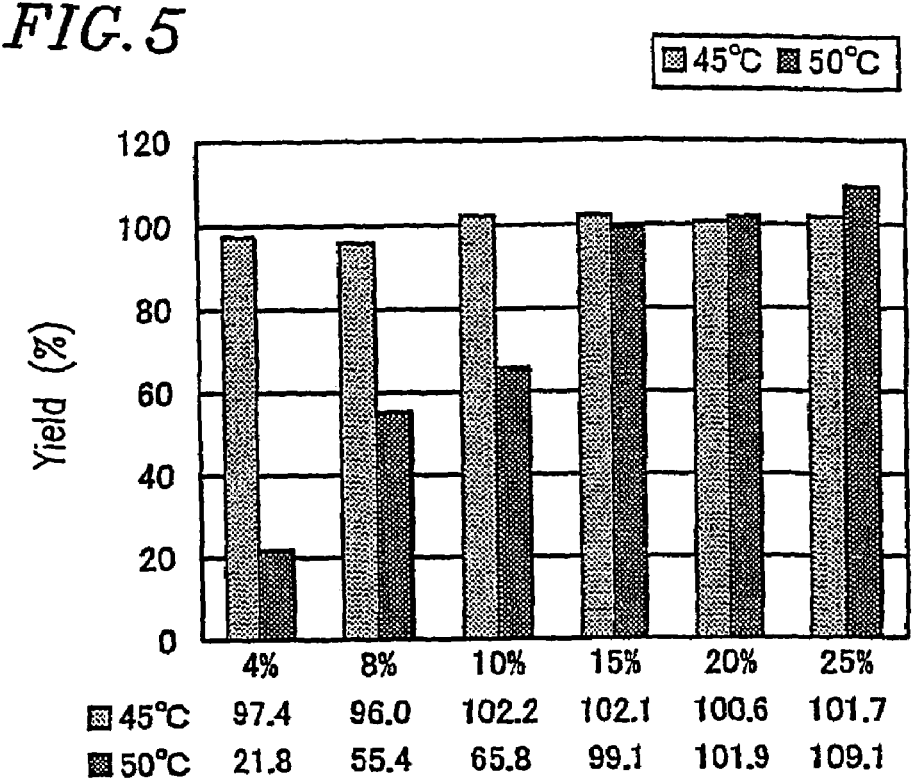
FIG. 5 is a graph showing the yields of amylose when reactions were conducted using *Streptococcus mutans* (heat-resistant bacterium)-derived sucrose phosphorylase and potato-derived glucan phosphorylase with various initial sucrose concentrations and the reaction temperatures were 45° C. and 50° C.

As shown in FIG. 5, when the reaction temperature was 45° C., the yield of amylose was 97.4% where the sucrose concentration was 4%. Further, even when the proportions among the substrates and the amounts of the enzymes were not changed, and the sucrose concentration was varied between 8% and 25%, the yield of amylose was consistent at a higher level. Thus, when sucrose phosphorylase was Streptococcus mutans-derived sucrose phosphorylase, highly-efficient amylose production at 45° C. was made possible.

Further, as shown in FIG. 5, when the reaction temperature was 50° C., the yield of amylose was as low as 21.8% where the sucrose concentration was 4%. However, when the proportions among the substrates and the amounts of the enzymes were not changed, and the sucrose concentration was varied between 8% and 25%, the yield of amylose was increased. The yield was 55.4% where the sucrose concentration was 8%, which was at least twice the yield where the sucrose concentration was 4%. When the sucrose concentration was at least 15%, the yield of amylose was substantially 100%. Thus, whereas the yield of amylose synthesis was low and inefficient where the sucrose concentration was 4% and the reaction temperature was 50° C., highly-efficient amylose production at 50° C. was made possible by using Streptococcus mutans-derived sucrose phosphorylase and increasing the sucrose concentration.

Examples 4-1-1 to 4-2-5, and Comparative Examples 4-1-1 and 4-2-1

Amylose Synthesis where the Amount of Enzymes was Low and Heat-Resistant Sucrose Phosphorylase was Used)

Amylose synthesis was conducted using reaction mixtures whose compositions (at the start of the reaction) are shown in Table 5 below.

TABLE 5

| No. | Sucrose (%) | G7 (mM) | Pi (mM) | SP (U/g sucrose) | GP (U/g sucrose) | Reaction temperature |
|---|---|---|---|---|---|---|
| Comparative example 4-1-1 | 4 | 2 | 20 | 5 | 5 | 45° C. |
| Example 4-1-1 | 8 | 4 | 40 | 5 | 5 | 45° C. |
| Example 4-1-2 | 10 | 5 | 50 | 5 | 5 | 45° C. |
| Example 4-1-3 | 15 | 7.5 | 75 | 5 | 5 | 45° C. |
| Example 4-1-4 | 20 | 10 | 100 | 5 | 5 | 45° C. |
| Example 4-1-5 | 25 | 12.5 | 125 | 5 | 5 | 45° C. |
| Comparative example 4-2-1 | 4 | 2 | 20 | 5 | 5 | 50° C. |
| Example 4-2-1 | 8 | 4 | 40 | 5 | 5 | 50° C. |
| Example 4-2-2 | 10 | 5 | 50 | 5 | 5 | 50° C. |
| Example 4-2-3 | 15 | 7.5 | 75 | 5 | 5 | 50° C. |
| Example 4-2-4 | 20 | 10 | 100 | 5 | 5 | 50° C. |
| Example 4-2-5 | 25 | 12.5 | 125 | 5 | 5 | 50° C. |

G7: Maltoheptaose
Pi: Potassium dihydrogen phosphate-disodium hydrogen phosphate buffered solution
SP: Streptococcus mutans-derived sucrose phosphorylase
GP: Potato-derived glucan phosphorylase Specifically, the amounts of the enzymes was half that of comparative examples 3-1-1 and 3-2-1 as well as Examples 3-1-1 to 3-2-5. Except for that, amylose synthesis was conducted in the same manner as that in comparative examples 3-1-1 and 3-2-1 as well as Examples 3-1-1 to 3-2-5.

After the reaction, the yield of synthesized amylose was determined according to Section 1.6 above. The results are shown in FIG. 6.

When sucrose phosphorylase was changed from Leuconostoc mesenteroides-derived sucrose phosphorylase used in conventional methods to Streptococcus mutans-derived sucrose phosphorylase, and the amounts of the enzymes was half that of conventional methods, the yield of amylose by reactions at 50° C. was no less than that by reactions at 45° C. where the sucrose concentration was at least 15%.

Figure 6:
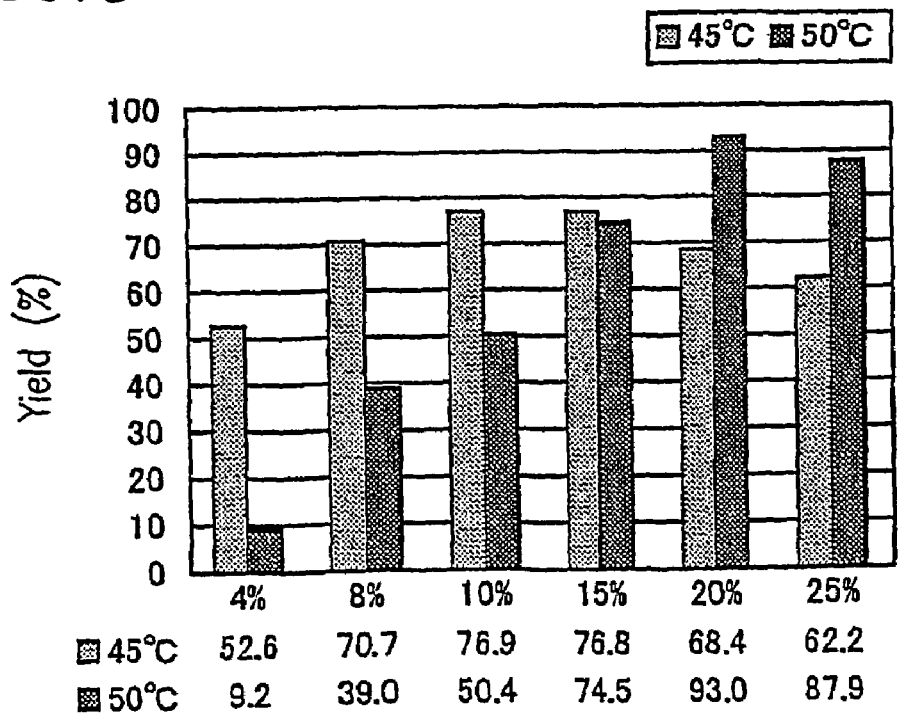
FIG. 6 is a graph showing the yields of amylose when reactions were conducted using *Streptococcus mutans*-derived sucrose phosphorylase and potato-derived glucan phosphorylase in amounts corresponding to half the activity of the enzymes used in FIG. 5 with various initial sucrose concentrations and the reaction temperatures were 45° C. and 50° C.

As shown in FIG. 6, whereas the yields of amylose obtained by the reactions at 45° C. were about 50% where the sucrose concentration was 4%, the yield obtained by the reaction at 50° C. were as low as 9.2% where the sucrose concentration was 4%. However, when the proportions among the substrates and the amounts of the enzymes were not changed, and the sucrose concentration was varied between 8% and 25%, the yields of amylose obtained by the reactions at 50° C. were increased. When the sucrose concentration was at least 15%, the yields of amylose obtained by the reactions at 50° C. were higher than those obtained by the reactions at 45° C. Thus, when Streptococcus mutans-derived sucrose phosphorylase was used and the sucrose concentration was at least 15%, not only could a reaction be conducted at 50° C., but also higher productivity than that of the reactions at 45° C. could be realized.

Examples 5-1 to 5-5 and Comparative Example 5-1

Amylose Synthesis where Leuconostoc mesenteroides-Derived Sucrose Phosphorylase and Extremely Thermophilic Bacterium-derived Glucan Phosphorylase were Used Amylose synthesis was conducted using reaction mixtures whose compositions (at the start of the reaction) are shown in Table 6 below.

TABLE 6

| No. | Sucrose (%) | G7 (mM) | Pi (mM) | SP (U/g sucrose) | GP (U/g sucrose) | Reaction temperature |
|---|---|---|---|---|---|---|
| Comparative example 5-1 | 4 | 2 | 20 | 10 | 10 | 45° C. |
| Example 5-1 | 8 | 4 | 40 | 10 | 10 | 45° C. |
| Example 5-2 | 10 | 5 | 50 | 10 | 10 | 45° C. |
| Example 5-3 | 15 | 7.5 | 75 | 10 | 10 | 45° C. |
| Example 5-4 | 20 | 10 | 100 | 10 | 10 | 45° C. |
| Example 5-5 | 25 | 12.5 | 125 | 10 | 10 | 45° C. |

G7: Maltoheptaose
Pi: Potassium dihydrogen phosphate-disodium hydrogen phosphate buffered solution
SP: Leuconostoc mesenteroides-derived sucrose phosphorylase
GP: Thermus aquaticus-derived glucan phosphorylase Specifically, Thermus aquaticus-derived glucan phosphorylase was used instead of potato-derived glucan phosphorylase. Except for that, amylose synthesis was conducted in the same manner as that in comparative example 1-1 and Examples 1-1 to 1-5.

Figure 7:
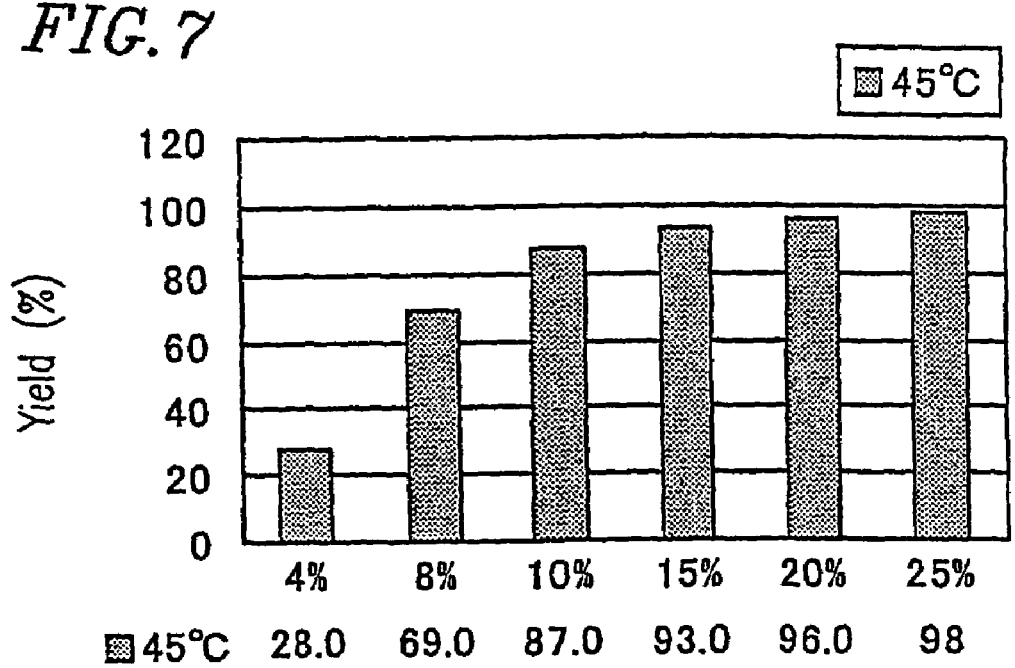
FIG. 7 is a graph showing the yields of amylose when reactions were conducted using *Leuconostoc mesenteroides*-derived sucrose phosphorylase and *Thermus aquaticus*-derived glucan phosphorylase with various initial sucrose concentrations and the reaction temperatures was 45° C.

After the reaction, the yield of synthesized amylose was determined according to Section 1.6 above. The results are shown in FIG. 7.

When Thermus aquaticus-derived glucan phosphorylase was used and the sucrose concentration was increased from 4% in conventional methods to at least 8%, the reactions could be conducted at 45° C., so that the yield of amylose was increased.

Specifically, under the above-described conditions, when the proportions among the substrates and the amounts of the enzymes were not changed, and the sucrose concentration was varied between 8% and 25%, the yield of amylose was increased. As shown in FIG. 7, where as the yield was 28.0% where the sucrose concentration was 4% and the reaction temperature was 45° C., the yield was 69.0% where the sucrose concentration was 8%. Further, when the sucrose concentration was at least 15%, the yield of amylose was substantially 100%. Thus, it was confirmed that when *Thermus aquaticus* (extremely thermophilic bacterium)-derived glucan phosphorylase was used instead of potato-derived glucan phosphorylase, amylose could be produced at 45° C.

Examples 6-1 to 6-5 and Comparative Examples 6-1 to 6-7

Amylose Synthesis using *Leuconostoc mesenteroides*-derived Sucrose Phosphorylase and Extremely Thermophilic Bacterium-derived Glucan Phosphorylase with Small Amounts of Enzymes)

Amylose synthesis was conducted using reaction mixtures whose compositions (at the start of the reaction) are shown in Table 7 below.

TABLE 7

| No. | Sucrose (%) | G7 (mM) | Pi (mM) | SP (U/g sucrose) | GP (U/g sucrose) | Reaction temperature |
|---|---|---|---|---|---|---|
| Comparative example 6-1 | 4 | 2 | 20 | 5 | 5 | 37° C. |
| Comparative example 6-2 | 8 | 4 | 40 | 5 | 5 | 37° C. |
| Comparative example 6-3 | 10 | 5 | 50 | 5 | 5 | 37° C. |
| Comparative example 6-4 | 15 | 7.5 | 75 | 5 | 5 | 37° C. |
| Comparative example 6-5 | 20 | 10 | 100 | 5 | 5 | 37° C. |
| Comparative example 6-6 | 25 | 12.5 | 125 | 5 | 5 | 37° C. |
| Comparative example 6-7 | 4 | 2 | 20 | 5 | 5 | 45° C. |
| Example 6-1 | 8 | 4 | 40 | 5 | 5 | 45° C. |
| Example 6-2 | 10 | 5 | 50 | 5 | 5 | 45° C. |
| Example 6-3 | 15 | 7.5 | 75 | 5 | 5 | 45° C. |
| Example 6-4 | 20 | 10 | 100 | 5 | 5 | 45° C. |
| Example 6-5 | 25 | 12.5 | 125 | 5 | 5 | 45° C. |

G7: Maltoheptaose
Pi: Potassium dihydrogen phosphate-disodium hydrogen phosphate buffered solution
SP: Leuconostoc mesenteroides-derived sucrose phosphorylase
GP: Thermus aquaticus-derived glucan phosphorylase Specifically, in Examples 6-1 to 6-5 and comparative examples 6-1 to 6-7, the amounts of the enzymes were half those in Examples 5-1 to 5-5 and comparative example 5-1, and reactions were conducted at 37° C. and 45° C. Except for that, amylose synthesis was conducted in the same manner as that in Examples 5-1 to 5-5 and comparative example 5-1.

After the reaction, the yield of synthesized amylose was determined according to Section 1.6 above. The results are shown in FIG. 8.

When *Thermus aquaticus*-derived glucan phosphorylase was used, the yields of amylose obtained by the reactions where the sucrose concentration was at least 15% and the reaction temperature was 45° C. were higher than those obtained by the reactions at 37° C.

Figure 8:
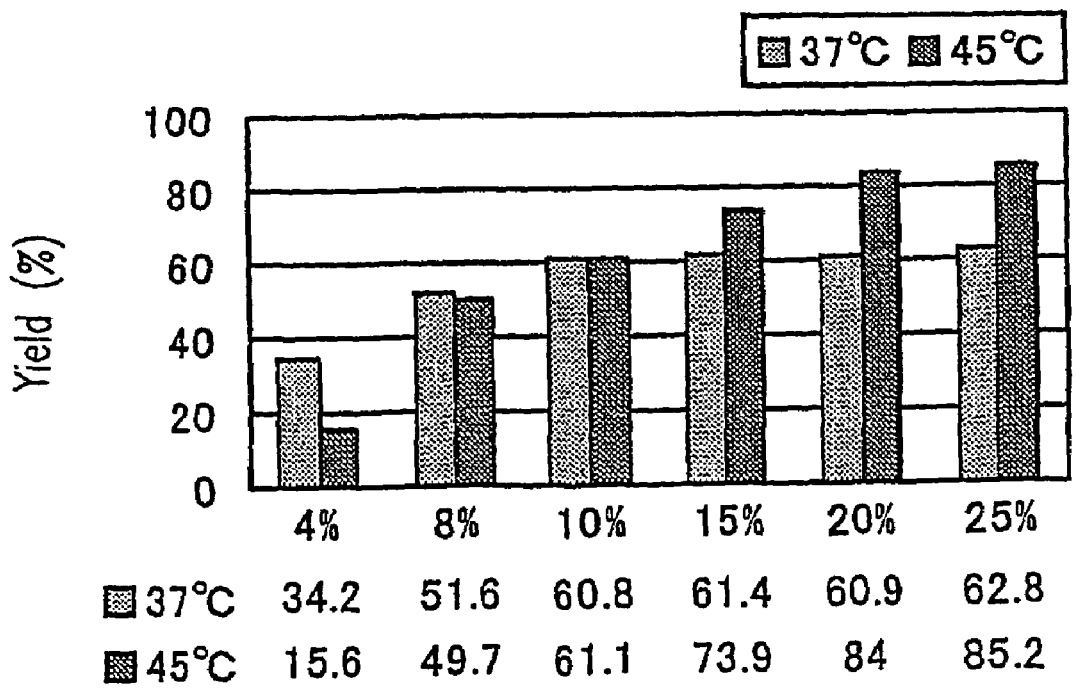
FIG. 8 is a graph showing the yields of amylose when reactions were conducted using *Leuconostoc mesenteroides*-derived sucrose phosphorylase and *Thermus aquaticus*-derived glucan phosphorylase in amounts corresponding to half the activity of the enzymes used in FIG. 7 with various initial sucrose concentrations and the reaction temperature was 45° C.

As shown in FIG. 8, under these conditions, whereas the yield of amylose was 34.2% for conventional methods, the yield was as low as 15.6% where the sucrose concentration was 4% and the reaction temperature was 45° C. However, when the proportions among the substrates and the amounts of the enzymes were not changed, and the sucrose concentration was varied between 8% and 25%, the yield of amylose was increased where the reaction temperature was 45° C. The yields of amylose obtained by the reactions where the sucrose concentration was at least 15% and the reaction temperature was 45° C. were higher than those obtained at 37° C. Thus, when *Thermus aquaticus* (extremely thermophilic bacterium)-derived glucan phosphorylase was used instead of potato-derived glucan phosphorylase, and the reactions were conducted where the sucrose concentration was at least 15%, not only could the reactions be conducted at 45° C., but also higher productivity than that in the reactions at 37° C. could be achieved.

Example 7-1 to 7-5 and Comparative Example 7-1

Amylose Synthesis using *Streptococcus mutans*-Derived Sucrose Phosphorylase and Extremely Thermophilic Bacterium-derived Glucan Phosphorylase Amylose synthesis was conducted using reaction mixtures whose compositions (at the start of the reaction) are shown in Table 8 below.

TABLE 8

| No. | Sucrose (%) | G7 (mM) | Pi (mM) | SP (U/g sucrose) | GP (U/g sucrose) | Reaction temperature |
|---|---|---|---|---|---|---|
| Comparative example 7-1 | 4 | 2 | 20 | 10 | 10 | 50° C. |
| Example 7-1 | 8 | 4 | 40 | 10 | 10 | 50° C. |
| Example 7-2 | 10 | 5 | 50 | 10 | 10 | 50° C. |
| Example 7-3 | 15 | 7.5 | 75 | 10 | 10 | 50° C. |
| Example 7-4 | 20 | 10 | 100 | 10 | 10 | 50° C. |
| Example 7-5 | 25 | 12.5 | 125 | 10 | 10 | 50° C. |

G7: Maltoheptaose
Pi: Potassium dihydrogen phosphate-disodium hydrogen phosphate buffered solution
SP: Streptococcus mutans-derived sucrose phosphorylase
GP: Thermus aquaticus-derived glucan phosphorylase Specifically, *Thermus aquaticus*-derived glucan phosphorylase obtained according to Section 2.4 above was used instead of potato-derived glucan phosphorylase.

Except for that, in comparative example 7-1 and Examples 7-1 to 7-5, amylose synthesis was conducted in the same manner as that in comparative example 3-2-1 and Examples 3-2-1 to 3-2-5.

Figure 9:
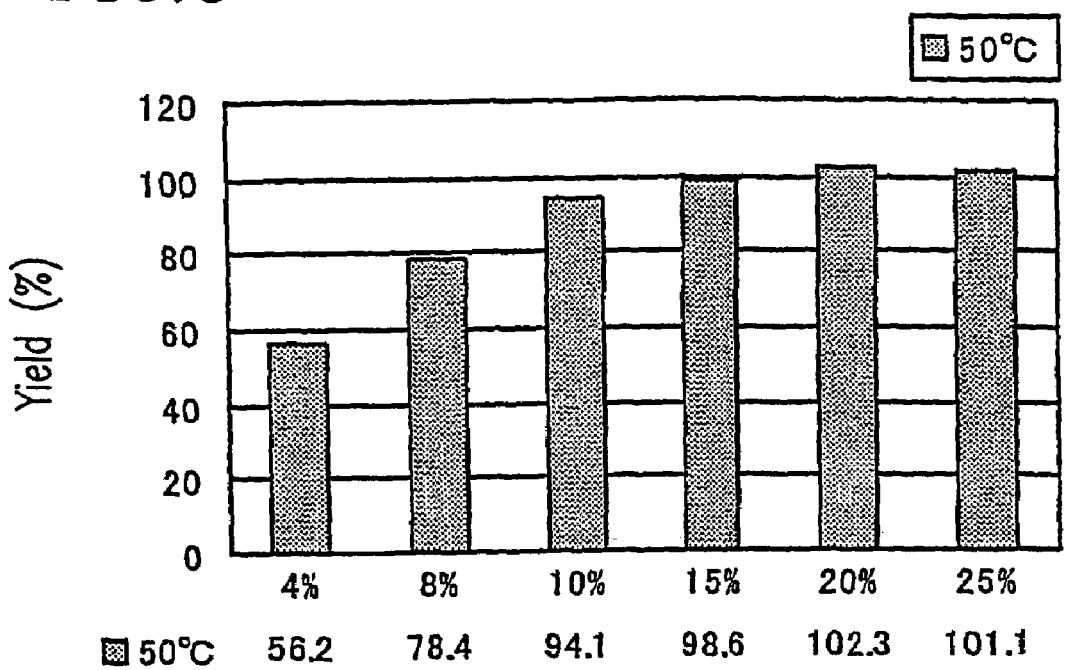
FIG. 9 is a graph showing the yields of amylose when reactions were conducted using *Streptococcus mutans* (heat-resistant bacterium)-derived sucrose phosphorylase and *Thermus aquaticus*-derived glucan phosphorylase with various initial sucrose concentrations and the reaction temperature was 50° C.

After the reaction, the yield of synthesized amylose was determined according to Section 1.6 above. The results are shown in FIG. 9.

When sucrose phosphorylase was changed from *Leuconostoc mesenteroides*-derived sucrose phosphorylase used in conventional methods to *Streptococcus mutans*-derived sucrose phosphorylase and potato-derived glucan phosphorylase was changed to *Thermus aquaticus*-derived glucan phosphorylase, and the sucrose concentration was increased from 4% to at least 8%, the reactions could be conducted at 50° C. and the yield of amylose was increased.

Specifically, under the above-described conditions, when the proportions among the substrates and the amounts of the enzymes were not changed, and the sucrose concentration was varied between 8% and 25%, the yield of amylose was increased. As shown in FIG. 9, where as the yield was 56.2% where the sucrose concentration was 4% and the reaction temperature was 50° C., the yield was 78.4% where the sucrose concentration was 8% and the reaction temperature was 50° C., and the yield was substantially 100% where the sucrose concentration was 15%. Thus, when sucrose phosphorylase was changed to *Streptococcus mutans*-derived sucrose phosphorylase and glucan phosphorylase was changed to *Thermus aquaticus*-derived glucan phosphorylase, amylose production at 50° C. was made possible.

Examples 8-1-1 to 8-2-5 as well as Comparative Examples 8-1-1 and 8-2-1

Amylose Synthesis Using *Streptococcus mutans*-derived Sucrose Phosphorylase and Extremely Thermophilic Bacterium-derived Glucan Phosphorylase with Small Amounts of Enzymes Amylose synthesis was conducted using reaction mixtures whose compositions (at the start of the reaction) are shown in Table 9 below.

TABLE 9

| No. | Sucrose (%) | G7 (mM) | Pi (mM) | SP (U/g sucrose) | GP (U/g sucrose) | Reaction temperature |
|---|---|---|---|---|---|---|
| Comparative example 8-1-1 | 4 | 2 | 20 | 5 | 5 | 45° C. |
| Example 8-1-1 | 8 | 4 | 40 | 5 | 5 | 45° C. |
| Example 8-1-2 | 10 | 5 | 50 | 5 | 5 | 45° C. |
| Example 8-1-3 | 15 | 7.5 | 75 | 5 | 5 | 45° C. |
| Example 8-1-4 | 20 | 10 | 100 | 5 | 5 | 45° C. |
| Example 8-1-5 | 25 | 12.5 | 125 | 5 | 5 | 45° C. |
| comparative example 8-2-1 | 4 | 2 | 20 | 5 | 5 | 50° C. |
| Example 8-2-1 | 8 | 4 | 40 | 5 | 5 | 50° C. |
| Example 8-2-2 | 10 | 5 | 50 | 5 | 5 | 50° C. |
| Example 8-2-3 | 15 | 7.5 | 75 | 5 | 5 | 50° C. |
| Example 8-2-4 | 20 | 10 | 100 | 5 | 5 | 50° C. |
| Example 8-2-5 | 25 | 12.5 | 125 | 5 | 5 | 50° C. |

G7: Maltoheptaose
Pi: Potassium dihydrogen phosphate-disodium hydrogen phosphate buffered solution
SP: Streptococcus mutans-derived sucrose phosphorylase
GP: Thermus aquaticus-derived glucan phosphorylase Specifically, the amounts of the enzymes were half those in comparative example 7-1, and Examples 7-1 to 7-5, and the reaction temperatures were 45° C. and 50° C. Except for that, amylose synthesis was conducted in the same manner as that in comparative example 7-1, and Examples 7-1 to 7-5.

After the reaction, the yield of synthesized amylose was determined according to Section 1.6 above. The results are shown in FIG. 10.

When sucrose phosphorylase was changed from *Leuconostoc mesenteroides*-derived sucrose phosphorylase used in conventional methods to *Streptococcus mutans*-derived sucrose phosphorylase, potato-derived glucan phosphorylase was changed to *Thermus aquaticus*-derived glucan phosphorylase, and the amounts of the enzymes were half those in the conventional methods, the yields of amylose obtained by the reactions where the sucrose concentration was at least 15% were higher in the reactions at 50° C. than those obtained by the reactions in 45° C.

Figure 10:
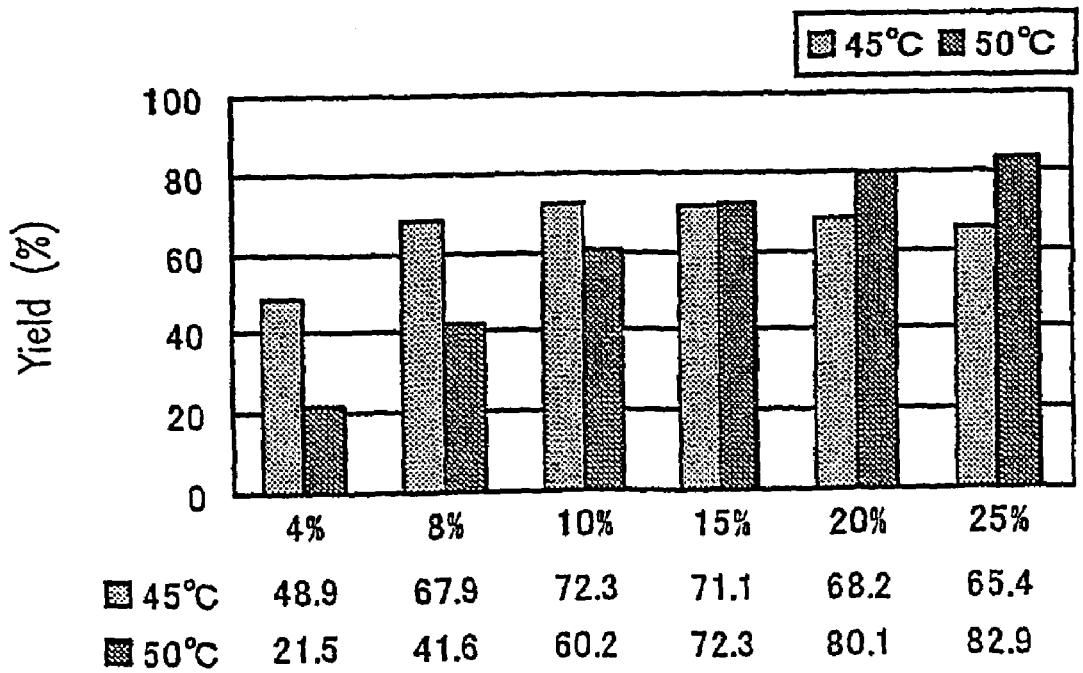
FIG. 10 is a graph showing the yields of amylose when reactions were conducted using *Streptococcus mutans*-derived sucrose phosphorylase and *Thermus aquaticus*-derived glucan phosphorylase in amounts corresponding to half the activity of the enzymes used in FIG. 9 with various initial sucrose concentrations and the reaction temperature was 50° C.

As shown in FIG. 10, whereas the yield of amylose was 48.9% where the sucrose concentration was 4% and the reaction temperature was 45° C., the yield was as low as 21.5% where the sucrose concentration was 4% and the reaction temperature was 50° C. However, the proportions among the substrates and the amounts of the enzymes were not changed and the sucrose concentration was varied between 8% and 25%, the yields of amylose obtained by the reactions at 50° C. were increased. When the sucrose concentration was at least 15%, the yields of amylose obtained by the reactions at 50° C. were higher than those obtained by the reactions at 45° C. Thus, when the reaction was conducted where *Streptococcus mutans*-derived sucrose phosphorylase and *Thermus aquaticus*-derived glucan phosphorylase were used and the sucrose concentration was at least 15%, not only could the reactions be conducted at 50° C., but also higher productivity than that obtained by the reactions at 45° C. could be realized.

Examples 9-1 to 9-5 and Comparative Example 9-1

Amylose Synthesis using *Leuconostoc mesenteroides*-Derived Sucrose Phosphorylase and *Bacillus stearothermophilus*-derived Glucan Phosphorylase Amylose synthesis was conducted using reaction mixtures whose compositions (at the start of the reaction) are shown in Table 10 below.

TABLE 10

| No. | Sucrose (%) | G7 (mM) | Pi (mM) | SP (U/g sucrose) | GP (U/g sucrose) | Reaction temperature |
|---|---|---|---|---|---|---|
| Comparative example 9-1 | 4 | 2 | 20 | 10 | 10 | 45° C. |
| Example 9-1 | 8 | 4 | 40 | 10 | 10 | 45° C. |
| Example 9-2 | 10 | 5 | 50 | 10 | 10 | 45° C. |
| Example 9-3 | 15 | 7.5 | 75 | 10 | 10 | 45° C. |
| Example 9-4 | 20 | 10 | 100 | 10 | 10 | 45° C. |
| Example 9-5 | 25 | 12.5 | 125 | 10 | 10 | 45° C. |

G7: Maltoheptaose
Pi: Potassium dihydrogen phosphate-disodium hydrogen phosphate buffered solution
SP: Leuconostoc mesenteroides-derived sucrose phosphorylase
GP: Bacillus stearothermophilus-derived glucan phosphorylase Specifically, *Bacillus stearothermophilus*-derived glucan phosphorylase was used instead of *Thermus aquaticus*-derived glucan phosphorylase. Except for that, amylose synthesis was conducted in the same manner as that in comparative example 5-1 and Examples 5-1 to 5-5.

Figure 11:
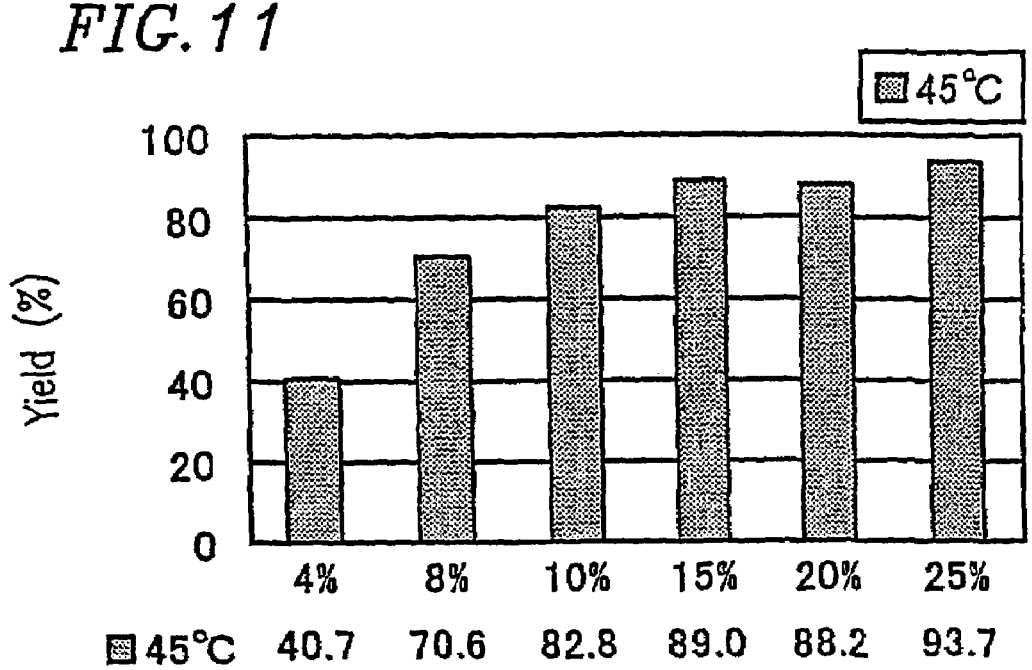
FIG. 11 is a graph showing the yields of amylose when reactions were conducted using *Leuconostoc mesenteroides*-derived sucrose phosphorylase and *Bacillus stearothermophilus*-derived glucan phosphorylase with various initial sucrose concentrations and the reaction temperature was 45° C.

After the reaction, the yield of synthesized amylose was determined according to Section 1.6 above. The results are shown in FIG. 11.

When *Bacillus stearothermophilus*-derived glucan phosphorylase was used, and the sucrose concentration was increased from 4% for conventional methods to at least 8%, the reactions could be conducted at 45° C. and the yields of amylose were increased.

Specifically, under the above-described conditions, the proportions among the substrates and the amounts of the enzymes were not changed, and the sucrose concentration was varied between 8% and 25%, the yield of amylose was increased. As shown in FIG. 11, whereas the yield was 40.7% where the sucrose concentration was 4% and the reaction temperature was 45° C., the yield was 70.6% where the sucrose concentration was 8% and the reaction temperature was 45° C. Further, when the sucrose concentration was at least 15%, the yield of amylose was about 90%. Thus, it was confirmed that when *Bacillus stearothermophilus*-derived glucan phosphorylase was used instead of potato-derived glucan phosphorylase, amylose synthesis could be conducted at 45° C.

Examples 10-1 to 10-5 and Comparative Examples 10-1 to 10-7

Amylose Synthesis using *Leuconostoc mesenteroides*-derived Sucrose Phosphorylase and *Bacillus stearothermophilus*-derived Glucan Phosphorylase with Small Amounts of Enzymes Amylose synthesis was conducted using reaction mixtures whose compositions (at the start of the reaction) are shown in Table 11 below.

TABLE 11

| No. | Sucrose (%) | G7 (mM) | Pi (mM) | SP (U/g sucrose) | GP (U/g sucrose) | Reaction temperature |
|---|---|---|---|---|---|---|
| Comparative example 10-1 | 4 | 2 | 20 | 5 | 5 | 37° C. |
| Comparative example 10-2 | 8 | 4 | 40 | 5 | 5 | 37° C. |
| Comparative example 10-3 | 10 | 5 | 50 | 5 | 5 | 37° C. |
| Comparative example 10-4 | 15 | 7.5 | 75 | 5 | 5 | 37° C. |
| Comparative example 10-5 | 20 | 10 | 100 | 5 | 5 | 37° C. |
| Comparative example 10-6 | 25 | 12.5 | 125 | 5 | 5 | 37° C. |
| Comparative example 10-7 | 4 | 2 | 20 | 5 | 5 | 45° C. |
| Example 10-1 | 8 | 4 | 40 | 5 | 5 | 45° C. |
| Example 10-2 | 10 | 5 | 50 | 5 | 5 | 45° C. |
| Example 10-3 | 15 | 7.5 | 75 | 5 | 5 | 45° C. |
| Example 10-4 | 20 | 10 | 100 | 5 | 5 | 45° C. |
| Example 10-5 | 25 | 12.5 | 125 | 5 | 5 | 45° C. |

G7: Maltoheptaose
Pi: Potassium dihydrogen phosphate-disodium hydrogen phosphate buffered solution
SP: Leuconostoc mesenteroides-derived sucrose phosphorylase
GP: Bacillus stearothermophilus-derived glucan phosphorylase Specifically, in Examples 10-1 to 10-5 and comparative examples 10-1 to 10-7, the reactions were conducted where the amounts of the enzymes were half those in comparative examples 9-1 and Examples 9-1 to 9-5, and the reaction temperatures were 37° C. and 45° C. Except for that, amylose synthesis was conducted in the same manner as that in comparative example 9-1 and Examples 9-1 to 9-5.

After the reaction, the yield of synthesized amylose was determined according to Section 1.6 above. The results are shown in FIG. 12.

When *Bacillus stearothermophilus*-derived glucan phosphorylase was used and the sucrose concentration was at least 15%, the yields of amylose obtained by the reactions at 45° C. were no less than those obtained by the reactions at 37° C.

Figure 12:
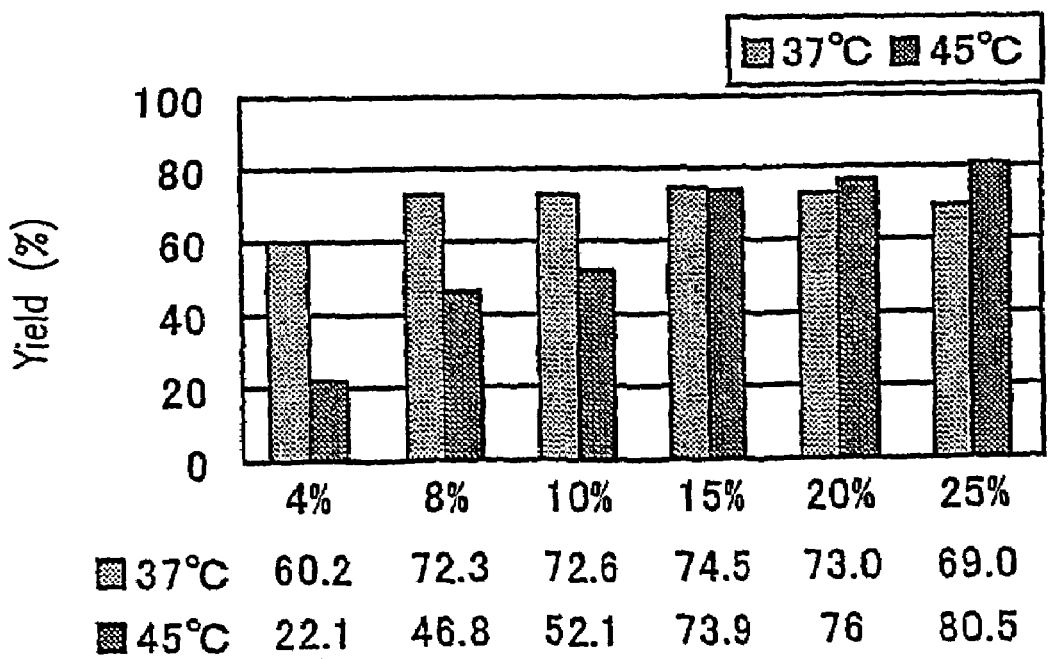
FIG. 12 is a graph showing the yields of amylose when reactions were conducted using *Leuconostoc mesenteroides*-derived sucrose phosphorylase and *Bacillus stearothermophilus*-derived glucan phosphorylase in amounts corresponding to half the activity of the enzymes used in FIG. 11 with various initial sucrose concentrations and the reaction temperatures were 37° C. and 45° C.

As shown in FIG. 12, under these conditions, whereas the yield of amylose was 60.2% for conventional methods, the yield was as low as 22.1% where the sucrose concentration was 4% and the reaction temperature was 45° C. However, when the proportions among the substrates and the amounts of the enzymes were not changed and the sucrose concentration was varied between 8% and 25%, the yields of amylose obtained by the reactions at 45° C. were increased. When the sucrose concentration was at least 15%, the yields of amylose obtained by the reactions at 45° C. were higher than those obtained by the reactions at 37° C. Thus, when *Bacillus stearothermophilus*-derived glucan phosphorylase was used instead of potato-derived glucan phosphorylase, and the sucrose concentration was at least 15%, not only could the reactions be conducted at 45° C., but also higher productivity than that obtained by the reactions at 37° C. could be realized.

Examples 11-1 to 11-5 and Comparative Example 11-1

Amylose Synthesis using *Streptococcus mutans*-derived Sucrose Phosphorylase and *Bacillus stearothermophilus*-derived Glucan Phosphorylase Amylose synthesis was conducted using reaction mixtures whose compositions (at the start of the reaction) are shown in Table 12 below.

TABLE 12

| No. | Sucrose (%) | G7 (mM) | Pi (mM) | SP (U/g sucrose) | GP (U/g sucrose) | Reaction temperature |
|---|---|---|---|---|---|---|
| Comparative example 11-1 | 4 | 2 | 20 | 10 | 10 | 50° C. |
| Example 11-1 | 8 | 4 | 40 | 10 | 10 | 50° C. |
| Example 11-2 | 10 | 5 | 50 | 10 | 10 | 50° C. |
| Example 11-3 | 15 | 7.5 | 75 | 10 | 10 | 50° C. |
| Example 11-4 | 20 | 10 | 100 | 10 | 10 | 50° C. |
| Example 11-5 | 25 | 12.5 | 125 | 10 | 10 | 50° C. |

G7: Maltoheptaose
Pi: Potassium dihydrogen phosphate-disodium hydrogen phosphate buffered solution
SP: Streptococcus mutans-derived sucrose phosphorylase
GP: Bacillus stearothermophilus-derived glucan phosphorylase Specifically, *Streptococcus mutans*-derived sucrose phosphorylase obtained according to Section 2.5 above was used instead of *Leuconostoc mesenteroides*-derived sucrose phosphorylase, and the enzyme reactions were conducted at 50° C. Except for that, in comparative example 11-1 and Examples 11-1 to 11-5, amylose synthesis was conducted in the same manner as that in comparative example 9-1 and Examples 9-1 to 9-5.

Figure 13:
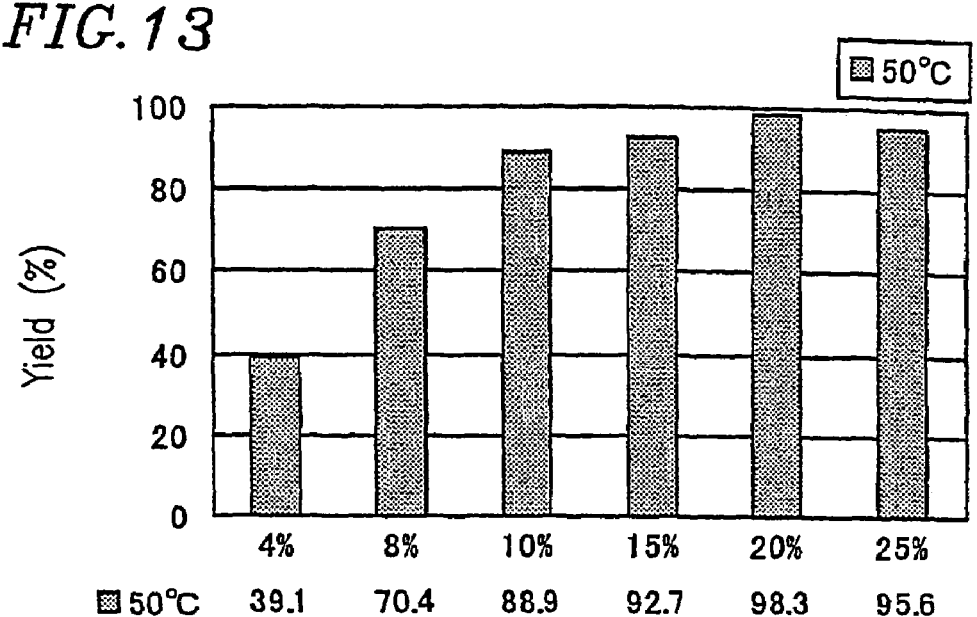
FIG. 13 is a graph showing the yields of amylose when reactions were conducted using *Streptococcus mutans* (heat-resistant bacterium)-derived sucrose phosphorylase and *Bacillus stearothermophilus*-derived glucan phosphorylase with various initial sucrose concentrations and the reaction temperature was 50° C.

After the reaction, the yield of synthesized amylose was determined according to Section 1.6 above. The results are shown in FIG. 13.

When sucrose phosphorylase was changed from *Leuconostoc mesenteroides*-derived sucrose phosphorylase used in conventional methods to *Streptococcus mutans*-derived sucrose phosphorylase and potato-derived glucan phosphorylase was changed to *Bacillus stearothermophilus*-derived glucan phosphorylase, and the sucrose concentration was increased from 4% to at least 8%, the reactions could be conducted at 50° C. and the yields of amylose were increased.

Specifically, under the above-described conditions, when the proportions among the substrates and the amounts of the enzymes were not changed and the sucrose concentration was varied between 8% and 25%, the yield of amylose was increased. As shown in FIG. 13, where as the yield was 39.1% where the sucrose concentration was 4% and the reaction temperature was 50° C., the yield was 70.4% where the sucrose concentration was 8% and the reaction temperature was 50° C., and the yield of amylose was at least 90% where the sucrose concentration was 15%. Thus, when *Streptococcus mutans*-derived sucrose phosphorylase used as sucrose phosphorylase and *Bacillus stearothermophilus*- derived glucan phosphorylase was used as glucan phosphorylase, amylose production at 50° C. was made possible.

Examples 12-1-1 to 12-2-5 and Comparative Example 12-1-1 and 12-2-1

Amylose Synthesis Using *Streptococcus mutans*-derived Sucrose Phosphorylase and *Bacillus stearothermophilus*-derived Glucan Phosphorylase with Small Amounts of Enzymes Amylose synthesis was conducted using reaction mixtures whose compositions (at the start of the reaction) are shown in Table 13 below.

TABLE 13

| No. | Sucrose (%) | G7 (mM) | Pi (mM) | SP (U/g sucrose) | GP (U/g sucrose) | Reaction temperature |
|---|---|---|---|---|---|---|
| Comparative example 12-1-1 | 4 | 2 | 20 | 5 | 5 | 45° C. |
| Example 12-1-1 | 8 | 4 | 40 | 5 | 5 | 45° C. |
| Example 12-1-2 | 10 | 5 | 50 | 5 | 5 | 45° C. |
| Example 12-1-3 | 15 | 7.5 | 75 | 5 | 5 | 45° C. |
| Example 12-1-4 | 20 | 10 | 100 | 5 | 5 | 45° C. |
| Example 12-1-5 | 25 | 12.5 | 125 | 5 | 5 | 45° C. |
| Comparative example 12-2-1 | 4 | 2 | 20 | 5 | 5 | 50° C. |
| Example 12-2-1 | 8 | 4 | 40 | 5 | 5 | 50° C. |
| Example 12-2-2 | 10 | 5 | 50 | 5 | 5 | 50° C. |
| Example 12-2-3 | 15 | 7.5 | 75 | 5 | 5 | 50° C. |
| Example 12-2-4 | 20 | 10 | 100 | 5 | 5 | 50° C. |
| Example 12-2-5 | 25 | 12.5 | 125 | 5 | 5 | 50° C. |

G7: Maltoheptaose
Pi: Potassium dihydrogen phosphate-disodium hydrogen phosphate buffered solution
SP: Streptococcus mutans-derived sucrose phosphorylase
GP: Bacillus stearothermophilus-derived glucan phosphorylase Specifically, the amounts of the enzymes were half those in comparative example 11-1 and Examples 11-1 to 11-5 and the reaction temperatures were 45° C. and 50° C. Except for that, amylose synthesis was conducted in the same manner as that in comparative example 11-1 and Examples 11-1 to 11-5.

After the reaction, the yield of synthesized amylose was determined according to Section 1.6 above. The results are shown in FIG. 14.

When sucrose phosphorylase was changed from *Leuconostoc mesenteroides*-derived sucrose phosphorylase used in conventional methods to *Streptococcus mutans*-derived sucrose phosphorylase, potato-derived glucan phosphorylase was changed to *Bacillus stearothermophilus*-derived glucan phosphorylase, and the amounts of the enzymes were half that of conventional methods, the yields of amylose where the sucrose concentration was at least 15% were higher in the reactions at 50° C. than those in the reactions at 45° C.

Figure 14:
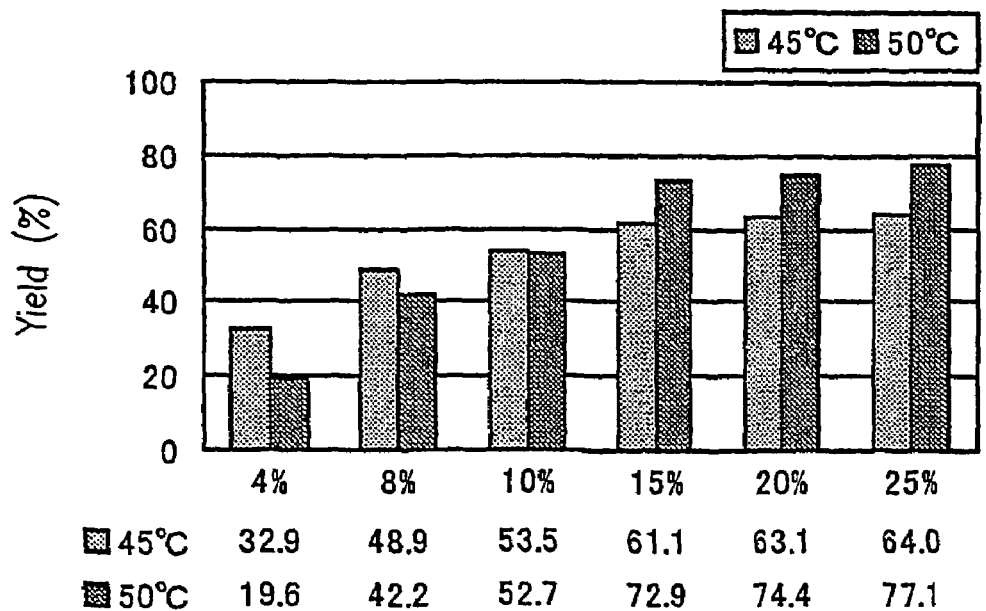
FIG. 14 is a graph showing the yields of amylose when reactions were conducted using *Streptococcus mutans*-derived sucrose phosphorylase and *Bacillus stearothermophilus*-derived glucan phosphorylase in amounts corresponding to half the activity of the enzymes used in FIG. 13 with various initial sucrose concentrations and the reaction temperatures were 45° C. and 50° C.

As shown in FIG. 14, whereas the yield of amylose was 32.9% where the sucrose concentration was 4% and the reaction temperature was 45° C., the yield was as low as 19.6% where the sucrose concentration was 4% and the reaction temperature was 50° C. However, when the proportions among the substrates and the amounts of the enzymes were not changed and the sucrose concentration was varied between 8% and 25%, the yields of amylose obtained by the reactions at 50° C. were increased. The yields of amylose where the sucrose concentration was at least 15% were higher in the reactions at 50° C. than those in the reactions at 45° C. Thus, when the reactions were conducted where *Streptococcus mutans*-derived sucrose phosphorylase and *Bacillus stearothermophilus*-derived glucan phosphorylase were used and the sucrose concentration was at least 15%, not only could the reactions be conducted at 50° C., but also higher productivity than that of the reactions at 45° C. could be realized.

Example 13

Amylose Synthesis under High Temperature Conditions

Amylose synthesis was conducted using reaction mixtures whose compositions (at the start of the reaction) are shown in Table 14 below.

TABLE 14

| No. | Sucrose (%) | G7 (mM) | Pi (mM) | SP (U/g sucrose) | GP (U/g sucrose) | Reaction temperature |
|---|---|---|---|---|---|---|
| Comparative example 13-1 | 4 | 2 | 20 | 50 | 50 | 65° C. |
| Example 13-1 | 50 | 25 | 250 | 50 | 50 | 65° C. |
| Comparative example 13-2 | 4 | 2 | 20 | 50 | 50 | 65° C. |
| Example 13-2 | 50 | 25 | 250 | 50 | 50 | 65° C. |

G7: Maltoheptaose
Pi: Potassium dihydrogen phosphate-disodium hydrogen phosphate buffered solution
SP: Streptococcus mutans-derived sucrose phosphorylase
GP: Potato-derived glucan phosphorylase (comparative example 13-1 and Example 13-1)

*Thermus aquaticus*-derived glucan phosphorylase (comparative example 13-2 and Example 13-2)

Specifically, the amounts of the enzymes were five times as great as that of comparative example 3-1-1, and the reaction temperature was 65° C. Except for that, in comparative example 13-1, amylose synthesis was conducted in the same manner as that in comparative example 3-1-1. In Example 13-1, amylose synthesis was conducted where the proportions among the substrates and the amounts of the enzymes in comparative example 3-1-1 were not changed and the sucrose concentration was increased to 50%. Further, in comparative example 13-2 and Example 13-2, amylose synthesis was conducted where *Thermus aquaticus*-derived glucan phosphorylase prepared according to Section 2.4 above was used instead of potato-derived glucan phosphorylase in comparative example 13-1 and Example 13-1.

Figure 15:
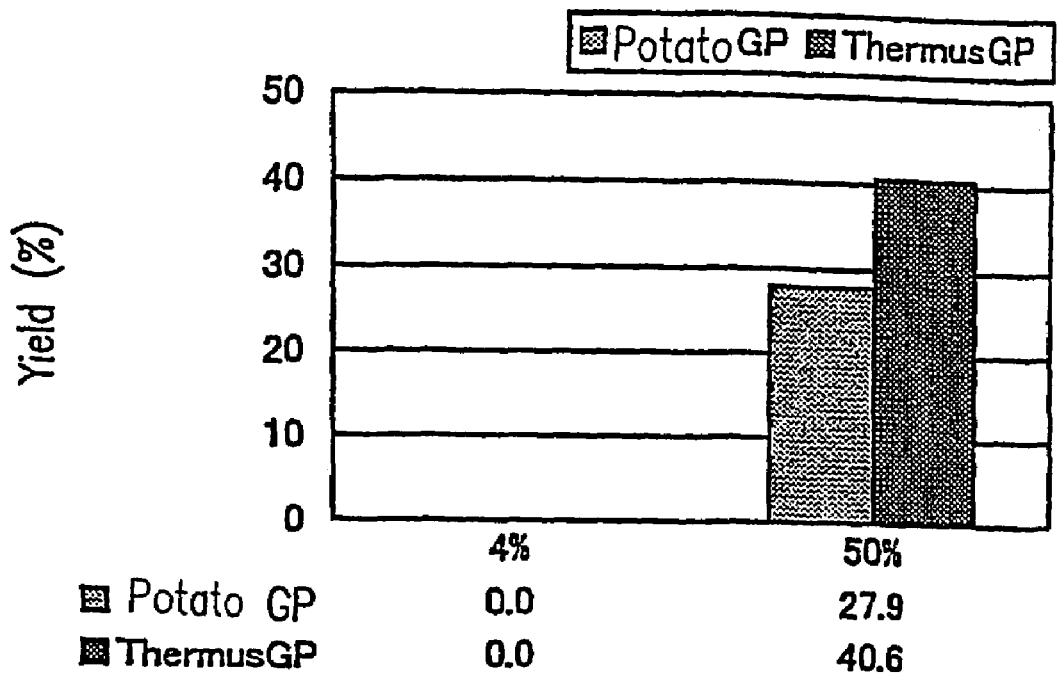
FIG. 15 is a graph showing the yield of amylose when a reaction was conducted using *Streptococcus mutans* (heat-resistant bacterium)-derived sucrose phosphorylase and potato-derived glucan phosphorylase or *Thermus aquaticus*-derived glucan phosphorylase where the initial sucrose concentration was 50% at the start of the reaction and the reaction temperature was 65° C.

After the reaction, the yield of synthesized amylose was determined according to Section 1.6 above. The results are shown in FIG. 15.

In conventional methods, regardless of the glucan phosphorylases used, no amylose can be synthesized in the reactions at 65° C. When the sucrose concentration was increased, amylose could be produced at 65° C.

Example 14

Amylose Production Where Maltotetraose was Used as a Primer

In the above-described Examples, maltoheptaose was utilized as a primer in amylose production. However, high-purity malto-oligosaccharide is expensive and is not distributed to an extent that it is industrially available. Maltotetraose-containing syrup is an inexpensive malto-oligosaccharide. However, such syrup contains glucose, maltose, maltotriose, and the like which are not believed to function as a primer. Further, maltotetraose has a lower affinity to glucan phosphorylase than that of maltoheptaose.

It is not clear whether or not such syrup can be used to conduct a glucan synthesis reaction. Such research has not been reported. Therefore, the present inventors studied whether or not syrup containing maltotetraose instead of maltoheptaose can be used to synthesize amylose.

Specifically, Tetrup H (Hayashibara Shoji, Inc.) containing at least 70% maltotetraose was used. Except for that, amylose was synthesized in the same manner as that in Example 7-2. As a result, it was confirmed that high molecular weight amylose could be produced even using Tetrup H.

Example 15

Purification of Amylose using Membrane Filtration

2% sucrose, 10 mM inorganic phosphate, 50 U/g sucrose *Leuconostoc mesenteroides*-derived sucrose phosphorylase (manufactured by Oriental Yeast Co., Ltd.), 50 U/g sucrose recombinant potato tuber-derived glucan phosphorylase prepared according to Section 2.2 above, and maltoheptaose as a primer were used to synthesize amylose at 37° C. for 18 hours. In this case, the reaction volume was 2,000 ml.

2,000 ml of the amylose solution after the reaction was concentrated to 1,200 ml using an ultrafiltration membrane (UF membrane unit; manufactured by Daicel Chemical Industries Ltd.) with a molecular weight cutoff of 30,000. Thereafter, diafiltration was conducted against 10 L of distilled water, and distilled water was added to obtain 2,000 ml. The fructose content and the weight-average molecular weight of amylose were measured before and after the membrane filtration. The results are shown in Table 15.

TABLE 15

Removal of fructose by membrane filtration

| No. | Fructose (mM) | Weight-average molecular weight (KDa) |
|---|---|---|
| Before membrane filtration | 57.5 | 715 |
| After membrane filtration | <0.1 | 712 |

As shown in Table 15, it was confirmed that an ultrafiltration membrane can be used to purify amylose, so that fructose present in a reaction solution could be removed. It was confirmed that the weight-average molecular weight of amylose was not much changed by the membrane filtration.

Thus, by purifying amylose using an ultrafiltration membrane, amylose can be purified without a number of organic solvents, such as butanol, methanol, ethanol, ether, and the like, which are conventionally used in purification of amylose.

Examples 16-1 to 16-7 and Comparative Example 16-1

Amylose Synthesis where *Leuconostoc mesenteroides*-derived Sucrose Phosphorylase and Potato-derived Glucan Phosphorylase were Used and the Ratio of Sucrose Concentration to Inorganic Phosphate Concentration was Changed Amylose synthesis was conducted using reaction mixtures whose compositions (at the start of the reaction) are shown in Table 16 below.

TABLE 16

| No. | Sucrose (mM) | G7 (mM) | Pi (mM) | SP (U/g sucrose) | GP (U/g sucrose) | Reaction temperature |
|---|---|---|---|---|---|---|
| Comparative example 16-1 | 125 | 0.35 | 7.2 | 20 | 20 | 37° C. |
| Example 16-1 | 125 | 0.35 | 10 | 20 | 20 | 37° C. |
| Example 16-2 | 125 | 0.35 | 20 | 20 | 20 | 37° C. |
| Example 16-3 | 125 | 0.35 | 30 | 20 | 20 | 37° C. |
| Example 16-4 | 125 | 0.35 | 50 | 20 | 20 | 37° C. |
| Example 16-5 | 125 | 0.35 | 75 | 20 | 20 | 37° C. |
| Example 16-6 | 125 | 0.35 | 100 | 20 | 20 | 37° C. |
| Example 16-7 | 125 | 0.35 | 125 | 20 | 20 | 37° C. |

G7: Maltoheptaose
Pi: Potassium dihydrogen phosphate-disodium hydrogen phosphate buffered solution
SP: Leuconostoc mesenteroides-derived sucrose phosphorylase
GP: Potato-derived glucan phosphorylase Specifically, sucrose, inorganic phosphate, *Leuconostoc mesenteroides*-derived sucrose phosphorylase, potato tuber-derived glucan phosphorylase prepared according to Section 2.1 above and maltoheptaose were dissolved in 100 mM citrate buffered solution (pH 7.0) to obtain a solution containing 125 mM sucrose, 20 U/g sucrose *Leuconostoc mesenteroides*-derived sucrose phosphorylase, 20 U/g sucrose potato tuber-derived glucan phosphorylase, 0.35 mM maltoheptaose, and 7.2 mM inorganic phosphate (comparative example 16-1) or 10 to 125 mM inorganic phosphate (Example 16-1 to 16-7). This solution was allowed to react at 37° C. for 4 hours to synthesize amylose. The reaction volume was 1 ml.

After the reaction, the yield of synthesized amylose was determined according to Section 1.6 above. The results are shown in FIG. 16.

Figure 16:
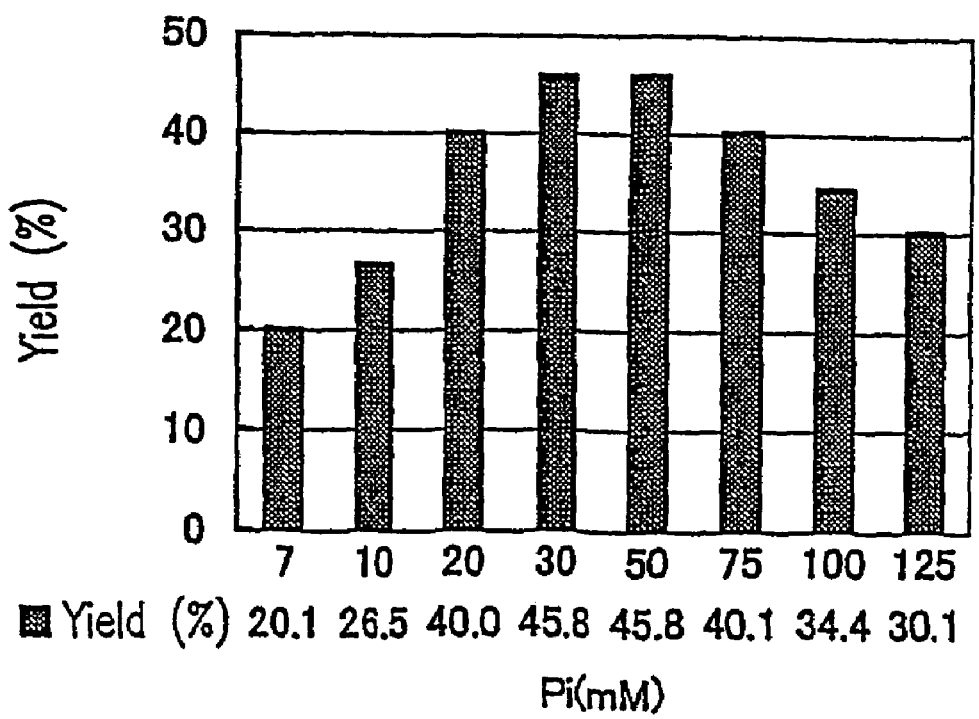
FIG. 16 is a graph showing the yields of amylose when reactions were conducted using *Leuconostoc mesenteroides*-derived sucrose phosphorylase and potato-derived glucan phosphorylase with various initial inorganic phosphate concentrations and the reaction temperature was 37° C.

As shown in FIG. 16, when 7.2 mM inorganic phosphate was added to and allowed to react with 125 mM sucrose, the yield of amylose was as low as 20.1%, but when at least 10 mM inorganic phosphate was added to and allowed to react with 125 mM sucrose, the yield was increased. Further, when 20 to 75 mM inorganic phosphate was added to and allowed to react with 125 mM sucrose, the yield was at least 40%.

Examples 17-1 to 17-7 and Comparative Example 17-1

Amylose Synthesis where *Streptococcus mutans*-derived Sucrose Phosphorylase and Potato-Derived Glucan Phosphorylase were Used and the Ratio of Sucrose Concentration to Inorganic Phosphate Concentration was Changed Amylose synthesis was conducted using reaction mixtures whose compositions (at the start of the reaction) are shown in Table 17 below.

TABLE 17

| No. | Sucrose (mM) | G7 (mM) | Pi (mM) | SP (U/g sucrose) | GP (U/g sucrose) | Reaction temperature |
|---|---|---|---|---|---|---|
| Comparative example 17-1 | 125 | 0.35 | 7.2 | 20 | 20 | 45° C. |
| Example 17-1 | 125 | 0.35 | 10 | 20 | 20 | 45° C. |
| Example 17-2 | 125 | 0.35 | 20 | 20 | 20 | 45° C. |
| Example 17-3 | 125 | 0.35 | 30 | 20 | 20 | 45° C. |

TABLE 17-continued

| No. | Sucrose (mM) | G7 (mM) | Pi (mM) | SP (U/g sucrose) | GP (U/g sucrose) | Reaction temperature |
|---|---|---|---|---|---|---|
| Example 17-4 | 125 | 0.35 | 50 | 20 | 20 | 45° C. |
| Example 17-5 | 125 | 0.35 | 75 | 20 | 20 | 45° C. |
| Example 17-6 | 125 | 0.35 | 100 | 20 | 20 | 45° C. |
| Example 17-7 | 125 | 0.35 | 125 | 20 | 20 | 45° C. |

G7: Maltoheptaose
Pi: Potassium dihydrogen phosphate-disodium hydrogen phosphate buffered solution
SP: Streptococcus mutans-derived sucrose phosphorylase
GP: Potato-derived glucan phosphorylase Specifically, in Examples 17-1 to 17-7 and comparative example 17-1, *Streptococcus mutans*-derived sucrose phosphorylase was used instead of *Leuconostoc mesenteroides*-derived sucrose phosphorylase and the reaction temperature was 45° C. Except for that, amylose was synthesized in the same manner as that in Examples 16-1 to 16-7 and comparative example 17-1.

After the reaction, the yield of synthesized amylose was determined according to Section 1.6 above. The results are shown in FIG. 17.

Figure 17:
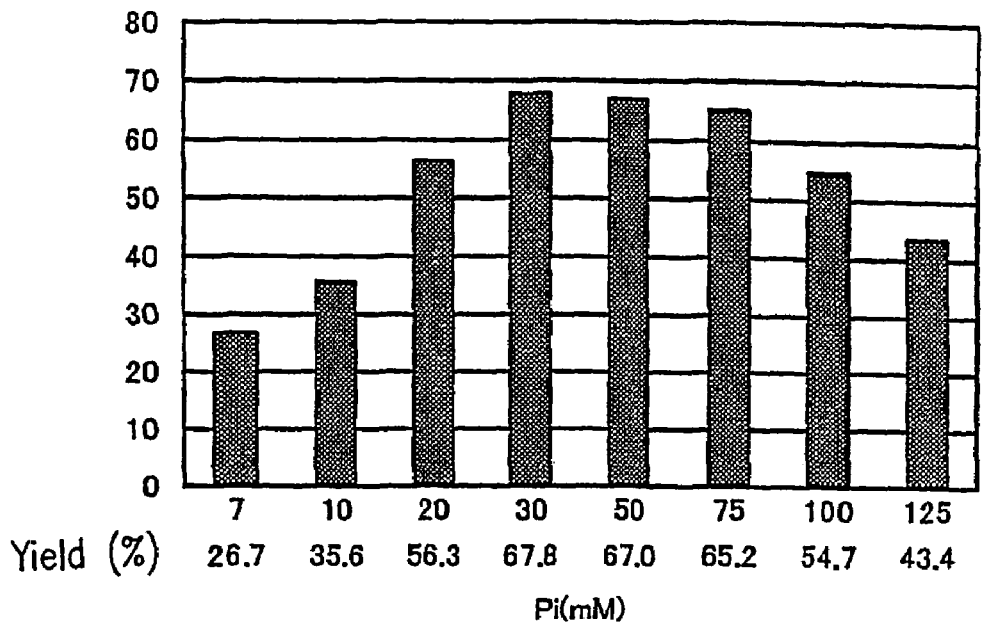
FIG. 17 is a graph showing the yields of amylose when reactions were conducted using *Streptococcus mutans* (heat-resistant bacterium)-derived sucrose phosphorylase and potato-derived glucan phosphorylase with various initial inorganic phosphate concentrations and the reaction temperature was 45° C.

As shown in FIG. 17, when 7.2 mM inorganic phosphate was added to and allowed to react with 125 mM sucrose, the yield of amylose was as low as 26.7%, but when at least 10 mM inorganic phosphate was added to and allowed to react with 125 mM sucrose, the yield was increased. Further, when 20 to 75 mM inorganic phosphate was added to and allowed to react with 125 mM sucrose, the yield was at least 50 to 60%.

Thus, although the maximum value of the sucrose-phosphate ratio used in conventional methods does not lead to a high level of productivity and is disadvantageous for industrial production, about twice this level of productivity could be achieved by setting the maximum value of the sucrose-phosphate ratio within a predetermined range.

Example 18

The Heat-resistance of *Streptococcus mutans*-derived Sucrose Phosphorylase in the Presence of Sucrose Sucrose was added to and dissolved in liquid, which is prepared by destroying *E. coli* which produces sucrose phosphorylase according to Section 2.5 above, so as to obtain solutions having a final sucrose concentration of 4%, 8%, 12%, 16%, 20%, 25% or 30% relative to the solutions after the dissolution. Sucrose phosphorylase enzyme liquid without sucrose was used as a control (0% sucrose). These solutions were heated in a water bath at 55° C. The solutions were sampled at the start of the heating (0 minutes), and at 30 minutes, 60 minutes and 90 minutes after the start of the heating to measure the activity of sucrose phosphorylase in accordance with the method described herein.

Based on the measured activity, the residual activity was calculated.

The residual activity was calculated as follows:

(Residual activity (%))={(the sucrose phosphorylase activity of each sample)/(the sucrose phosphorylase activity at 0 minutes after heating)}×100

Figure 18:
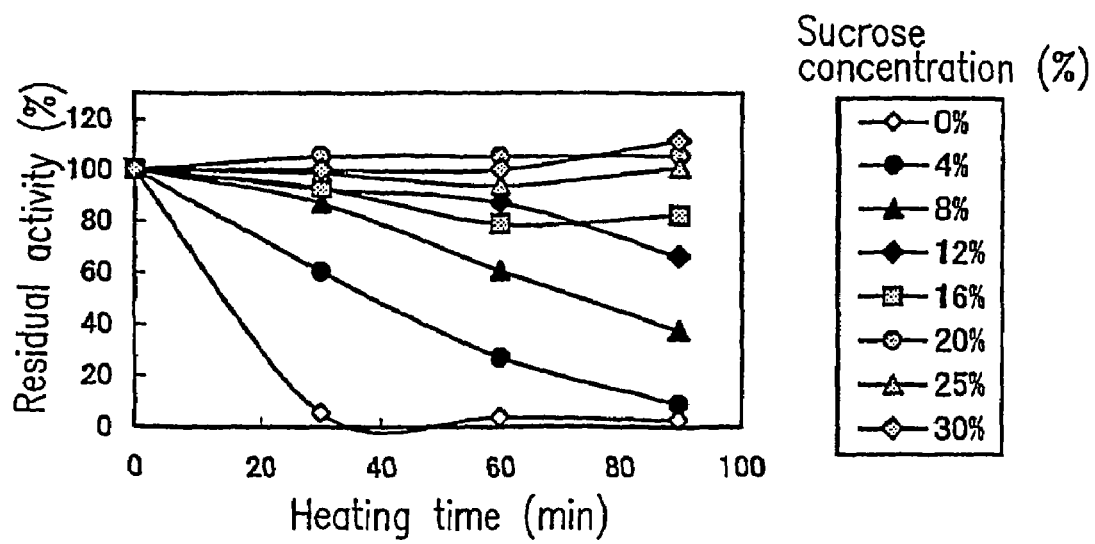
FIG. 18 is a graph showing the residual activity of a recombinant *Streptococcus mutans*-derived sucrose phosphorylase which was heated at 55° C. in sucrose solutions of various sucrose concentrations.

The results for residual activity are shown in FIG. 18. As a result, the following was found. When sucrose was not present (0%), the activity was reduced to about 10% after 30-minute heating at 55° C.

When at least 4% sucrose was present, the residual activity was at least 50% after the 30-minute heating. Particularly, when at least 8% sucrose was present, the residual activity was at least 80% even after the 30-minute heating.

Example 19

The Heat-resistance of *Leuconostoc mesenteroides*-derived Sucrose Phosphorylase in the Presence of Sucrose Sucrose was added to and dissolved in an enzyme liquid containing *Leuconostoc mesenteroides*-derived sucrose phosphorylase (purchased from Oriental Yeast Co., Ltd.) so as to obtain solutions having a final sucrose concentration of 12%, 16%, 20%, 25% or 30% relative to the solutions after the dissolution. Sucrose phosphorylase enzyme liquid without sucrose was used as a control (0% sucrose). These solutions were heated in a water bath at 50° C. The solutions were sampled at the start of the heating (0 minutes), and at 30 minutes, 60 minutes and 90 minutes after the start of the heating to measure the activity of sucrose phosphorylase in accordance with the method described herein.

Based on the measured activity, the residual activity was calculated in accordance with the above-described formula.

Figure 19:
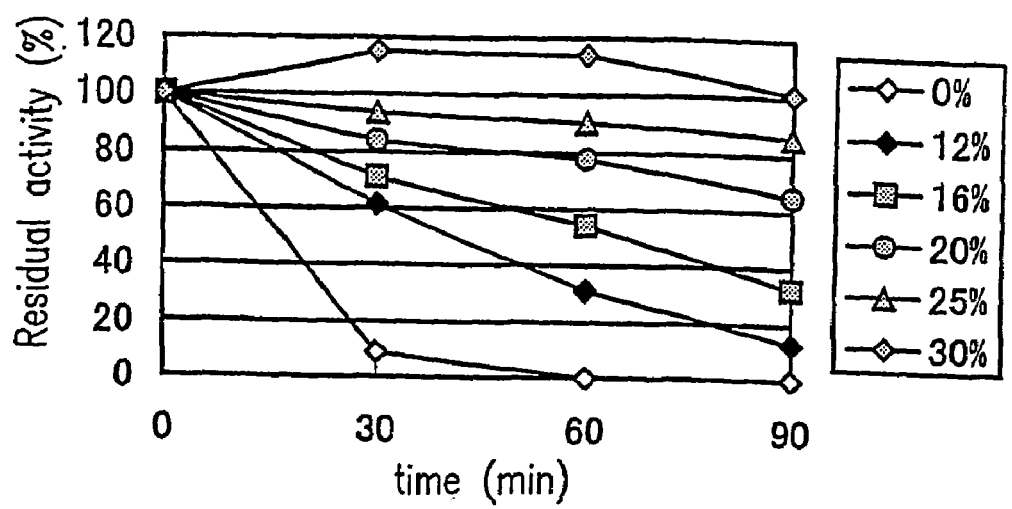
FIG. 19 is a graph showing the residual activity of *Leuconostoc mesenteroides*-derived sucrose phosphorylase which was heated at 55° C. in sucrose solutions of various sucrose concentrations.

The results for residual activity are shown in FIG. 19. As a result, the following was found. When sucrose was not present (0%), the activity was reduced to about 10% after 30-minute heating at 50° C.

When at least 12% sucrose was present, the residual activity was at least 50% after the 30-minute heating. Particularly, when at least 20% sucrose was present, the residual activity was at least 80% even after the 30-minute heating.

Comparative Example 20

The Effect of Fructose on the Stability of Sucrose Phosphorylase

In addition to sucrose, fructose, inorganic phosphate, and glucose-1-phosphate are substrates for sucrose phosphorylase. The effect of fructose on the stability of sucrose phosphorylase was studied in the following manner.

Fructose was added to and dissolved in a sucrose phosphorylase enzyme liquid containing *S. mutans*-derived sucrose phosphorylase prepared according to Section 2.5 above to obtain a solution having a final concentration of 5% or 10% relative to the solution after the dissolution. A sucrose phosphorylase enzyme liquid without fructose was used as a control (0% sucrose). Also, as control, the case where sucrose was added to the same concentration was studied. These solutions were heated in a water bath at 55° C. The solutions were sampled at the start of the heating (0 minutes), and at 30 minutes, 60 minutes and 90 minutes after the start of the heating to measure the activity of sucrose phosphorylase in accordance with the method described herein.

Based on the measured activity, the residual activity was calculated.

Figure 20:
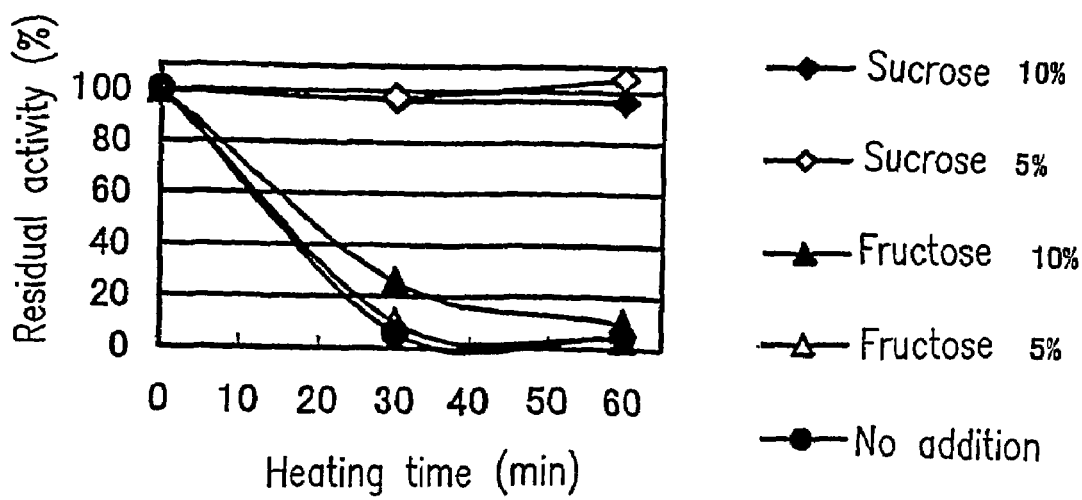
FIG. 20 is a graph showing the effect of sucrose or fructose on the stability of sucrose phosphorylase.

The results for the residual activity are shown in FIG. 20. As a result, fructose was not recognized as having the effect of stabilizing sucrose phosphorylase as shown for sucrose.

Comparative Example 21

The Effect of Inorganic Phosphate on the Stability Sucrose Phosphorylase

The effect of inorganic phosphate on the stability of sucrose phosphorylase was studied in the following manner.

Sodium phosphate was added to and dissolved in a sucrose phosphorylase enzyme liquid containing *S. mutans*-derived sucrose phosphorylase prepared according to Section 2.5 above to obtain solutions having final concentrations of 40 mM, 100 mM and 400 mM relative to the solution after the dissolution. A sucrose phosphorylase enzyme liquid without added sodium phosphate was used as a control (no addition). Also, as a control, the case where sucrose was added to a concentration of 10% was studied. These solutions were heated in a water bath at 55° C. The solutions were sampled at the start of the heating (0 minutes), and at 30 minutes, 60 minutes and 90 minutes after the start of the heating to measure the activity of sucrose phosphorylase in accordance with the method described herein.

Based on the measured activity, the residual activity was calculated.

Figure 21:
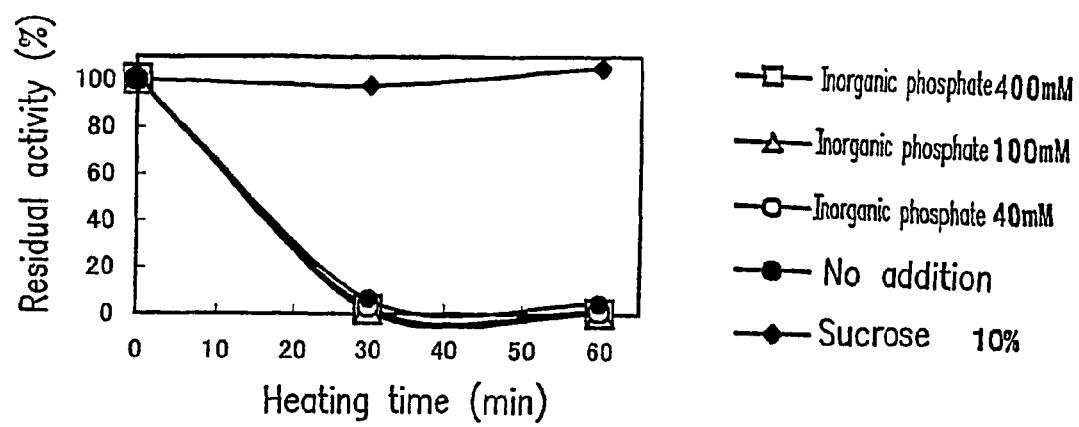
FIG. 21 is a graph showing the effect of inorganic phosphate on the stability of sucrose phosphorylase.

The results about the residual activity are shown in FIG. 21. As a result, inorganic phosphate was not recognized as having the effect of stabilizing sucrose phosphorylase as shown in sucrose.

Examples 22-1 to 22-5 and Comparative Example 22-1

Glucan Synthesis using Pullulan as a Primer

Glucan synthesis was conducted using reaction mixtures whose compositions (at the start of the reaction) are shown in Table 18 below.

TABLE 18

| No. | Sucrose (%) | P-5 (%) | Pi (mM) | SP (U/g sucrose) | GP (U/g sucrose) | Reaction temperature |
|---|---|---|---|---|---|---|
| Comparative example 22-1 | 4 | 0.2 | 20 | 20 | 20 | 50° C. |
| Example 22-1 | 8 | 0.4 | 40 | 20 | 20 | 50° C. |
| Example 22-2 | 10 | 0.5 | 50 | 20 | 20 | 50° C. |
| Example 22-3 | 15 | 0.75 | 75 | 20 | 20 | 50° C. |
| Example 22-4 | 20 | 1.0 | 100 | 20 | 20 | 50° C. |
| Example 22-5 | 25 | 1.25 | 125 | 20 | 20 | 50° C. |

P-5: Pullulan (average molecular weight was about 5,000); % was calculated by Weight/Volume.
Pi: Potassium dihydrogen phosphate-disodium hydrogen phosphate buffered solution
SP: Streptococcus mutans-derived sucrose phosphorylase
GP: Potato-derived glucan phosphorylase Specifically, 0.2 to 1.25% pullulan P-5 (average molecular weight was about 5,000; purchased from Shoko Co., Ltd.) was used instead of maltoheptaose, sucrose phosphorylase was used at an activity of 20 U/g sucrose, glucan phosphorylase was used at an activity of 20 U/g sucrose. Except for that, in comparative example 22-1 and Examples 22-1 to 22-5, glucan synthesis was conducted in the same manner as that in comparative example 3-2-1 and Examples 3-2-1 to 3-2-5.

After the reaction, the yield of synthesized glucan was determined according to Section 1.6 above. The results are shown in FIG. 22.

Even when pullulan was used instead of maltoheptaose, a highly efficient reaction could be conducted at 50° C. by increasing the sucrose concentration from 4% to 8% and the glucan yield was increased.

Figure 22:
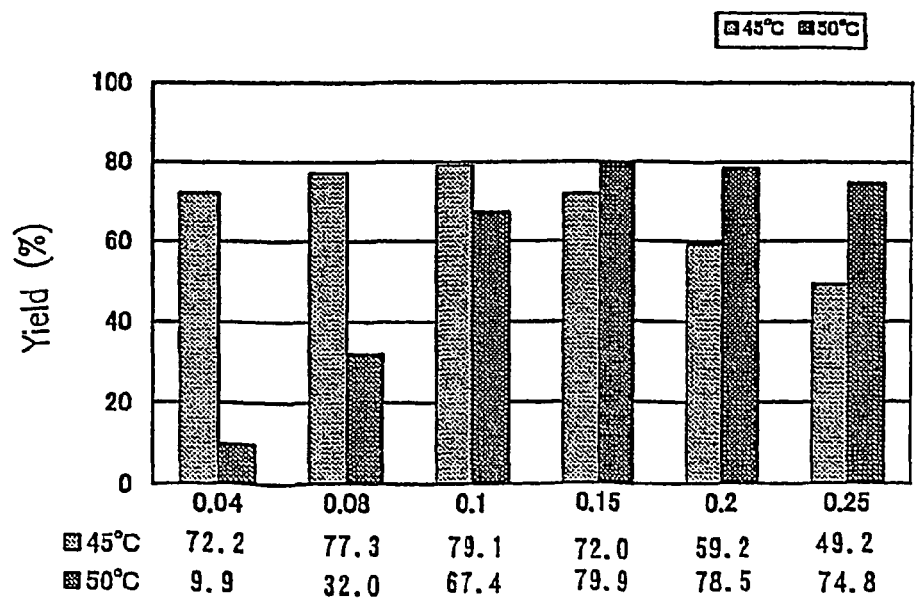
FIG. 22 is a graph showing the yields of glucan when reactions were conducted using pullulan as a primer at various initial sucrose concentrations were present and the reaction temperature was 50° C.

As shown in FIG. 22, when the reaction temperature was 50° C., the glucan yield was as low as 9.8% where the sucrose concentration was 4%. However, when the proportions among the substrates and the amounts of the enzymes were not changed and the sucrose concentration was varied between 8% and 25%, the glucan yield was increased. When the sucrose concentration was 8%, the yield was 32.0% which was at least three times as great as the yield where the sucrose concentration was 4%. When the sucrose concentration was at least 15%, the glucan yield was about 80%. Thus, even when pullulan was used instead of malto-oligosaccharide, an effect equivalent to that when malto-oligosaccharide was used was obtained.

Examples 23-1 to 23-7 and Comparative Example 23-1

Glucan Synthesis using Pullulan as a Primer

Glucan synthesis was conducted using reaction mixtures whose compositions (at the start of the reaction) are shown in Table 19 below.

TABLE 19

| No. | Sucrose (mM) | P-5 (%) | Pi (mM) | SP (U/g sucrose) | GP (U/g sucrose) | Reaction temperature |
|---|---|---|---|---|---|---|
| Comparative example 23-1 | 125 | 0.2 | 7.2 | 20 | 20 | 45° C. |
| Example 23-1 | 125 | 0.2 | 10 | 20 | 20 | 45° C. |
| Example 23-2 | 125 | 0.2 | 20 | 20 | 20 | 45° C. |
| Example 23-3 | 125 | 0.2 | 30 | 20 | 20 | 45° C. |
| Example 23-4 | 125 | 0.2 | 50 | 20 | 20 | 45° C. |
| Example 23-5 | 125 | 0.2 | 75 | 20 | 20 | 45° C. |
| Example 23-6 | 125 | 0.2 | 100 | 20 | 20 | 45° C. |
| Example 23-7 | 125 | 0.2 | 125 | 20 | 20 | 45° C. |

P-5: Pullulan (average molecular weight was about 5,000); % was calculated by Weight/Volume.
Pi: Potassium dihydrogen phosphate-disodium hydrogen phosphate buffered solution
SP: Streptococcus mutans-derived sucrose phosphorylase
GP: Potato-derived glucan phosphorylase Specifically, 0.2% pullulan P-5 (average molecular weight about 5,000; purchased from Shoko Co., Ltd.) was used instead of maltoheptaose. Except for that, in comparative example 23-1 and Examples 23-1 to 23-7, glucan synthesis was conducted in the same manner as that in comparative example 17-1 and Examples 17-1 to 17-7.

After the reaction, the yield of synthesized glucan was determined according to Section 1.6 above. The results are shown in FIG. 23.

Figure 23:
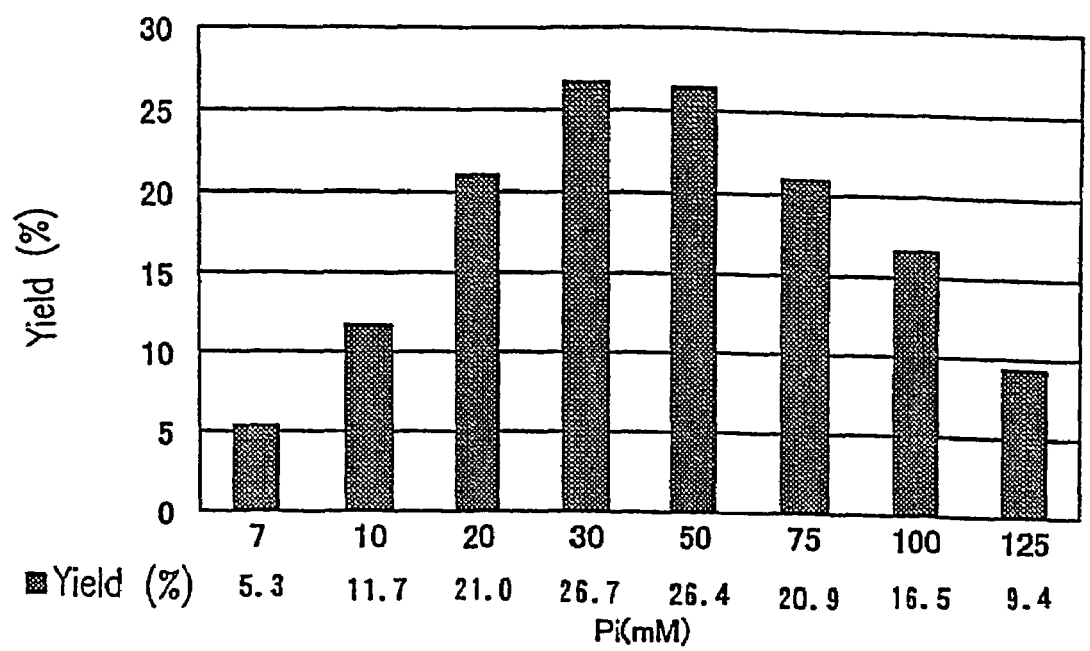
FIG. 23 is a graph showing the yields of glucan when reactions were conducted using pullulan as a primer at various initial inorganic phosphate concentrations and the reaction temperature was 50° C.

As shown in FIG. 23, when 7.2 mM inorganic phosphate was added to and allowed to react with 125 mM sucrose, the glucan yield was as low as 5.3%. However, when 10 mM inorganic phosphate was added to and allowed to react with 125 mM sucrose, the yield was 11.7% which was at least twice the above. Further, when 20 to 75 mM inorganic phosphate was added to and allowed to react with 125 mM sucrose, the yield was at least 20 to 25%.

Thus, even when pullulan was used instead of malto-oligosaccharide, an effect equivalent to that when malto-oligosaccharide was used was obtained.

Examples 24-1 to 24-7 and Comparative example 24-1

Glucan Synthesis using G-1-P)

Glucan synthesis was conducted using reaction mixtures whose compositions (at the start of the reaction) are shown in Table 20 below.

TABLE 20

| No. | Sucrose (mM) | G7 (mM) | G-1-P (mM) | SP (U/g sucrose) | GP (U/g sucrose) | Reaction temperature |
|---|---|---|---|---|---|---|
| Comparative example 24-1 | 125 | 0.35 | 7.2 | 20 | 20 | 45° C. |
| Example 24-1 | 125 | 0.35 | 10 | 20 | 20 | 45° C. |
| Example 24-2 | 125 | 0.35 | 20 | 20 | 20 | 45° C. |
| Example 24-3 | 125 | 0.35 | 30 | 20 | 20 | 45° C. |
| Example 24-4 | 125 | 0.35 | 50 | 20 | 20 | 45° C. |
| Example 24-5 | 125 | 0.35 | 75 | 20 | 20 | 45° C. |
| Example 24-6 | 125 | 0.35 | 100 | 20 | 20 | 45° C. |
| Example 24-7 | 125 | 0.35 | 125 | 20 | 20 | 45° C. |

G7: Maltoheptaose
G-1-P: Disodium glucose-1-phosphate
SP: Streptococcus mutans-derived sucrose phosphorylase
GP: Potato-derived glucan phosphorylase Specifically, glucose-1-phosphate was used instead of inorganic phosphate, and acetate buffered solution was used to adjust the reaction liquid to pH 7.0. Except for that, in comparative example 24-1 and Examples 24-1 to 24-7, glucan synthesis was conducted in the same manner as that in comparative example 17-1 and Examples 17-1 to 17-7.

After the reaction, the yield of synthesized glucan was determined according to Section 1.6 above. The results are shown in FIG. 24.

Figure 24:
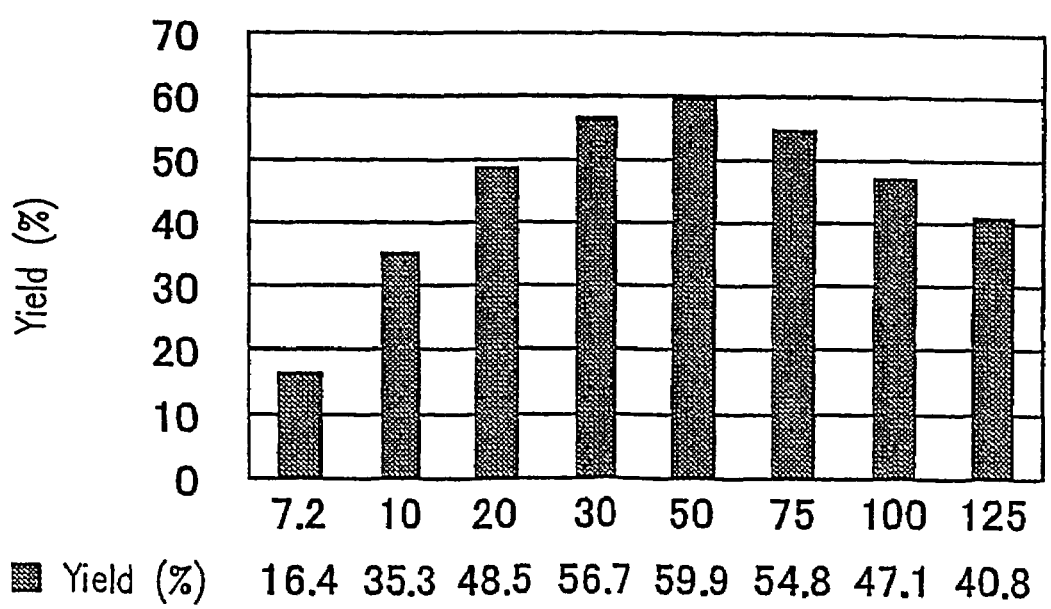
FIG. 24 is a graph showing the glucan yield when glucose-1-phosphate was used as a substrate.

As shown in FIG. 24, when 7.2 mM glucose-1-phosphate was added to and allowed to react with 125 mM sucrose, the glucan yield was as low as 16.4%. However, when 10 mM glucose-1-phosphate was added to and allowed to react with 125 mM sucrose, the yield was 35.3% which was at least twice the above. Further, when 20 to 75 mM glucose-1-phosphate was added to and allowed to react with 125 mM sucrose, the yield was at least 40 to 60%.

Thus, even when glucan was synthesized using glucose-1-phosphate instead of inorganic phosphate, the productivity was low in the case of the maximum value of the sucrose-phosphate ratio for conventional methods. However, at least double productivity was obtained by setting the maximum value of the sucrose-phosphate ratio within a predetermined range.

Examples 25-1 to 25-5

Glucan Synthesis using a SP-GP Reaction System Containing a Branching Enzyme

Glucan synthesis was conducted using reaction mixtures whose compositions are shown in Table 21 below. It should be noted that the branching enzyme used was prepared in accordance with the method disclosed in Japanese Laid-Open Publication No. 2000-316581 (Japanese Patent Application No. 11-130833).

TABLE 21

| No. | Sucrose (%) | G7 (μM) | Pi (mM) | SP (U/g sucrose) | GP (U/g sucrose) | BE (U/g sucrose) |
|---|---|---|---|---|---|---|
| Example 25-1 | 8 | 40 | 40 | 20 | 20 | 2500 |
| Example 25-2 | 8 | 40 | 40 | 20 | 20 | 5000 |
| Example 25-3 | 8 | 40 | 40 | 20 | 20 | 10000 |
| Example 25-4 | 12 | 80 | 60 | 20 | 20 | 5000 |
| Example 25-5 | 12 | 80 | 60 | 20 | 20 | 10000 |

G7: Maltoheptaose
Pi: Potassium dihydrogen phosphate-disodium hydrogen phosphate buffered solution
SP: Streptococcus mutans-derived sucrose phosphorylase
GP: Potato-derived glucan phosphorylase
BE: Aquifex aeolicus-derived branching enzyme This solution was allowed to react at 45° C. for 18 hours to synthesize glucan. The reaction volume was 1 ml.

After the reaction, the yield of the synthesized glucan was measured in a manner as described in 1.6 above. Further, the average unit chain length of the synthesized glucan was measured by a method shown in Takata et al. (Carbohydr. Res., Vol. 295, pp. 91 to 101 (1996)). The results are shown in Table 22 below.

TABLE 22

| No. | Yield (%) | Average unit chain length |
|---|---|---|
| Example 25-1 | 69.7 | N/A |
| Example 25-2 | 79.7 | 18 |
| Example 25-3 | 64.8 | 9 |
| Example 25-4 | 85.3 | 20 |
| Example 25-5 | 87.9 | 13 |

N/A: not analyzed

It was found that highly-branched glucan could be synthesized at a high yield under these conditions.

INDUSTRIAL APPLICABILITY

According to the present invention, glucans can be produced. By setting the maximum value of the ratio of the mole concentration of sucrose to the sum of the mole concentrations of inorganic phosphate and glucose-1-phosphate during a time from the start of a reaction to the end of the reaction, within a certain range, glucan production at a higher level of productivity than conventional methods can be obtained. The present inventors could produce glucans (preferably amylose) at high temperature by conducting reactions under conditions which improve the thermal stability of sucrose phosphorylase, or developing and using sucrose phosphorylase having a higher level of heat-resistance.

Such glucans are useful as raw materials for starch processing industries, dietary compositions, compositions for food additives, adhesive compositions, inclusion compounds and absorbing compounds, medical and cosmetic compositions, film-type product compositions, and as an alternative for starches used in biodegradable plastics.

The invention claimed is:
1. A method for producing glucans, comprising the step of:
   allowing a reaction solution containing sucrose, a primer, inorganic phosphate or glucose-1-phosphate, sucrose phosphorylase, and glucan phosphorylase to react to produce glucans, wherein the maximum value of the sucrose-phosphate ratio of the reaction solution from the start of the reaction to the end of the reaction is at least about 1 and no more than 12.5, wherein the glucan is a saccharide in which the component unit is D-glucose having at least two saccharide units linked by an α-1,4-glucoside bond, and wherein the primer is a molecule which has at least one free portion to which a saccharide unit can bind with an α-1,4-glucoside bond.

2. A method according to claim 1, wherein the maximum value is at least about 1 and no more than about 10.

3. A method according to claim 2, wherein the maximum value is at least about 2 and no more than about 7.

4. A method according to claim 1, wherein the glucan is amylose.

5. A method according to claim 1, wherein the sucrose phosphoiylase is derived from a bacterium belonging to the genus *Streptococcus*.

6. A method according to claim 5, wherein the sucrose phosphorylase is derived from a bacterium belonging to the genus *Streptococcus* selected from the group consisting of *Streptococcus mutans, Streptococcus thermophilus, Streptococcus pneumoniae*, and *Streptococcus mitis*.

7. A method according to claim 1, wherein the glucan phosphorylase is derived from a plant.

8. A method according to claim 7, wherein the glucan phosphorylase is derived from an alga.

9. A method according to claim 7, wherein the glucan phosphorylase is derived from potato.

10. A method according to claim 1, wherein the glucan phosphorylase is derived from *Thermus aquaticus*.

11. A method according to claim 1, wherein the glucan phosphorylase is derived from *Bacillus stearothermophilus*.

12. A method according to claim 1, wherein both or at least one of the sucrose phosphorylase and the glucan phosphorylase is produced by a recombinant microorganism.

13. A method according to claim 1, wherein both or at least one of the sucrose phosphorylase and the glucan phosphorylase is immobilized on a carrier.

14. A method according to claim 1, wherein the primier is selected from the group consisting of malto-oligosaccharide, amylose, amylopectin, glycogen, dextrin, pullulan, coupling sugar, starch, and derivatives thereof, wherein the derivative is a derivative in which at least one alcoholic hydroxyl group of the above-described saccharide has been hydroxyalkylated, alkylated, acetylated, carboxymethylated, sulfated, or phosphorylated.

15. A method according to claim 14, wherein the malto-oligosaccharide is a malto-oligosaccharide mixture.

16. A method according to claim 15, wherein the malto-oligosaccharide mixture contains at least one of maltotriose, maltose, and glucose in addition to malto-oligosaccharides having a degree of polymerization greater than or equal to that of maltotetraose.

17. A method according to claim 14, wherein the starch is selected from the group consisting of soluble starch, waxy starch, high amylose starch, starch degraded by a debranching enzyme, starch degraded by phosphorylase, starch partially degraded by hydrolysis, processed starch, and derivatives thereof, wherein the derivative is a derivative in which at least one alcoholic hydroxyl group of the above-described saccharide has been hydroxyalkylated, alkylated, acetylated, carboxymethylated, sulfated, or phosphorylated.

18. A method according to claim 1, further comprising the step of purifying the produced glucans without using an organic solvent.

19. A method according to claim 1, further comprising the steps of cooling the reaction solution after the reaction to precipitate the glucans, and purifying the precipitated glucan by a solid-liquid separation method.

20. A method according to claim 1, further comprising the steps of:

cooling the reaction solution during or after the glucan producing reaction to gel the glucans;

recovering the gelled glucans; and removing fructose from the gelled glucans by an operation selected from the group consisting of washing with water, freeze-thawing, filtration, squeezing, suction and centrifugation.

21. A method according to claim 1, further comprising the step of subjecting glucans dissolved in water after the glucan producing reaction to membrane fractionation using an ultrafiltration membrane or chromatography without precipitation to remove fructose.

22. A method according to claim 1, wherein the reaction solution further contains an enzyme selected from the group consisting of debranching enzymes, branching enzymes, 4-α-glucanotransferase, and glycogen debranching enzymes.

23. A method for producing glucans, comprising the step of:

allowing a reaction solution containing sucrose, a primer, inorganic phosphate or glucose-1-phosphate, sucrose phosphorylase, and glucan phosphorylase to react to produce glucans, wherein the reaction is conducted at a temperature of 45° C. to about 70° C., wherein the glucan is a saccharide in which the component unit is D-glucose having at least two saccharide units linked by an α-1,4-glucoside bond, wherein the primer is a molecule which has at least one free portion to which a saccharide unit can bind with an α-1,4-glucoside bond, and wherein the sucrose concentration of the reaction solution is 8% to about 100% at the start of the reaction.

24. A method according to claim 23, wherein the reaction temperature is 45° C. to about 65° C.

25. A method according to claim 23, wherein the sucrose concentration of the reaction solution is 8% to about 80% at the start of the reaction.

26. A method according to claim 25, wherein the sucrose concentration of the reaction solution is about 15% to about 50% at the start of the reaction.

27. A method according to claim 23, wherein the glucan is amylose.

28. A method according to claim 23, wherein the sucrose phosphorylase is derived from a bacterium belonging to the genus *Streptococcus*.

29. A method according to claim 28, wherein the sucrose phosphorylase is derived from a bacterium belonging to the genus *Streptococcus* selected from the group consisting of *Streptococcus mutans, Streptococcus thermophilus, Streptococcus pneumoniae*, and *Streptococcus mitis*.

30. A method according to claim 23, wherein the glucan phosphorylase is derived from a plant.

31. A method according to claim 30, wherein the glucan phosphorylase is derived from an alga.

32. A method according to claim 30, wherein the glucan phosphorylase is derived from potato.

33. A method according to claim 23, wherein the glucan phosphorylase is derived from *Thermus aquaticus*.

34. A method according to claim 23, wherein the glucan phosphoirylase is derived from *Bacillus stearothermophilus*.

35. A method according to claim 23, wherein both or at least one of the sucrose phosphorylase and the glucan phosphorylase is produced by a recombinant microorganism.

36. A method according to claim 23, wherein both or at least one of the sucrose phosphorylase and the glucan phosphorylase is immobilized on a carrier.

37. A method according to claim 23, wherein the primer is selected from the group consisting of malto-oligosaccharide, amylose, amylopectin, glycogen, dextrin, pullulan, coupling sugar, starch, and derivatives thereof, wherein the derivative is a derivative in which at least one alcoholic hydroxyl group of the above-described saccharide has been hydroxyalkylated, alkylated, acetylated, carboxymethylated, sulfated, or phosphorylated.

38. A method according to claim 37, wherein the malto-oligosaccharide is a malto-oligosaccharide mixture.

39. A method according to claim 38, wherein the malto-oligosaccharide mixture contains at least one of maltotriose, maltose, and glucose in addition to malto-oligosaccharides having a degree of polymerization greater than or equal to that of maltotetraose.

40. A method according to claim 37, wherein the starch is selected from the group consisting of soluble starch, waxy starch, high amylose starch, starch degraded by a debranching enzyme, starch degraded by phosphorylase, starch partially degraded by hydrolysis, processed starch, and derivatives thereof, wherein the derivative is a derivative in which at least one alcoholic hydroxyl group of the above-described saccharide has been hydroxyalkylated, alkylated, acetylated, carboxymethylated, sulfated, or phosphorylated.

41. A method according to claim 23, further comprising the step of purifying the produced glucans without using an organic solvent.

42. A method according to claim 23, further comprising the steps of cooling the reaction solution after the reaction to precipitate the glucans, and purifying the precipitated glucan by a solid-liquid separation method.

43. A method according to claim 23, further comprising the steps of:
cooling the reaction solution during or after the glucan producing reaction to gel the glucans;
recovering the gelled glucans; and
removing fructose from the gelled glucans by an operation selected from the group consisting of washing with water, freeze-thawing, filtration, squeezing, suction and centrifugation.

44. A method according to claim 23, further comprising the step of subjecting glucans dissolved in water after the glucan producing reaction to membrane fractionation using an ultrafiltration membrane or chromatography without precipitation to remove fructose.

45. A method according to claim 23, wherein the reaction solution further contains an enzyme selected from the group consisting of debranching enzymes, branching enzymes, 4-α-glucanotransferase, and glycogen debranching enzymes.

46. A method for producing glucans, comprising the step of:
allowing a reaction solution containing sucrose, a primer, inorganic phosphate or glucose-1-phosphate, sucrose phosphorylase, and glucan phosphorylase to react to produce glucans,
wherein the maximum value of the sucrose-phosphate ratio of the reaction solution from the start of the reaction to the end of the reaction is at least about 1 and no more than 12.5, and the reaction is conducted at a temperature of about 40° C. to about 70° C.,
wherein the glucan is a saccharide in which the component unit is D-glucose having at least two saccharide units linked by an α-1,4-glucoside bond,
wherein the primer is a molecule which has at least one free portion to which a saccharide unit can bind with an α-1,4-glucoside bond, and
wherein the sucrose concentration of the reaction solution is about 5% to about 100% at the start of the reaction.

47. A method for producing glucans, comprising the step of:
allowing a reaction solution containing sucrose, a primer, inorganic phosphate or glucose-1-phosphate, sucrose phosphorylase, and glucan phosphorylase to react to produce glucans,
wherein the sucrose-phosphate ratio of the reaction solution at the start of the reaction is at least about 1 and no more than 12.5,
wherein the glucan is a saccharide in which the component unit is D-glucose having at least two saccharide units linked by an α-1,4-glucoside bond, and
wherein the primer is a molecule which has at least one free portion to which a saccharide unit can bind with an α-1,4-glucoside bond.

48. A method according to claim 47, wherein the reaction is conducted at a temperature of about 40° C. to about 70° C.

49. A method for producing glucans, comprising the steps of:
allowing a reaction solution containing sucrose, a primer, inorganic phosphate or glucose-1-phosphate, sucrose phosphorylase, and glucan phosphorylase to start a reaction;
further adding sucrose, inorganic phosphate or glucose-1-phosphate to the reaction solution; and
further continuing the reaction to produce glucans,
wherein the sucrose-phosphate ratio of the reaction solution at the time of finishing the addition step is at least about 1 and no more than 12.5,
wherein the glucan is a saccharide in which the component unit is D-glucose having at least two saccharide units linked by an α-1,4-glucoside bond, and
wherein the primer is a molecule which has at least one free portion to which a saccharide unit can bind with an α-1,4-glucoside bond.

50. A method according to claim 49, wherein the reaction is conducted at a temperature of about 40° C. to about 70° C.

* * * * *